US009592286B2

(12) United States Patent
Wu et al.

(10) Patent No.: US 9,592,286 B2
(45) Date of Patent: Mar. 14, 2017

(54) COMBINED VACCINES FOR PREVENTION OF PORCINE VIRUS INFECTIONS

(75) Inventors: Hua Wu, Beijing (CN); Yanliang He, Beijing (CN); Mingqi Xia, Beijing (CN)

(73) Assignee: Sinovet (Beijing) Biotechnology Co., Ltd., Beijing (CN)

( * ) Notice: Subject to any disclaimer, the term of this patent is extended or adjusted under 35 U.S.C. 154(b) by 0 days.

(21) Appl. No.: 14/122,627

(22) PCT Filed: May 25, 2012

(86) PCT No.: PCT/CN2012/076125
§ 371 (c)(1),
(2), (4) Date: Nov. 26, 2013

(87) PCT Pub. No.: WO2012/163258
PCT Pub. Date: Dec. 6, 2012

(65) Prior Publication Data

US 2014/0093535 A1 Apr. 3, 2014

(30) Foreign Application Priority Data

May 27, 2011 (CN) .......................... 2011 1 0140951
Oct. 27, 2011 (CN) .......................... 2011 1 0331159
Oct. 27, 2011 (CN) .......................... 2011 1 0331206

(51) Int. Cl.
*A61K 39/12* (2006.01)
*A61K 39/00* (2006.01)

(52) U.S. Cl.
CPC ...... *A61K 39/12* (2013.01); *A61K 2039/5254* (2013.01); *A61K 2039/552* (2013.01); *A61K 2039/70* (2013.01); *C12N 2710/16734* (2013.01); *C12N 2770/10034* (2013.01); *C12N 2770/24334* (2013.01)

(58) Field of Classification Search
None
See application file for complete search history.

(56) References Cited

U.S. PATENT DOCUMENTS

2010/0267929 A1* 10/2010 Faaberg et al. ............... 530/350
2011/0150770 A1* 6/2011 Bautista et al. ............... 424/9.2
2014/0093535 A1* 4/2014 Wu ........................ A61K 39/12 424/202.1

FOREIGN PATENT DOCUMENTS

| | | | |
|---|---|---|---|
| CN | 1513987 | A | 7/2004 |
| CN | 101280292 | A | 10/2008 |
| CN | 101307305 | A | 11/2008 |
| CN | 101603035 | A | 12/2009 |
| CN | 101633909 | A | 1/2010 |
| CN | 101690808 | A | 4/2010 |
| CN | 101879311 | A | 11/2010 |
| CN | 101991849 | A | 3/2011 |
| EP | 0835930 | A1 | 4/1998 |
| EP | 1792996 | A1 | 6/2007 |
| KR | 2010-0121288 | A | 11/2010 |
| KR | 2010-0121289 | A | 11/2010 |
| WO | 2006/129139 | A1 | 12/2006 |

OTHER PUBLICATIONS

Sun et al. (Sheng Wu Gong Cheng Xue Bao. 2008; 24 (10): 1714-1722, abstract only).*
De Bruin et al. (Veterinary Immunology and Immunopathology. 2000; 76: 125-135).*
Wu (English translation provided for CN 101633909 Jan. 2010).*
Han et al. (Journal of Virology. 2007; 81 (18): 9878-9890).*
Leng et al. (Veterinary Microbiology. 2012; 157: 50-60).*
Tian et al. (PLoS One 2(6): e526, (2007) doi:10.1371).*
Liu et al. (Virus Research. 2015; 208: 13-21).*
Kim et al. (Virus Genes. 2009; 38: 118-128).*
Sun, Jianfu, "Immune Responses Induced by the Suicidal DNA Vaccines Co-expressing the GP5 Protein of Porcine Reproductive and Respiratory Syndrome Virus and the E2 Protein of Classical Swine Fever Virus in Mice," Chinese Master's Theses Full-text Database Agriculture Science and Technology 3:D050-91 (2010).
Qiu et al., "The Lapinized Chinese Strain of Classical Swine Fever Virus: a Retrospective Review Spanning Half a Century," Scientia Agricultura Sinica 38(8):1675-1685 (2005).
Du et al., "Effect of PRRS Attenuated Vaccination on the Immunization of Swine Fever Cell Vaccination," China Academic Journal Electronic Publishing House 1005-7307 (2011).
Zhu et al., "The Research Progress on Classical Swine Fever (CSF) Vaccine," China Academic Journal Electronic Publishing House 39(2):1002-1280 (2005).
Li et al., "Infection of Porcine Reproductive and Respiratory Syndrome Virus Suppresses the Antibody Response to Classical Swine Fever Virus Vaccination," Veterinary Microbiology 95:295-301 (2003).
Suradhat et al., "Negative Impact of Porcine Reproductive and Respiratory Syndrome Virus Infection on the Efficacy of Classical Swine Fever Vaccine," Vaccine 24:2634-2642 (2006).
PCT International Search Report for PCT/CN2012/076125, filed May 25, 2012 (mailed Sep. 6, 2012).
Shen et al., "Study on Immunization with PRRS and HC Vaccines Singly and Simultaneously," Shanghai Journal of Animal Husbandry and Veterinary Medicine 5:40-41 (2005).
Guo et al., "Development of Oil Emulsion Inactivated Vaccine of Porcine Reproductive and Respiratory Syndrome," Chinese J. Preventive Veterinary Med. 22(4):259-262 (2000).
Koenig et al., "CP7_E2alf: A Safe and Efficient Marker Vaccine Strain for Oral Immunisation of Wild Boar Against Classical Swine Fever Virus (CSFV)" Vaccine 25:3391-3399 (2007).
Office action and translation for corresponding Japanese Patent Application No. 2014-511724 (Dec. 1, 2015).

* cited by examiner

*Primary Examiner* — Shanon A Foley
(74) *Attorney, Agent, or Firm* — LeClairRyan, a Professional Corporation

(57) ABSTRACT

The present disclosure provides vaccine compositions comprising a PRRSV vaccine and a second porcine vaccine, which are substantially free from immuno-inhibition against each other. The second porcine virus vaccine can be CSFV and/or PRV. The preparation methods for the vaccines and the formulations are also provided. The vaccine compositions provided herein confer protective immunity to pigs against porcine reproductive and respiratory syndrome, classical swine fever, and/or pseudorabies.

49 Claims, 20 Drawing Sheets

360 continuous nucleotides absent in Nsp2 coding sequence of PRRSV TJM strain

| 5 10 15 20 25 30 35 40 45 |
|---|
| TCAAGTGTTAAGATCACACGCCCAAAATACTCAGCTCAAGCCATC |
| ATCGACTCTGGCGGGCCTTGCAGTGGGCATCTCCAAAAGGAAAAA |
| GAAGCATGCCTCAGCATCATGCGTGAGGCTTGTGATGCGTCCAAG |
| CTTGGTGATCCTGCTACGCAGGAGTGGCTCTCTCGCATGTGGGATA |
| GGGTTGACATGCTGACTTGGCGCAACACGTCTGCTTACCAGGCGT |
| TTCGCATCTTAAATGGCAGTTTGAGTTTCTCCCAAAGATGATTCTCG |
| AGACACCGCCGCCCCACCCGTGCGGGTTTGTGATGTTACCTCGCAC |
| GCCTGCACCTTCCGTGAGTGCAGAGAGTGACCTCACCATT |

Figure 1

Protein sequence absent in Nsp2 protein of PRRSV TJM strain

| 5 10 15 20 25 30 35 40 45 50 |
|---|
| SSVKITRPKYSAQAIIDSGGPCSGHLQKEKEACLSIMREACDASKLGDPA |
| TQEWLSRMWDRVDMLTWRNTSAYQAFRILNGRFEFLPKMILETPPPHPC |
| GFVMLPRTPAPSVSAESDLTI |

Figure 2

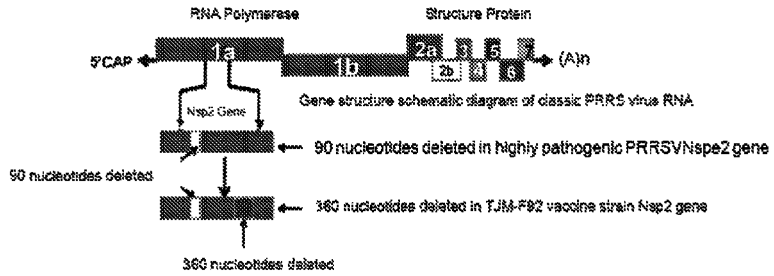

Figure 3

```
      C C T A A C G G T T C G G A A G A - - - A A C T G T C G G T  Majority
                2770                2780                2790
2761  C C T A A C A G T T G G G A A G A T T T G G C T G T T A G T  VR-2332
2761  C C T A A C G G T T C G G A A G A - - - A A C T G T C G G T  TJ
2761  C C T A A C G G T T C G G A A G A - - - A A C T G T C G G T  TJM-F92

      C C T G C A C C G C G T A G A A C T G T - - - - - - - - - -  Majority
                2920                2930                2940
2911  C C C G C A C C T C G C G G A A C T G T G T C T C G A C C G  VR-2332
2908  C C T G C A C C G C G T A G A A C T G T - - - - - - - - - -  TJ
2908  C C T G C A C C G C G T A G A A C T G T - - - - - - - - - -  TJM-F92

      - - - - - - - - - - - - - - - - - - - - - - - - - - - - - -  Majority
                2950                2960                2970
2941  G T G A C A C C C T T G A G T G A G C C G A T C C C T G T G  VR-2332
2929  - - - - - - - - - - - - - - - - - - - - - - - - - - - - - -  TJ
2929  - - - - - - - - - - - - - - - - - - - - - - - - - - - - - -  TJM-F92

      - - - - - - - - - - - - - - - - - - - - - - - - - - - - - -  Majority
                2980                2990                3000
2971  C C C G C A C C G C G G C G T A A G T T T C A G C A G G T G  VR-2332
2929  - - - - - - - - - - - - - - - - - - - - - - - - - - - - - -  TJ
2929  - - - - - - - - - - - - - - - - - - - - - - - - - - - - - -  TJM-F92

      - - - - - - - - - - - - - - - - - G A C A A C A A C G C T G  Majority
                3010                3020                3030
3001  A A A A G A T T G A G T T C G G C G G C G G C A A T C C C A  VR-2332
2929  - - - - - - - - - - - - - - - - - A A C A A C A A C G C T G  TJ
2929  - - - - - - - - - - - - - - - - - G A C A A C A A C G C T G  TJM-F92
```

Figure 4

SEQUENCE LISTING

```
<160> NUMBER OF SEQ ID NOS: 11

<210> SEQ ID NO 1
<211> LENGTH: 1149
<212> TYPE: DNA
<213> ORGANISM: Porcine reproductive and respiratory syndrome virus

<400> SEQUENCE: 1

atgtctggga tacttgatcg gtgcacgtgt acccccaatg ccagggtgtt tgtggcggag     60

ggccaggtct actgcacacg atgtctcagt gcacggtctc tccttcctct gaatctccaa    120

gttcctgagc ttggggtgct gggtctattc tataggcccg aagagccact ccggtggacg    180

ttgccacgtg cattccccac tgtcgagtgc tcccccgccg gggcctgctg gctttctgcg    240

atctttccga ttgcacgaat gactagtgga aacctgaact ttcaacaaag aatggtgcgg    300

gtcgcagctg aaatctacag agccggccaa ctcaccccta cagttctaaa gactctacaa    360

gtttatgaac ggggttgtcg ctggtacccc attgtcgggc ccgtccctgg ggtgggcgtt    420

tacgccaact ccctgcatgt gagtgacaaa cctttcccgg gagcaactca tgtgttaacc    480

aacttgccgc tcccgcagag gcccaaacct gaggactttt gcccttttga gtgtgctatg    540

gctgacgtct atgacattgg tcgtggcgcc gtcatgtatg tggccggagg aaaggtctct    600

tgggcccctc gtggtgggaa tgaagtgaaa tttgaacctg tccccaagga gttgaagttg    660

gttgcgaacc gactccacac ctccttcccg ccccatcacg tagtggacat gtccaggttt    720

accttcatga cccctgggag tggtgtctcc atgcgggttg agtaccaata cggctgcctc    780

cccgctgaca ctgtccctga aggaaactgc tggtggcgct tgtttgactc gctcccaccg    840

gaagttcagt acaaagaaat tcgccacgct aaccaatttg gctatcaaac caagcatggt    900

gtccctggca agtacctaca gcggaggctg caagttaatg gtcttcggac agtgaccgac    960

acacatggac ctatcgtcat acagtacttc tctgttaagg agagttggat ccgccacctg   1020

aagttggtgg aagaacccag cctccccggg tttgaggatc tcctcagaat cagggttgag   1080

cccaatacgt caccactggc tggaaaggat gagaagattt tccggtttgg cagtcataag   1140

tggtacggt                                                           1149

<210> SEQ ID NO 2
<211> LENGTH: 2490
<212> TYPE: DNA
<213> ORGANISM: Porcine reproductive and respiratory syndrome virus

<400> SEQUENCE: 2

gccggaaaga gagcaaggaa aacacgctct ggtgcgacta ctatggtcgc tcatcacgct     60

tcgtccgctc ataaaatccg gcaggccacg aagcacgagg gtgccggcgc taacaaggct    120

gagcatctca agcgctactc tccgcctgcc gaagggaact gtggttggca ctgcatttcc    180

gccatcgcca accggatggt gaattccaac tttgagacca cccttcctga aagagtaagg    240

ccttcagatg actgggccac tgacgaggat cttgtgaata ccatccaaat cctcaggctc    300

cctgcggcct tggacaggaa cggcgcttgc ggtagcgcca agtacgtgct taaactggag    360
```

```
ggtgagcatt ggactgtctc tgtgatccct gggatgtccc ctactttgct ccccccttgaa    420
tgtgttcagg gttgttgtga acataagggc ggtcttgttt ccccggatgc ggtcgaaatt    480
tccggatttg atcctgcctg ccttgaccga ctggctaagg taatgcactt gcctagcagt    540
accatcccag ccgctctggc cgaattgtcc gacgactcca accgtccggt ttccccggcc    600
gctactacgt ggactgtttc gcaattctat gctcgtcata gaggaggaga tcatcatgac    660
caggtgtgct tagggaaaat catcagcctt tgtcaagtta ttgaggactg ctgctgccat    720
cagaataaaa ccaaccgggc tactccggaa gaggtcgcgg caaagattga tcagtacctc    780
cgtgacgcaa caagtcttga ggaatgcttg gccaaacttg agagagtttc cccgccgagc    840
gcagcggaca cctcctttga ttggaatgtt gtgcttcctg ggttgaggc gacgaatcag    900
acaaccgaac aacctcacgt caactcatgc tgcaccccgg tccctcccgt gactcaagag    960
cctttgggcg aggactcggt ccctctgacc gccttctcac tgtccaattg ctattaccct   1020
gcacaaggtg acgaggttca tcaccgtgag aggttaaatt ccgcactctc taagttggaa   1080
gaggttgtcc tggaagaata tgggctcatg tccactggac ttggcccgcg acccgtgctg   1140
ccgagcgggc tcgacgagct taaagaccag atggaggagg atctgctaga actagccaac   1200
acccaggcga cttcagaaat gatggcctgg gcggctgagc aggtcgattt aaaagcttgg   1260
gtcaaaagct acccgcggtg gacaccacca cccccctccac caagagttca acctcgaaga   1320
acaaagtctg tcaaaagttt gccagaggac aagcctgtcc ctgctccgcg caggaaggtc   1380
agatccgatt gcggcagccc ggttttgatg ggcgacaatg tccctaacgg ttcggaagaa   1440
actgtcggtg gtctcctcaa ttttccgaca ccatccgagc cgatgacacc tatgagtgag   1500
cccgtacttg tgcccgcgtc gcgacgtgtc cccaagctga tgacaccttt gagtgggtcg   1560
gcaccagttc ctgcaccgcg tagaactgtg acaacaacgc tgacgcacca ggatgagcct   1620
ctggatttgt ctgcgtcctc acaaacggaa tatgaggctt ccccccctaac accatcgcag   1680
aacatgggca tcctggaggc ggggggcgaa gaagctgagg gagtcctgag tgaaatctcg   1740
gatatactaa atgacaccaa ccctgcacct gtgtcatcaa gcagctccct gggttcagtg   1800
gccaccgagg atgttccacg catcctcggg aaaataggag acactgacga gctgcttgac   1860
cggggtccct cggcaccctc caagggagaa ccggtctgtg accaacctgc caaagatccc   1920
cggatgtcgc cgcgggagtc tgacgagagc ataatagttc cgcccgcaga tacaggtggt   1980
gtcggctcat tcactgattt gccgtcttca gatggtgtgg atgtggacgg gggggggccg   2040
ttaagaacgg taaaaacaaa agcagaaagg ctcttagatc aactgagctg ccaggttttt   2100
agcctcgttt cccatctccc tattttcttc tcacacctct tcaaatctga cagtggttat   2160
tctccgggtg attggggttt tgcagctttt actctatttt gcctcttttt atgttacagt   2220
tacccattct tcggttttgc tcccctcttg ggtgtatttt ctgggtcttc tcggcgtgtg   2280
cgaatggggg tttttggctg ctggttggct tttgctgttg gtctgttcaa gcctgtgtcc   2340
gacccagtcg gcactgcttg tgagtttgac tcgccagagt gtaggaacgt ccttcattct   2400
tttgagcttc tcaaaccttg ggaccctgtc cgcagccttg ttgtgggccc cgtcggtctc   2460
ggccttgcca ttcttggcag gttactgggc                                      2490
```

<210> SEQ ID NO 3
<211> LENGTH: 14966
<212> TYPE: DNA
<213> ORGANISM: Porcine reproductive and respiratory syndrome virus

<400> SEQUENCE: 3

-continued

```
atgacgtata ggtgttggct ctatgccacg gcatttgtat tgtcaggagc tgtgaccata     60
ggcacagccc aaaacttgct gcacgggaac accctcctgt gacagccctc ttcaggggga    120
ttaggggtct gtccctaaca ccttgcttcc ggagttgcac tgctttacgg tctctccacc    180
cctttaacca tgtctgggat acttgatcgg tgcacgtgta cccccaatgc cagggtgttt    240
gtggcggagg gccaggtcta ctgcacacga tgtctcagtg cacggtctct ccttcctctg    300
aatctccaag ttcctgagct tggggtgctg ggtctattct ataggcccga agagccactc    360
cggtggacgt tgccacgtgc attccccact gtcgagtgct cccccgccgg ggcctgctgg    420
ctttctgcga tctttccgat tgcacgaatg actagtggaa acctgaactt tcaacaaaga    480
atggtgcggg tcgcagctga aatctacaga gccggccaac tcacccctac agttctaaag    540
actctacaag tttatgaacg gggttgtcgc tggtacccca ttgtcgggcc cgtccctggg    600
gtgggcgttt acgccaactc cctgcatgtg agtgacaaac ctttcccggg agcaactcat    660
gtgttaacca acttgccgct cccgcagagg cccaaacctg aggacttttg cccttttgag    720
tgtgctatgg ctgacgtcta tgacattggt cgtggcgccg tcatgtatgt ggccggagga    780
aaggtctctt gggcccctcg tggtgggaat gaagtgaaat ttgaacctgt ccccaaggag    840
ttgaagttgg ttgcgaaccg actccacacc tccttcccgc cccatcacgt agtggacatg    900
tccaggttta ccttcatgac ccctgggagt ggtgtctcca tgcgggttga gtaccaatac    960
ggctgcctcc ccgctgacac tgtccctgaa ggaaactgct ggtggcgctt gtttgactcg   1020
ctcccaccgg aagttcagta caaagaaatt cgccacgcta accaatttgg ctatcaaacc   1080
aagcatggtg tccctggcaa gtacctacag cggaggctgc aagttaatgg tcttcggaca   1140
gtgaccgaca cacatggacc tatcgtcata cagtacttct ctgttaagga gagttggatc   1200
cgccacctga agttggtgga agaacccagc ctccccgggt ttgaggatct cctcagaatc   1260
agggttgagc ccaatacgtc accactggct ggaaaggatg agaagatttt ccggtttggc   1320
agtcataagt ggtacggtgc cggaaagaga gcaaggaaaa cacgctctgg tgcgactact   1380
atggtcgctc atcacgcttc gtccgctcat aaaatccggc aggccacgaa gcacgagggt   1440
gccggcgcta acaaggctga gcatctcaag cgctactctc cgcctgccga agggaactgt   1500
ggttggcact gcatttccgc catcgccaac cggatggtga attccaactt tgagaccacc   1560
cttcctgaaa gagtaaggcc ttcagatgac tgggccactg acgaggatct tgtgaatacc   1620
atccaaatcc tcaggctccc tgcggccttg gacaggaacg gcgcttgcgg tagcgccaag   1680
tacgtgctta aactggaggg tgagcattgg actgtctctg tgatccctgg gatgtcccct   1740
actttgctcc cccttgaatg tgttcagggt tgttgtgaac ataagggcgg tcttgtttcc   1800
ccggatgcgg tcgaaatttc cggatttgat cctgcctgcc ttgaccgact ggctaaggta   1860
atgcacttgc ctagcagtac catcccagcc gctctggccg aattgtccga cgactccaac   1920
cgtccggttt ccccggccgc tactacgtgg actgtttcgc aattctatgc tcgtcataga   1980
ggaggagatc atcatgacca ggtgtgctta gggaaaatca tcagcctttg tcaagttatt   2040
gaggactgct gctgccatca gaataaaacc aaccgggcta ctccggaaga ggtcgcggca   2100
aagattgatc agtacctccg tgacgcaaca agtcttgagg aatgcttggc caaacttgag   2160
agagtttccc cgccgagcgc agcggacacc tcctttgatt ggaatgttgt gcttcctggg   2220
gttgaggcga cgaatcagac aaccgaacaa cctcacgtca actcatgctg caccccggtc   2280
cctcccgtga ctcaagagcc tttgggcgag gactcggtcc ctctgaccgc cttctcactg   2340
```

-continued

```
tccaattgct attaccctgc acaaggtgac gaggttcatc accgtgagag gttaaattcc   2400
gcactctcta agttggaaga ggttgtcctg gaagaatatg ggctcatgtc cactggactt   2460
ggcccgcgac ccgtgctgcc gagcgggctc gacgagctta aagaccagat ggaggaggat   2520
ctgctagaac tagccaacac ccaggcgact tcagaaatga tggcctgggc ggctgagcag   2580
gtcgatttaa aagcttgggt caaaagctac ccgcggtgga caccaccacc ccctccacca   2640
agagttcaac ctcgaagaac aaagtctgtc aaaagtttgc cagaggacaa gcctgtccct   2700
gctccgcgca ggaaggtcag atccgattgc ggcagcccgg ttttgatggg cgacaatgtc   2760
cctaacggtt cggaagaaac tgtcggtggt ctcctcaatt ttccgacacc atccgagccg   2820
atgacaccta tgagtgagcc cgtacttgtg cccgcgtcgc gacgtgtccc caagctgatg   2880
acacctttga gtgggtcggc accagttcct gcaccgcgta gaactgtgac aacaacgctg   2940
acgcaccagg atgagcctct ggatttgtct gcgtcctcac aaacggaata tgaggcttcc   3000
cccctaacac catcgcagaa catgggcatc ctggaggcgg gggggcaaga agctgaggga   3060
gtcctgagtg aaatctcgga tatactaaat gacaccaacc ctgcacctgt gtcatcaagc   3120
agctccctgg gttcagtggc caccgaggat gttccacgca tcctcgggaa aataggagac   3180
actgacgagc tgcttgaccg ggtccctcg gcaccctcca agggagaacc ggtctgtgac   3240
caacctgcca aagatccccg gatgtcgccg cgggagtctg acgagagcat aatagttccg   3300
cccgcagata caggtggtgt cggctcattc actgatttgc cgtcttcaga tggtgtggat   3360
gtggacgggg gggggccgtt aagaacggta aaaacaaaag cagaaaggct cttagatcaa   3420
ctgagctgcc aggtttttag cctcgtttcc catctcccta ttttcttctc acacctcttc   3480
aaatctgaca gtggttattc tccgggtgat tggggttttg cagcttttac tctattttgc   3540
ctctttttat gttacagtta cccattcttc ggttttgctc ccctcttggg tgtattttct   3600
gggtcttctc ggcgtgtgcg aatgggggtt tttggctgct ggttggcttt tgctgttggt   3660
ctgttcaagc ctgtgtccga cccagtcggc actgcttgtg agtttgactc gccagagtgt   3720
aggaacgtcc ttcattcttt tgagcttctc aaaccttggg accctgtccg cagccttgtt   3780
gtgggccccg tcggtctcgg ccttgccatt cttggcaggt tactgggcgg ggcacgctac   3840
atctggcact ttttgcttag gcttggcatt gttgcagact gtgtcttggc tggagcttat   3900
gtgctttctc aaggtaggtg taaaaagtgc tggggatctt gtgtaagaac tgctcctaat   3960
gagatcgcct tcaacgtgtt cccttttaca cgtgcgacca ggtcgtcact catcgacctg   4020
tgcgatcggt tttgcgcacc aaaaggcatg gaccccattt ttctcgccac tgggtggcgt   4080
gggtgctgga ccggccggag tcccattgag caaccttctg aaaaacccat cgcgttcgcc   4140
cagctggatg agaagaggat tacggctaga actgtggtcg ctcagcctta tgatcccaac   4200
caggccgtaa agtgcttgcg ggtattacag gcgggtgggg cgatggtggc cgaggcagtc   4260
ccaaaagtgg tcaaagtttc cgctattcca ttccgagctc ctttctttcc cgctggagtg   4320
aaagttgatc ctgagtgcag aatcgtggtt gatcccgata cttttactac agccctccgg   4380
tctggctatt ccaccgcgaa cctcgtcctt ggtacggggg actttgccca gctgaatgga   4440
ctaaagatca ggcaaatttc caagccttca gggggaggcc cacacctcat tgctgccttg   4500
catgttgcct gctcgatggc gttacacatg cttgctggtg tttatgtaac tgcagtgggg   4560
tcctgcggtg ccggtaccaa cgatccgtgg tgcactaacc cgtttgctgt ccctggctat   4620
ggacctggct ctctttgcac gtctagattg tgcatctccc aacacggcct caccttgccc   4680
ttgacagcac ttgtggcggg attcggcctt caagagattg ccttggtcgt tttgatcttt   4740
```

-continued

```
gtctccatcg gaggcatggc tcataggttg agttgtaagg ctgacatgtt gtgcatctta   4800
ctcgcaatcg ctagttatgt ttgggtacct cttacctggt tgctttgtgt gtttccttgt   4860
tggttgcgct ggtcctcttt gcacccccctc accatcctgt ggttggtgtt tttcttgatt   4920
tctgtaaata taccctcggg aatcttggcc gtggtgttat tggtttctct ctggctttta   4980
ggtcgttata ctaacattgc tggtctcgtc accccttatg acattcatca ttacaccagt   5040
ggcccccgcg gtgtcgccgc cttggccacc gcgccagatg gaacctactt ggctgccgtc   5100
cgccgtgctg cgctgactgg tcgtaccatg ctgttcaccc cgtctcagct tgggtccctc   5160
cttgagggcg ctttcagaac tcaaaaaccc tcactgaaca ccgtcaatgt ggtcgggtcc   5220
tccatgggct ctggcggagt gttcactatt gacgggaaaa tcaagtgcgt gactgccgca   5280
catgtcctta cgggtaactc agctagggtt tccggggtcg gcttcaatca aatgcttgac   5340
tttgatgtaa aaggggactt cgccatagct gattgcccga attggcaagg ggttgctccc   5400
aaggcccagt tctgcgagga tgggtggact ggtcgcgcct attggctgac atcctctggc   5460
gttgaacccg gtgttattgg gaatgggttc gccttctgct tcaccgcgtg tggcgattct   5520
ggatccccag tgattaccga agccggtgag cttgtcggcg ttcacacagg atcaaacaaa   5580
caaggaggag gcattgtcac gcgcccctca ggccagtttt gtaatgtgaa gcccatcaag   5640
ctgagcgagt tgagtgaatt cttcgctgga cctaaggtcc cgctcggtga tgtgaaaatt   5700
ggcagtcaca taattaatga cacatgcgag gtgccttcag atctttgtgc cctgcttgct   5760
gccaaacccg aactggaagg aggcctttcc acagttcaac ttctgtgtgt gtttttcctc   5820
ctgtggagaa tgatggggca tgcctggacg cccttggttg ctgtggggtt tttcatcctg   5880
aatgagattc tcccagctgt tctggtccgg agtgttttct cctttgggat gtttgtgcta   5940
tcttggctca caccatggtc tgcgcaagtc ctgatgatca ggcttctgac agcagccctt   6000
aacagaaaca gatggtctct tggtttttac agccttggtg caataaccag ttttgtcgca   6060
gatcttgcgg taactcaagg gcatccgtta caggtggtaa tgaacttaag cacctatgcc   6120
ttcctgcccc ggatgatggt tgtgacctcg ccagtcccag tgatcgcgtg tggtgttgtg   6180
cacctccttg ccataatttt gtacttgttt aagtaccgct gccttcacaa tgtccttgtt   6240
ggcgatgggg tgttctcttc ggctttcttc ttgcgatact ttgccgaggg aaagttgagg   6300
gaaggggtgt cgcaatcctg tgggatgagt catgagtcgc tgactggtgc cctcgccatg   6360
agactcactg acgaggactt ggatttcctt acgaaatgga ctgattttaa gtgctttgtt   6420
tctgcgtcca acatgaggaa tgcagcgggc caatttatcg aggctgctta tgcaaaagca   6480
ctaagaattg aacttgctca gttggtacag gttgataagg tccgaggcac catggccaaa   6540
ctcgaggctt tcgccgatac cgtggcaccc caactctcgc ccggtgacat tgttgttgcc   6600
cttggccaca cgcctgttgg cagcatcttc gacctaaagg ttggtagcac caagcatact   6660
ctccaagcta ttgagactag agtccttgcc gggtccaaaa tgactgtggc gcgtgtcgtt   6720
gacccaaccc ccgcaccccc gcccgtacct gtgcccatcc ctctcccacc gaaagttctg   6780
gagaacggtc ccaatgcctg gggggatgag gaccgtttga acaagaagaa gaggcgcagg   6840
atggaagccg tcggcatttt tgtcatggac gggaaaaagt accagaaatt ttgggacaag   6900
aattccggtg atgtgtttta tgaggaggtc catattagca cagacgagtg ggagtgcctt   6960
agaactggcg accctgtcga ctttgatcct gagacaggga ttcagtgtgg gcatatcacc   7020
attgaagata aggtttacaa tgtcttcacc tccccatctg gtaggagatt cttggtcccc   7080
```

-continued gccaaccccg agaatagaag agctcagtgg gaagccgcca agctttccgt ggagcaagcc 7140
cttggtatga tgaacgtcga cggcgaactg actgccaaag aactggagaa actgaaaaga 7200
ataattgaca aactccaggg cctgactaag gagcagtgtt taaactgcta gccgccagcg 7260
gcctgacccg ctgtggtcgc ggcggcttag ttgttactga gacagcggta aaaatagtca 7320
aatttcacaa ccggaccttc accccaggac ctgtgaactt aaaagtggcc agtgaggttg 7380
agctaaaaga cgcggttgag cacaaccaac atccggttgc cagaccggtt gatggtggtg 7440
tcgtgctcct gcgctctgca gttccttcgc ttatagatgt cttgatctcc ggcgctgata 7500
catctcctaa gttactcgcc cgccacgggc cgggaaacac tgggattgat ggcacgcttt 7560
gggattttga ggccgaggct actaaagagg aagttgcact cagtgcgcaa ataatacagg 7620
cttgtgatat taggcgcggc gacgcacctg aaattggtct cccttataag ttgtaccctg 7680
ttaggggcaa ccctgagcgg gtaaaaggag ttttacagaa tacaaggttt ggagacatac 7740
cttacaaaac ccccagtgac actggaagcc cggtgcacgc ggctgcctgc ctcacgccta 7800
atgctactcc ggtgactgat gggcgctccg tcttggctac aaccatgccc tctggctttg 7860
agttgtatgt gccgaccatt ccagcgtccg tccttgatta tcttgattct aggcctgact 7920
gccctaaaca gttaacagag cacggttgtg aggatgctgc attaagagac ctctccaagt 7980
atgatttgtc cacccaaggc tttgttttgc ctggagttct tcgccttgtg cggaagtacc 8040
tgttcgccca cgtgggtaag tgcccgcccg ttcatcggcc ttccacttac cctgctaaga 8100
attctatggc tggaataaat gggaacaggt ttccaaccaa ggacattcag agcgtccctg 8160
aaatcgacgt tctgtgcgca caggctgtgc gagaaaactg gcaaactgtt accccttgta 8220
ccctcaagaa acagtactgt gggaagaaga agactaggac aatacttggc accaataact 8280
tcattgcgtt ggcccatcgg gcagcgttga gtggtgttac ccagggcttc atgaaaaaag 8340
cgttcaactc gcccatcgcc ctcgggaaaa acaaatttaa ggagctacaa gccccggtcc 8400
taggcaggtg ccttgaagct gatcttgcgt cctgcgatcg atccacacct gcaattgtcc 8460
gctggtttgc cgccaatctt ctttatgaac tcgcctgtgc tgaggagcat ctaccgtcgt 8520
acgtgctgaa ctgctgccac gacttactgg tcacgcagtc cggcgcggtg actaagagag 8580
gtggcctgtc gtctggcgac ccgattacct ctgtgtcaaa caccatttac agcttagtga 8640
tatatgcaca gcacatggtg ctcagttact tcaaaagtgc tcaccctcat ggccttctgt 8700
ttctgcaaga ccagctgaag tttgaggaca tgctcaaggt tcaacccctg accgtctatt 8760
cggacgacct tgtgctgtat gccgagtctc cctccatgcc aaactaccac tggtgggttg 8820
aacatctgaa ccttatgctg ggtttccaga cggacccaaa gaagacaacc atcacagact 8880
caccatcatt cctaggttgc aggataataa atgggcgcca gctggtccct aaccgtgaca 8940
ggatcctcgc ggccctcgcc taccacatga aggcgagcaa tgtttctgaa tactacgcct 9000
cggcggctgc aatactcatg gacagctgtg cttgtttgga gtatgatcct gaatggtttg 9060
aagagctcgt ggttgggata gcgcagtgcg cccgcaagga cggctacagc tttcctggcc 9120
caccgttctt cttgtccatg tgggaaaaac tcaggtccaa tcatgagggg aagaagtcca 9180
gaatgtgcgg gtactgcggg gccccggctc cgtacgccac tgcctgtggt ctcgatgtct 9240
gtgtttacca cacccacttc caccagcatt gtcctgttat aatctggtgt ggccacccgg 9300
cgggttctgg ttcttgtagt gagtgcgaac ccccccctagg aaaaggcaca agccctctag 9360
atgaggtgtt agaacaagtt ccgtacaagc ctccgcggac tgtgatcatg catgtggagc 9420
agggtctcac ccctcttgac ccaggtagat accagactcg ccgcggattg gtctccgtta 9480
ggcgtggcat caggggaaat gaagtcgacc taccagacgg tgattacgcc agtaccgcct 9540
tgctccctac ttgtaaagag atcaacatgg tcgctgtcgc ctctaacgtg ttgcgcagca 9600
ggtttatcat cggcccaccc ggtgctggga aaacacactg gcttcttcaa caagtccagg 9660
atggtgatgt catttacacg ccaactcacc agaccatgct cgacatgatt agggctttgg 9720
ggacgtgccg gttcaacgtt ccagcaggta caacgctgca attccctgcc ccctcccgta 9780
ccggcccatg ggttcgcatc ttggccggcg gttggtgtcc tggcaagaac tccttcctgg 9840
atgaagcggc gtattgcaat caccttgacg tcttgaggct tctcagtaaa acaactctca 9900
cttgcctagg ggacttcaaa caactccacc ctgtgggttt tgactcccat tgctatgtat 9960
ttgacatcat gcctcagacc caattaaaga ccatctggag gttcgggcag aatatctgtg 10020
atgccattca accagattac agggacaaac ttatggccat ggtcaacacg acccgtgtga 10080
cctacgtgga aaaacctgtc aggtacgggc aagtcctcac cccctaccac agggaccgag 10140
aggacggcgc cattactatc gactccagtc aaggcgccac atttgatgtg gttacactgc 10200
atttgcccac taaagattca ctcaacaggc aaagagctct tgttgctatc accagggcaa 10260
ggcatgctat cttcgtgtat gacccacaca ggcaattgca gagcatgttt gatcttcccg 10320
cgagaggcac acccgtcaac ctcgcagtgc accgtgacga acagctgatc gtattagaca 10380
gaaacaacag agaaatcacg gttgctcagg ctctaggcaa tggagataaa ttcagggcca 10440
cagataagcg cgttgtagat tctctccgcg ctatttgcgc agacctggaa gggtcgagct 10500
ccccgctccc caaggtcgcg cataacttgg gattccattt ctcacctgat ttgactcagt 10560
ttgctaaact cccggcagaa cttgcacccc actggcccgt ggtgacaacc cagaacaatg 10620
aaaggtggcc agatcggctg gtagccagcc tccgccctat ccataaatat agccgcgcgt 10680
gcattggtgc cggctatatg gtgggcccct cggtgttttt aggcacccct ggggttgtgt 10740
catactatct cacaaaattt gttagaggcg aggctcaagt gcttccggag acagtcttca 10800
gcaccggccg aattgaggta gattgtcgag agtatcttga tgatcgggag cgagaagttg 10860
ctgagtccct cccacatgcc ttcatcggcg atgtcaaagg taccaccgtt gggggatgtc 10920
atcacgttac ctccaaatac cttccgcgct tccttcccaa ggaatcagtt gcggtggtcg 10980
gggtttcgag ccccgggaaa gccgcgaaag cagtttgcac attgacggat gtgtacctcc 11040
cagaccttga agcgtacctc cacccagaga cccagtccag gtgctggaaa gtgatgttgg 11100
actttaagga ggttcgactg atggtatgga aagacaagac ggcctatttt caacttgaag 11160
gccgccattt tacctggtat caacttgcaa gctacgcctc atacatccga gttcctgtta 11220
attctactgt gtacttggac ccctgcatgg gccctgctct ttgcaacagg agggttgtcg 11280
ggtccaccca ttggggagct gacctcgcag tcacccctta tgattacggt gccaaaatta 11340
ttctgtctag tgcataccat ggtgaaatgc ctccaggtta caaaattctg gcgtgcgcgg 11400
agttctcgct tgatgatcca gtaaggtaca aacacacctg ggatttgaa tcggatacag 11460
cgtatctgta cgagtttact ggaaatggtg aggactggga ggattacaat gatgcgtttc 11520
gggcgcgcca gaaagggaaa atttataaag ctaatgccac cagcatgagg tttcattttc 11580
ccccgggccc tgtcattgaa ccaactttag gcctgaattg aaatgaaatg gggtctatgc 11640
aaagcctctt tgacaaaatt ggccaacttt ttgtggatgc tttcacggaa tttctggtgt 11700
ccattgttga tatcatcata tttttggcca ttttgtttgg cttcacaatc gccggttggc 11760
tggtggtctt atgcatcaga ctggtttgct ccgcggtact ccgtgcgcgc tctaccgttc 11820

-continued

```
accctgagca attacagaag atcttatgag gcctttcttt ctcagtgtca ggtagacatt  11880
cccacctggg gcgtcaaaca ccctttgggg gtgctttggc accataaggt gtcaaccctg  11940
attgatgaaa tggtgtcgcg tcgaatgtac cgcgtcatgg aaaaagcagg gcaggctgcc  12000
tggaaacagg tggtgagcga ggctacattg tctcgcatta gtggtttgga tgtggtggct  12060
cattttcaac atcttgccgc tattgaagcc gagacttgta aatatttggc ttcccggcta  12120
cccatgctgc acaacctgcg cttgacaggg tcaaatgtaa ccatagtgta taatagtact  12180
ttggatcagg tgtttgccat ttcccaacc cctggttccc ggccaaagct tcatgatttt  12240
cagcaatggc taatagctgt acattcctcc atattttcct ccgttgcagc ttcttgtact  12300
ctttttgttg tgctgtggtt gcgaattcca atgctacgtt ctgtttttgg tttccgctgg  12360
ttaggggcaa cttttctttt gaactcatgg tgaattacac ggtatgcccg ctttgcccaa  12420
cccggcaggc agccgccgag atccttgaac ccggcaagtc tttttggtgc aggatagggc  12480
atgaccgatg tagtgagaac gatcatgacg aactagggtt catggttccg cctggcctct  12540
ccagcgaagg ccacttgacc agtgtttacg cctggttggc gttcctgtcc ttcagctaca  12600
cggcccagtt ccatcccgag atatttggga tagggaatgt gagtcaagtt tatgttgaca  12660
tcaagcacca actcatctgc gctgttcatg acggggataa cgccaccttg cctcgccatg  12720
acaatatttc agccgtattt cagacctact accaacacca ggtcgacggc ggcaattggt  12780
ttcacctgga atggctacgc cctttctttt cctcttggtt ggttttaaat gtttcgtggt  12840
ttctcaggcg ttcgcctgca agccatgttt cagttcgagt ctttcggaca tcaaaaccaa  12900
caccaccgca gcatcaggct tcgttgtcct ccaggacatc agctgcctta ggcatggcga  12960
ctcgtcctct ccgacgattc gcaaaagttc tcagtgccgc acggcgatag ggacgcccgt  13020
gtacatcacc atcactgcca atgtcacaga tgaaaattat ctacattctt ctgatctcct  13080
catgctttct tcttgccttt tctatgcttc cgagatgagt gaaaagggat tcaaagtggt  13140
gtttggcaat gtgtcaggca tcgtggctgt gtgcgtcaac tttaccagct acgtccaaca  13200
cgtcaaggag tttacccaac gctccttagt ggtcgatcat gtgcgactgc ttcatttcat  13260
gacacctgag accatgaggt gggcaaccgt tttagcctgt ctttttgcca tccctactgg  13320
caatttgaat gttcaagtat gttggggaag tgcttgaccg cgtgctgttg ctcgcgattg  13380
cttttttgt ggtgtatcgt gccgtcctat cttgctgtgc tcgtcaacgc cagcaacaac  13440
aacagctctc atattcagtt gatttataac ttaacgctat gtgagctgaa tggcacagat  13500
tggctggcac aaaaatttga ctgggcagtg gagacttttg tcatcttccc cgtgttgact  13560
cacattgttt cctatgtggc actcaccacc agccatttcc ttgacacagt tggtctggcc  13620
actgtgtcca ccgccggata ttatcacggg cggtatgtct tgagtagcat ttacgcagtc  13680
tgtgctctgg ctgcgctgat ttgctttgtc attaggcttg cgaagaactg catgtcctgg  13740
cgctactctt gtaccagata taccaacttc cttctggaca ctaagggcaa actctatcgt  13800
tggcggtcgc ccgtcattgt ggagaaaggg ggtaaggttg aggtcgaagg tcacctgatc  13860
gacctcaaga gagttgtgct tgatggttcc gcggcaaccc ctttaaccag agtttcagcg  13920
gaacgatggg gtcgtctcta gacgacttct gcaatgatag cacagctcca cagaaggtgc  13980
ttttggcgtt ttccattacc tacacgccag tgatgatata tgctctaaag gtaagtcgcg  14040
gccgactgct agggcttctg caccttttga tctttctgaa ttgtgctttt accttcgggt  14100
acatgacatt cgtgcacttt gagagcacaa atagggtcgc gctcactatg ggagcagtag  14160
ttgcacttct ttggggagtg tactcagcca tagaaacctg gaaattcatc acctccagat  14220
```

gccgtttgtg cttgctaggc cgcaagtaca ttctggcccc tgcccaccac gtcgaaagtg 14280
ccgcgggctt tcatccgatt gcggcaaatg ataaccacgc atttgtcgtc cggcgtcccg 14340
gctccactac ggtcaacggc acattggtgc ccgggttgaa aagcctcgtg ttgggtggca 14400
gaaaagctgt taagcaggga gtggtaaacc ttgttaaata tgccaaataa caacggcaag 14460
cagcaaaaga aaaagaaggg gaatggccag ccagtcaatc agctgtgcca aatgctgggt 14520
aagatcatcg cccaacaaaa ccagtccaga ggcaagggac cggggaagaa aaataggaag 14580
aaaaacccgg ggaagcccca tttccctcta gcgactgaag atgacgtcag gcatcacttt 14640
acccctagtg agcggcaatt gtgtctgtcg tcgatccaga ctgccttcaa tcagggtgct 14700
ggaacttgtg ccctgtcaga ttcagggagg ataagttaca ctgtggagtt tagtttgccg 14760
acgcaacata ctgtgcgtct gatccgcgcc acagcatcac cctcagcatg atgggctggc 14820
attctttggc acctcagtgt tagaattggg agaatgtgtg gtgaatggca ctgattgaca 14880
ctgtgcctct aagtcaccta ttcaattagg gcgaccgtgt gggggtaaag tttaattggc 14940
gagaaccatg cggccgtaat taaaaa 14966

<210> SEQ ID NO 4
<211> LENGTH: 2850
<212> TYPE: DNA
<213> ORGANISM: Porcine reproductive and respiratory syndrome virus

<400> SEQUENCE: 4
gccggaaaga gagcaaggaa accgcgctct ggtgcgacta ctatggtcgc tcatcacgct 60
tcgtccgctc atgaaacccg gcaggccacg aagcacgagg gtgccggcgc taacaaggct 120
gagcatctca agcgctactc tccgcctgcc gaagggaact gtggttggca ctgcatttcc 180
gccatcgcca accggatggt gaattccaac tttgagacca cccttcctga aagagtaagg 240
ccttcagatg actgggccac tgacgaggat cttgtgaaca ccatccaaat cctcaggctc 300
cctgcggcct tggacaggaa cggcgcttgc ggtagcgcca agtacgtgct taaactggag 360
ggtgagcatt ggactgtctc tgtgatccct gggatgtccc ctactttgct ccccccttgaa 420 tgtgttcagg gttgttgtga gcataagggc ggtcttgttt ccccggatgc ggtcgaaatt 480
tccggatttg atcctgcctg ccttgaccga ctggctaagg taatgcactt gcctagcagt 540
accatcccag ccgctctggc cgaattgtcc gacgactcca accgtccggt ttccccggcc 600
gctactacgt ggactgtttc gcaattctat gctcgtcata gaggaggaga tcatcatgac 660
caggtgtgct tagggaaaat catcagcctt tgtcaagtta ttgaggattg ctgctgccat 720
cagaataaaa ccaaccgggc tactccggaa gaggtcgcgg caaagattga tcagtacctc 780
cgtggcgcaa caagtcttga ggaatgcttg gccaaacttg agagagtttc cccgccgagc 840
gctgcggaca cctcctttga ttggaatgtt gtgcttcctg ggggttgaggc ggcgaatcag 900 acaaccgaac aacctcacgt caactcatgc tgcaccctag tccctcccgt gactcaagag 960
cctttgggca aggactcggt ccctctgacc gccttctcac tgtccaattg ctattaccct 1020
gcacaaggtg acgaggttca tcaccgtgag aggttaaatt ccgtactctc taagttggaa 1080
gaggttgtcc tggaagaata tgggctcatg tccactggac ttggcccgcg acccgtgctg 1140
ccgagcgggc tcgacgagct taaagaccag atggaggagg atctgctaaa actagccaac 1200
acccaggcga cttcagaaat gatggcctgg gcggctgagc aggtcgattt aaaagcttgg 1260
gtcaaaagct acccgcggtg gacaccacca cccccaccac caagagttca acctcgaaga 1320
acaaagtctg tcaaaagctt gccagagggc aagcctgtcc ctgctccgcg caggaaggtc 1380
agatccgatt gcggcagccc ggttttgatg ggcgacaatg tccctaacgg ttcggaagaa 1440
actgtcggtg gtcccctcaa tcttccgaca ccatccgagc cgatgacacc tatgagtgag 1500
cccgtacttg tgccagcgtc gcgacgtgtc cccaagctga tgacaccttt gagtgggtcg 1560
gcaccagttc ctgcaccgcg tagaactgta acaacaacgc tgacgcacca ggatgagcct 1620
ctggatttgt ctgcgtcctc acagacggaa tatgaggctt tcccccctagc accatcgcag 1680 aacatgggta tcctggaggc gggggggcaa gaagttgagg aagtcctgag tgaaatctcg 1740
gatatactaa atgacaccaa ccctgcacct gtgtcatcaa gcagctccct gtcaagtgtt 1800
aagatcacac gcccaaaata ctcagctcaa gccatcatcg actctggcgg gccttgcagt 1860
gggcatctcc aaaaggaaaa agaagcatgc ctcagcatca tgcgtgaggc ttgtgatgcg 1920
tccaagcttg gtgatcctgc tacgcaggag tggctctctc gcatgtggga tagggttgac 1980
atgctgactt ggcgcaacac gtctgcttac caggcgtttc gcatcttaaa tggcaggttt 2040
gagtttctcc caaagatgat tctcgagaca ccgccgcccc acccgtgcgg gtttgtgatg 2100
ttacctcgca cgcctgcacc ttccgtgagt gcagagagtg acctcaccat tggttcagtg 2160
gccaccgagg atgttccacg catcctcggg aaaataggag acaccgacga gctgcttgac 2220
cggggtccct cggcaccctc caagggagaa ccggtctgtg accaacctgc caaagatccc 2280
cggatgtcgc cgcgggagtc tgacgagagc atgatagctc cgcccgcaga tacaggtggt 2340
gtcggctcat tcactgattt gccgtcttca gatggtgtgg atgtggacgg ggggggggccg 2400 ttaagaacgg taaaaacaaa agcaggaagg ctcttagacc aactgagctg ccaggttttt 2460
agcctcgttt cccatctccc tattttcttc tcacacctct tcaaatctga cagtggttat 2520
tctccgggtg attggggttt tgcagctttt actctatttt gcctctttct atgttacagt 2580
tacccattct tcggttttgc tcccctcttg ggtgtatttt ctgggtcttc tcggcgtgtg 2640
cgaatggggg tttttggctg ctggttggct tttgctgttg gtctgttcaa gcctgtgtcc 2700
gacccagtcg gcactgcttg tgagtttgac tcgccagagt gtaggaacgt ccttcattct 2760
tttgagcttc tcaaaccttg ggaccctgtc cgcagccttg ttgtgggccc cgtcggtctc 2820
ggccttgcca ttcttggcag gttactgggc 2850

<210> SEQ ID NO 5
<211> LENGTH: 2940
<212> TYPE: DNA
<213> ORGANISM: Porcine reproductive and respiratory syndrome virus

<400> SEQUENCE: 5
gctggaaaga gagcaagaaa agcacgctct tgtgcgactg ctacagtcgc tggccgcgct 60
ttgtccgttc gtgaaacccg gcaggccaag gagcacgagg ttgccggcgc caacaaggct 120
gagcacctca aacactactc cccgcctgcc gaagggaatt gtggttggca ctgcatttcc 180
gccatcgcca accggatggt gaattccaaa tttgaaacca cccttcccga aagagtgaga 240
cctccagatg actgggctac tgacgaggat cttgtgaatg ccatccaaat cctcagactc 300
cctgcggcct tagacaggaa cggtgcttgt actagcgcca agtacgtact taagctggaa 360
ggtgagcatt ggactgtcac tgtgacccct gggatgtccc cttctttgct ccctcttgaa 420
tgtgttcagg gctgttgtgg gcacaagggc ggtcttggtt ccccagatgc agtcgaggtc 480
tccggatttg accctgcctg ccttgaccgg ctggctgagg tgatgcacct gcctagcagt 540
gctatcccag ccgctctggc cgaaatgtct ggcgattccg atcgttcggc ttctccggtc 600

-continued

```
accaccgtgt ggactgtttc gcagttcttt gcccgtcaca gcggagggaa tcaccctgac    660
caagtgcgct tagggaaaat tatcagcctt tgtcaggtga ttgaggactg ctgctgttcc    720
cagaacaaaa ccaaccgggt caccccggag gaggtcgcag caaagattga cctgtacctc    780
cgtggtgcaa caaatcttga agaatgcttg gccaggcttg agaaagcgcg cccgccacgc    840
gtaatcgaca cctcctttga ttgggatgtt gtgctccctg ggttgaggc ggcaacccag    900
acgatcaagc tgccccaggt caaccagtgt cgtgctctgg tccctgttgt gactcaaaag    960
tccttggaca acaactcggt cccccctgacc gcctttcac tggctaacta ctactaccgt   1020
gcgcaaggtg acgaagttcg tcaccgtgaa agactaaccg ccgtgctctc caagttggaa   1080
aaggttgttc gagaagaata tgggctcatg ccaaccgagc ctggtccacg gcccacactg   1140
ccacgcgggc tcgacgaact caaagaccag atggaggagg acttgctgaa actggctaac   1200
gcccagacga cttcggacat gatggcctgg gcagtcgagc aggttgacct aaaaacttgg   1260
gtcaagaact acccgcggtg gacaccacca cccccctccgc caaaagttca gcctcgaaaa   1320
acgaagcctg tcaagagctt gccggagaga aagcctgtcc ccgccccgcg caggaaggtt   1380
gggtccgatt gtggcagccc ggtttcatta ggcggcgatg tccctaacag ttgggaagat   1440
ttggctgtta gtagcccctt tgatctcccg accccacctg agccggcaac accttcaagt   1500
gagctggtga ttgtgtcctc accgcaatgc atcttcaggc cggcgacacc cttgagtgag   1560
ccggctccaa ttcccgcacc tcgcggaact gtgtctcgac cggtgacacc cttgagtgag   1620
ccgatccctg tgcccgcacc gcggcgtaag tttcagcagg tgaaaagatt gagttcggcg   1680
gcggcaatcc caccgtacca ggacgagccc ctggatttgt ctgcttcctc acagactgaa   1740
tatgaggcct ctcccccagc accgccgcag agcgggggcg ttctgggagt agaggggcat   1800
gaagctgagg aaaccctgag tgaaatctcg gacatgtcgg gtaacattaa acctgcgtcc   1860
gtgtcatcaa gcagctcctt gtccagcgtg agaatcacac gcccaaaata ctcagctcaa   1920
gccatcatcg actcgggcgg gccctgcagt gggcatctcc aagaggtaaa ggaaacatgc   1980
cttagtgtca tgcgcgaggc atgtgatgcg actaagcttg atgaccctgc tacgcaggaa   2040
tggctttctc gcatgtggga tcgggtggac atgctgactt ggcgcaacac gtctgtttac   2100
caggcgattt gcaccttaga tggcaggtta aagttcctcc caaaaatgat actcgagaca   2160
ccgccgccct atccgtgtga gtttgtgatg atgcctcaca cgcctgcacc ttccgtaggt   2220
gcggagagcg accttaccat tggctcagtt gctactgaag atgttccacg catcctcgag   2280
aaaatagaaa atgtcggcga gatggccaac cagggaccct tggccttctc cgaggataaa   2340
ccggtagatg accaacttgt caacgacccc cggatatcgt cgcggaggcc tgacgagagc   2400
acatcagctc cgtccgcagg cacaggtggc gccggctctt ttaccgattt gccgccttca   2460
gatggcgcgg atgcggacgg gggggggccg tttcggacgg taaaaagaaa agctgaaagg   2520
ctctttgacc aactgagccg tcaggttttt gacctcgtct cccatctccc tgttttcttc   2580
tcacgccttt tctaccctgg cggtggttat tctccgggtg attggggttt tgcagctttt   2640
actctattgt gcctcttttt atgttacagt tacccagcct ttggtattgc tcccctcttg   2700
ggtgtgtttt ctgggtcttc tcggcgcgtt cgaatggggg tttttggctg ctggttggct   2760
tttgctgttg gtctgttcaa gcctgtgtcc gacccagtcg gcgctgcttg tgagtttgac   2820
tcgccagagt gtagaaacat ccttcattct tttgagcttc tcaaaccttg ggaccctgtt   2880
cgcagccttg ttgtgggccc cgtcggtctc ggtcttgcca ttcttggcag gttactgggc   2940
```

```
<210> SEQ ID NO 6
<211> LENGTH: 241
<212> TYPE: DNA
<213> ORGANISM: Porcine reproductive and respiratory syndrome virus

<400> SEQUENCE: 6

tttggctgtt agtagcccct ttgatctccc gaccccacct gagccggcaa caccttcaag     60

tgagctggtg attgtgtcct caccgcaatg catcttcagg ccggcgacac ccttgagtga    120

gccggctcca attcccgcac ctcgcggaac tgtgtctcga ccggtgacac ccttgagtga    180

gccgatccct gtgcccgcac cgcggcgtaa gtttcagcag gtgaaaagat tgagttcggc    240

g                                                                     241


<210> SEQ ID NO 7
<211> LENGTH: 87
<212> TYPE: DNA
<213> ORGANISM: Porcine reproductive and respiratory syndrome virus

<400> SEQUENCE: 7

cccttgagtg agccgatccc tgtgcccgca ccgcggcgta agtttcagca ggtgaaaaga     60

ttgagttcgg cggcggcaat cccaccg                                         87


<210> SEQ ID NO 8
<211> LENGTH: 360
<212> TYPE: DNA
<213> ORGANISM: Porcine reproductive and respiratory syndrome virus

<400> SEQUENCE: 8

tcaagtgtta agatcacacg cccaaaatac tcagctcaag ccatcatcga ctctggcggg     60

ccttgcagtg ggcatctcca aaaggaaaaa gaagcatgcc tcagcatcat gcgtgaggct    120

tgtgatgcgt ccaagcttgg tgatcctgct acgcaggagt ggctctctcg catgtgggat    180

agggttgaca tgctgacttg gcgcaacacg tctgcttacc aggcgtttcg catcttaaat    240

ggcaggtttg agtttctccc aaagatgatt ctcgagacac cgccgcccca cccgtgcggg    300

tttgtgatgt tacctcgcac gcctgcacct tccgtgagtg cagagagtga cctcaccatt    360


<210> SEQ ID NO 9
<211> LENGTH: 120
<212> TYPE: PRT
<213> ORGANISM: Porcine reproductive and respiratory syndrome virus

<400> SEQUENCE: 9

Ser Ser Val Lys Ile Thr Arg Pro Lys Tyr Ser Ala Gln Ala Ile Ile
1               5                   10                  15

Asp Ser Gly Gly Pro Cys Ser Gly His Leu Gln Lys Glu Lys Glu Ala
            20                  25                  30

Cys Leu Ser Ile Met Arg Glu Ala Cys Asp Ala Ser Lys Leu Gly Asp
        35                  40                  45

Pro Ala Thr Gln Glu Trp Leu Ser Arg Met Trp Asp Arg Val Asp Met
    50                  55                  60

Leu Thr Trp Arg Asn Thr Ser Ala Tyr Gln Ala Phe Arg Ile Leu Asn
65                  70                  75                  80

Gly Arg Phe Glu Phe Leu Pro Lys Met Ile Leu Glu Thr Pro Pro Pro
                85                  90                  95

His Pro Cys Gly Phe Val Met Leu Pro Arg Thr Pro Ala Pro Ser Val
            100                 105                 110
```

```
Ser Ala Glu Ser Asp Leu Thr Ile
        115                 120


<210> SEQ ID NO 10
<211> LENGTH: 12310
<212> TYPE: DNA
<213> ORGANISM: Classical Swine Fever Virus

<400> SEQUENCE: 10

gtatacgagg ttagttcatt ctcgtataca cgattggaca aatcaaaatt ataatttggt     60

tcagggcctc cctccagcga cggccgaact gggctagcca tgcccatagt aggactagca    120

aaacggaggg actagccata gtggcgagct ccctgggtgg tctaagtcct gagtacagga    180

cagtcgtcag tagttcgacg tgagcagaag cccacctcga gatgctacgt ggacgagggc    240

atgcccaaga cacaccttaa ccctagcggg ggtcgctagg gtgaaatcac accacgtgat    300

gggagtacga cctgataggg cgctgcagag gcccactatt aggctagtat aaaaatctct    360

gctgtacatg gcacatggag ttgaatcact ttgaactttt atacaaaaca aacaaacaaa    420

aaccaatggg agtggaggaa ccggtgtacg atgccacggg gagaccattg ttcggagacc    480

cgagtgaggt acacccacaa tcaacactga agctaccaca tgataggggt agaggcaaca    540

ttaaaacaac actgaagaac ctacctagga aaggcgactg caggagcggc aaccatctag    600

gcccggtcag tgggatatat gtaaaacccg gccctgtctt ttaccaggac tacatgggcc    660

cggtctacca tagagcccct ctggagtttt ttgacgaagt gcagttctgc gaggtgacca    720

aaaggatagg tagggtgaca ggtagcgacg gaaagcttta ccatacatat gtgtgcatcg    780

atggctgcat actgctgaag ctggccaaga ggggtgagcc aagaaccctg aagtggatta    840

gaaatttcac cgactgtcca ttgtgggtta ccagttgctc cgatgatggc gcaagtggga    900

gtaaagagaa gaagccagat aggatcaaca aaggcaaatt aaaaatagcc ccaaaagagc    960

atgagaagga cagcagaact aggccacctg acgctacgat cgtggtggaa ggagtaaaat   1020

accaggtcaa aaagaaaggt aaagttaaag gaaagaatac ccaagacggc ctgtaccaca   1080

acaagaataa accaccagaa tccaggaaga aattagaaaa agccctattg gcatgggcgg   1140

tgatagcaat tatgttgtac caaccagttg aagccgaaaa tataactcaa tggaacctga   1200

gtgacaacgg cactaatggt atccagcatg ctatgtacct tagaggggtt aacagaagct   1260

tgcatgggat ctggccgggg aaaatatgca aaggagtccc aacccacctg gccacagacg   1320

tggagctgaa agaaatacag ggaatgatgg atgccagcga ggggacaaac tatacgtgct   1380

gtaagttaca gagacatgaa tggaacaaac atggatggtg taactggcac aatatagacc   1440

cctggataca gctgatgaat agaacccaag cagacttggc agaaggccct ccggtcaagg   1500

agtgcgctgt gacttgcagg tacgataaag atgctgacat caacgtggtc acccaggcta   1560

gaaacaggcc aacaaccctg accggctgca agaaagggaa aaatttttct tttgcgggta   1620

cagttataga gagcccatgt aatttcaatg tttccgtgga ggataccttg tatggggatc   1680

atgagtgcgg cagtttactc caggacgcag ctctgtacct agtagatgga atgaccaaca   1740

ctatagagaa tgccagacag ggagcagcga gggtgacatc ttggctcggg aggcaactca   1800

gcactgctgg gaagaggttg gagggtagaa gcaaaacctg gtttggcgct tatgccctat   1860

cgccttactg taatgtaaca agcaagatag ggtacatatg gtacactaac aactgcaccc   1920

cagcttgcct ccccaaaaac acaaagataa taggccctgg taaatttgac accaatgcag   1980

aagacggaaa gattctccat gagatggggg gccacctatc agaatttctg ctgctttctc   2040
```

-continued

```
tggttgttct gtctgacttc gcccctgaaa cagccagcgc gttatacctc attttgcact   2100
acgtgattcc tcaaccccat gatgaacctg aaggctgcga tacgaaccag ctgaatctaa   2160
cagtagaact caggactgaa gacgtaatac cgtcatcagt ctggaatgtt ggtgaatatg   2220
tgtgtattag accagactgg tggccatatg aaaccgaggt ggctctgtta tttgaagagg   2280
caggacaggt cgtaaagtta gtcttacggg cgctgaggga tttgactagg gtctggaata   2340
gcgcatcaac cattgcattc ctcatctgct tgataaaagt attaagggga cagatcgtgc   2400
aaggtgtggt atggctgtta ctagtaactg gggcacaagg ccggctagcc tgcaaggaag   2460
attacaggta cgcaatatcg tcaaccgatg agatagggct acttggggcc ggaggtctca   2520
ccaccacctg gaaggaatac aaccacgatt tgcaactgaa tgacgggacc gtcaaggcca   2580
gttgcgtggc aggttccttt aaagtcacag cacttaatgt ggtcagtagg aggtatttgg   2640
cgtcattgca taagaaggct ttacccactt ccgtgacatt cgagctcctg ttcgacggga   2700
ccaacccatc aactgaggaa atgggagatg acttcaggtc cgggctgtgc ccgtttgata   2760
cgagtcctgt tgttaaggga aagtacaata cgaccttgtt gaacggtagt gctttctatc   2820
ttgtctgccc aatagggtgg acgggtgtca tagagtgcac agcagtgagc ccaacaactc   2880
tgaggacaga agtggtaaag accttcagga gagacaagcc ctttccgcac agaatggatt   2940
gtgtgaccac cacagtggaa aatgaagatt tattctattg taagttgggg ggcaactgga   3000
catgtgtgaa aggcgagcca gtggtctaca cagggggggt agtaaaacaa tgtagatggt   3060
gtggcttcga cttcgatggg cctgacggac tcccgcatta ccccataggt aagtgcattt   3120
tggcaaatga gacaggttac agaatagtag attcaacgga ctgtaacaga gatggcgttg   3180
taatcagcac agaggggagt catgagtgct tgatcggtaa cacgactgtc aaggtgcatg   3240
catcagatga aagactgggc cctatgccat gcagacctaa agagattgtc tctagtgctg   3300
gtcctgtaat gaaaacctcc tgtacattca actacacaaa aactttgaag aacaggtact   3360
atgagcccag ggacagctac ttccagcaat atatgcttaa gggtgagtat cagtactggt   3420
ttgacctgga tgcgactgac cgccactcag attacttcgc agaatttgtt gtcttggtgg   3480
tggtagcact gttaggagga agatatgtcc tgtggctgat agtgacctac gtagttctaa   3540
cagaacaact cgccgctggt ttaccattgg gccagggtga ggtagtgttg atagggaact   3600
taatcaccca cacagacatt gaggtcgtag tatatttttt actactctat ttggtcatga   3660
gggatgaacc tataaagaaa tggatactgc tgctgttcca tgctatgact aacaatccag   3720
tcaagaccat aacagtggca ttgctcatgg ttagtggagt tgccaagggt ggaaagatag   3780
atggcggttg gcagcgactg ccggggacca gctttgacat ccaactcgcg ctgacagtta   3840
tagtagtcgc tgtgatgttg ctggcaaaga gagatccgac tacggtcccc ttggttataa   3900
cagtggcgac cctgagaaca gctaagatga ctaacggact tagtacggat atagccatag   3960
ccacagtgtc agcagcgttg ctaacctgga cctacattag tgactattac agatacaaga   4020
cctggctaca gtaccttatc agcacagtga caggtatctt tttaataagg gtactgaagg   4080
gaataggtga gttggattta cacactccga ccttgccatc tcatagaccc ctctttttca   4140
ttctcgtgta ccttatttcc actgcagtgg taacgagatg gaatctggac atagctggat   4200
tgctgttgca gtgtgttcca acccttttga tggtttttac gatgtgggca gacattctca   4260
ccctgatcct catactgccc acttacgagt taacgaagct atattatctt aaggaagtga   4320
agattggggc agaaaagggc tggttatgga agaccaactt caagagggta aacgacatat   4380
acgaagttga ccaagctggt gaaggggtat acctattccc gtcaaaacaa aagacaagtt   4440
```

caatgacagg caccatgttg ccattgatca aagccatact tatcagctgc gtcagtaata 4500
agtggcagtt catatatcta ctgtacttga tatttgaagt atcttactac ctccacaaga 4560
agatcataga tgaaatagca ggagggacca acttcatctc aagacttgta gccgctttga 4620
tcgaagtcaa ttgggccttt gacaacgaag aagttagggg tttgaagaag ttcttcctgt 4680
tgtctagtag ggttaaagaa ctgatcatca aacacaaagt gaggaatgaa gtaatggtcc 4740
gctggtttgg tgacgaagag gtctatggga tgccgaagtt ggttggccta gtcaaggcag 4800
caacattgag taaaaataaa cattgtattt tgtgcaccgt ctgtgaagac agagagtgga 4860
gaggagaaac ctgcccaaaa tgcgggcgtt ttgggccacc aatgacctgt ggcatgaccc 4920
tagccgactt tgaagagaaa cactataaga ggatcttttt tagagaggat caatcagaag 4980
ggccggttag ggaggagtac gcagggtatc tgcaatatag agccagaggg caattgttcc 5040
tgaggaatct cccagtgcta gcaacaaaag ttaagatgct cctggtcggc aatcttggga 5100
cggaggtggg agatttggaa caccttggct gggtgctcag agggcctgcc gtttgcaaga 5160
aggtcactga acatgagaaa tgtaccacat ccatgatgga caaattgact gctttttttcg 5220 gtgttatgcc gaggggcacc acacctagag cccctgtgag attccctacc tctctcttaa 5280
agataagaag ggtttggaa actggctggg cgtacacaca ccaaggtggc atcagttcag 5340
tggaccatgt cacttgtgga aaagacttac tggtatgtga cactatgggc cggacaaggg 5400
ttgtttgcca gtcaaataat aagatgacag atgagtccga gtatggagtt aaaactgatt 5460
ccggatgccc ggaaggagct aggtgttatg tgttcaaccc agaggcagtt aacatatcag 5520
ggactaaagg agccatggtc cacttacaaa aaactggagg agaattcacc tgtgtgacag 5580
catcaggaac tccggctttc tttgatctta aaaaccttaa aggctggtca gggctaccga 5640
tatttgaggc atcaagtgga agggtagtcg gcagggtcaa ggtcggtaag aatgaggact 5700
ctaaaccaac caagcttatg agtggaatac aaacagtttc caaaagtacc acagacttga 5760
cagaaatggt aaagaaaata acgaccatga gcaggggaga attcagacaa ataacccttg 5820
ctacaggtgc cggaaaaacc acggaactcc ctaggtcagt catagaagag atagggaggc 5880
ataagagagt cttggtcttg atccctctga gggcggcagc agagtcagta taccaatata 5940
tgagacaaaa gcatccaagc atcgcattta acctgaggat aggggagatg aaggaagggg 6000
acatggccac agggataact tatgcttcat acggttactt ctgtcagatg ccacaaccta 6060
agttgcgagc cgcaatggtt gagtactcct tcatattcct tgatgagtac cactgtgcca 6120
cccctgaaca attggctatc atgggaaaga ttcacagatt ttcagagaac ctgcgggtgg 6180
tggccatgac cgcaacacca gtaggcacgg taacgaccac agggcagaaa caccctatag 6240
aagaattcat agccccagat gtgatgaaag gggaagactt aggttcagag tacttggaca 6300
ttgctggact aaagatacca gtagaggaga tgaagagcaa tatgctggtt tttgtgccca 6360
ccaggaacat ggcagtggag acagcaaaga aattgaaagc taagggttat aactcaggct 6420
actattatag tggtgaggat ccatctaacc tgagggtggt aacatcgcag tccccgtacg 6480
tggtggtggc aaccaacgcg atagaatcag gtgttactct cccggacttg gatgtggttg 6540
tcgatacagg gcttaagtgt gaaaagagaa tacggctgtc acctaagatg cctttcatag 6600
tgacgggcct gaagagaatg gctgtcacga ttggggaaca agcccagaga agggggagag 6660
ttgggagagt aaagcctgga agatactaca ggagtcaaga aacccccgtt ggttctaaag 6720
attaccatta tgatttactg caagcacaga ggtacggtat tgaagatggg ataaacatca 6780

```
ccaaatcctt tagagagatg aactatgatt ggagccttta tgaggaggac agtctgatga   6840
ttacacaatt ggaaattctt aataatttgt tgatatcaga tgaactacca atggcagtaa   6900
aaaatataat ggccaggact gaccacccag aaccaattca gctggcgtac aacagctacg   6960
aaacacaagt gccagtgcta ttcccaaaaa taaagaatgg agaggtgact gacagttacg   7020
ataactatac cttcctcaac gcaagaaaat taggggatga tgtacccccct tacgtgtatg   7080
ccacagagga tgaggactta gcggtagagc tgctgggctt agactggccg gaccctggaa   7140
accaagggac cgtagagact ggcagagcac taaaacaggt agttggtcta tcaacagctg   7200
agaatgccct gttagtagcc ttattcggct acgtaggata tcaggcgctt tcaaagaggc   7260
atataccagt agtcacagac atatactcaa ttgaagatca caggttggaa gacaccacac   7320
acctacagta cgccccaaat gctatcaaga cggaggggaa ggagacagaa ttgaaggagc   7380
tagctcaggg ggatgtgcag agatgtgtgg aagccatgac caattatgca agagagggta   7440
tccaatttat gaagtctcag gcactgaagg tgaaggaaac ccctacttac aaggagacaa   7500
tggacactgt gacggactat gtaaagaaat tcatggaggc gctggcagac agtaaagaag   7560
acatcataaa atatgggctg tgggggacgc acacagcctt atataagagc atcagtgcca   7620
ggcttggggg tgagactgcg ttcgctaccc tggtagtgaa gtggctggca tttgggggtg   7680
aatcaatagc agaccatgtc aaacaagcgg ccacagactt ggtcgtttac tatatcatca   7740
acagacctca gttcccagga gacacggaga cacaacaaga cggaaggaaa tttgtggcca   7800
gcctactggc ctcagctcta gctacttaca catacaaaag ctggaattac aataacctgt   7860
ccaagatagt tgaaccggct ttggccactc tgccctatgc cgccacagct ctcaaattat   7920
ttgcccccac ccgattagag agcgttgtca tattaagtac cgcaatctac aagacctacc   7980
tatcaatcag gcgcggaaaa agcgatggtt tgctaggcac gggggttagt gcggctatgg   8040
agatcatgtc acaaaatcca gtatccgtgg gcatagcagt catgctaggg gtaggggccg   8100
tggcagccca caatgcaatc gaagccagtg agcagaaaag aacactactc atgaaagtct   8160
ttgtaaagaa cttcttggac caggcagcca cagatgaatt agtcaaggag agtcctgaga   8220
aaataataat ggctttgttt gaggcagtgc agacagtcgg caaccctctt agacttgtat   8280
accaccttta tggagttttt tataaggggt gggaggcaaa agagttggcc caaaggacag   8340
ccggtaggaa ccttttcact ttaataatgt tcgaggctgt ggaactgctg ggagtagaca   8400
gtgaaggaaa ggtccgccag ctatcaagta attacatact agagcttttg tataagttcc   8460
gtgacagtat caagtctagc gtgagggaga tggcaatcag ctgggcccct gccccttca   8520
gttgtgattg gacaccgacg gatgacagaa tagggctccc ccaagacaac ttccaccaag   8580
tggagacgaa atgcccctgt ggttacaaga tgaaggcagt taagaattgt gctggagaac   8640
tgagactctt ggaggaggaa ggttcatttc tctgcagaaa taaattcggg agaggttcac   8700
ggaactacag ggtgacaaaa tattatgatg acaacctatt agaaataaag ccagtgataa   8760
gaatggaagg gcatgtggaa ctctactaca agggggccac catcaaactg gatttcaaca   8820
acagcaaaac aatattggca accgataaat gggaggttga tcactccact ctggtcaggg   8880
tgctcaagag gcacacaggg gctggatatc atggggcata cctgggcgaa aaaccgaacc   8940
acaaacacct gatagagagg gactgtgcaa ccatcaccaa agataaggtc tgttttctca   9000
aaatgaagag agggtgcgca tttacttatg acttatccct tcacaacctt acccgactga   9060
ttgaattggt acacaagaat aacttggaag acaaagagat tcccgctgct acggttacaa   9120
cctggctggc ttacacattt gtaaatgagg atatagggac cataaaacca gccttcgggg   9180
```

agaaagtaac gctggagatg caggaggaga taaccttgca gcctgccgtt gtggtggata 9240
caacagacgt agccgtgact gtggtagggg aagcccccac tatgactaca ggggagacac 9300
cgacagtgtt cgccagctca ggttcaggcc tgaaaagcca acaagttttg aaactagggg 9360
taggtgaagg ccaatatcca gggactaatc cacagagggc aagcctgcac gaagccatac 9420
aaggtgcaga tgagaggccc tcggtgctga tattggggtc tgataaagcc acctctaata 9480
gagtgaagac tgcaaagaat gtaaaggtat acagaggcag ggacccacta gaagtgagag 9540
atatgatgag gaggggaaag atcctggtcg tagccctgtc tagggttgat aatgctctat 9600
tgaaatttgt tgactacaaa ggcacctttc taactaggga ggctctagag gcattaagtt 9660
tgggcaggcc taaaaagaaa aacataacca aggcagaagc gcagtggttg ctgtgccccg 9720
aggaccaaat ggaagagcta cccgactggt tcgcagccgg ggaacccata tttttagagg 9780
ccaacattaa acatgacagg taccatctgg tggggggatat agctaccatc aaggaaaaag 9840
ccaaacagtt gggggctaca gactccacaa agatatctaa ggaggttggt gccaaagtgt 9900
attctatgaa actgagtaat tgggtgatgc aagaagaaaa taaacagggc aacctgaccc 9960
ccttgtttga agagctcctg caacagtgtc cacccggggg ccagaacaaa accgcacaca 10020
tggtctctgc ttaccaactg gctcaaggga actggatgcc gaccagctgc catgttttca 10080
tggggaccat atctgccagg agaaccaaga cccacccata tgaagcatac gtaaagttaa 10140
gggagttggt agaggaacac aagatgaaaa cactgtgtcc cggatcaagc ctgggtaagc 10200
acaacgattg gataattgga aaaattaaat accagggaaa cctgaggacc aaacacatgt 10260
tgaaccccgg caaggtggca gagcaactgt gcagagaggg acacagacac aatgtgtata 10320
acaagacaat aagctcagta atgacagcta ctggtatcag gttggagaag ttgcccgtgg 10380
ttagggccca gacagaccca accaacttcc accaagcaat aagggataag atagacaagg 10440
aagagaacct acaaaccccg ggtttacata agaaattaat ggaagttttc aacgcattga 10500
aacgacccga gttagagtcc tcctacgacg ccgtggaatg ggaggaactg gagagaggaa 10560
taaacaggaa gggtgctgct ggtttttttcg aacgcaaaaa tataggggaa atattggatt 10620
cagagaaaaa taaagtcgaa gagattattg acaatctgaa aaaaggtaga aacattaaat 10680
attatgaaac cgcgatccca aagaatgaga agagggacgt caacgatgac tggaccgccg 10740
gtgatttcgt ggacgagaag aaacctagag tcatacaata ccctgaagca aaaacaagac 10800
tggccatcac caaggtgatg tataagtggg tgaagcagaa gccagtagtt atacccgggt 10860
atgaagggaa gacacctcta ttccaaattt ttgacaaagt gaagaaggaa tgggatcaat 10920
ttcaaaatcc agtggcagtg agcttcgaca ctaaggcgtg ggacacccag gtaaccacaa 10980
aagatttgga gctgataagg gacatacaaa agtattattt caagaagaaa tggcacaaat 11040
ttattgacac cctgaccacg catatgtcag aagtacccgt gattagtgct gatggggaag 11100
tatacataag gaaagggcaa agaggcagtg gacaacctga cacaagtgcg ggcaacagca 11160
tgctaaatgt cttaacaatg gtttacgcct tctgcgaggc cacaggagta ccctacaaga 11220
gctttgacag ggtggcaaaa attcatgtgt gcggggatga tggcttcctg atcacagaaa 11280
gagctctcgg tgagaaattt gcaagtaagg gagtccagat cctttatgaa gctgggaagc 11340
cccagaagat cactgaaggg gacaaaatga aagtggccta ccaatttgat gatattgagt 11400
tttgctccca tacaccaata caagtaagat ggtcagataa cacttctagt tacatgccgg 11460
ggagaaatac aaccacaatc ctggcaaaga tggccacgag gttagattcc agcggtgaaa 11520

-continued

```
ggggtaccat agcatatgag aaagcagtag catttagctt cctgctgatg tattcctgga  11580

acccactaat tagaaggatc tgcttactgg tgctatcaac tgaactgcaa gtgaaaccag  11640

ggaagtcaac tacttactat tatgaaggag acccgatatc tgcctacaag gaagtcatcg  11700

gccacaatct ttttgatctt aagagaacaa gctttgagaa gctggccaag ttaaatctta  11760

gcatgtctgt actcggggcc tggactagac acaccagtaa aagactacta caagactgtg  11820

tcaatatagg tgttaaagag ggcaactggc tagtcaatgc agacagacta gtaagtagca  11880

agaccgggaa taggtacata cccggagagg gtcacaccct gcaaggaaga cattatgaag  11940

aactggtgtt ggcaagaaaa cagatcaaca actttcaagg gacagacagg tacaacctag  12000

gcccaatagt caacatggtg ttaaggaggc tgagagtcat gatgatgacg ctgataggga  12060

gaggggcatg agcgcgggta acccgggatc tgaacccgcc agtaggaccc tattgtagat  12120

aacactaatt ttcttttttc ttttttattt atttagatat tattatttat ttatttattt  12180

atttattgaa tgagtaagaa ctggtataaa ctacctcaag ttaccacact acactcattt  12240

ttaacagcac tttagctgga aggaaaattc ctgacgtcca cagttggact aaggtaattt  12300

ctaacggccc                                                         12310
```

<210> SEQ ID NO 11
<211> LENGTH: 950
<212> TYPE: PRT
<213> ORGANISM: Porcine reproductive and respiratory syndrome virus

<400> SEQUENCE: 11

```
Ala Gly Lys Arg Ala Arg Lys Pro Arg Ser Gly Ala Thr Thr Met Val
1               5                   10                  15

Ala His His Ala Ser Ser Ala His Glu Thr Arg Gln Ala Thr Lys His
            20                  25                  30

Glu Gly Ala Gly Ala Asn Lys Ala Glu His Leu Lys Arg Tyr Ser Pro
        35                  40                  45

Pro Ala Glu Gly Asn Cys Gly Trp His Cys Ile Ser Ala Ile Ala Asn
    50                  55                  60

Arg Met Val Asn Ser Asn Phe Glu Thr Thr Leu Pro Glu Arg Val Arg
65                  70                  75                  80

Pro Ser Asp Asp Trp Ala Thr Asp Glu Asp Leu Val Asn Thr Ile Gln
                85                  90                  95

Ile Leu Arg Leu Pro Ala Ala Leu Asp Arg Asn Gly Ala Cys Gly Ser
            100                 105                 110

Ala Lys Tyr Val Leu Lys Leu Glu Gly Glu His Trp Thr Val Ser Val
        115                 120                 125

Ile Pro Gly Met Ser Pro Thr Leu Leu Pro Leu Glu Cys Val Gln Gly
    130                 135                 140

Cys Cys Glu His Lys Gly Gly Leu Val Ser Pro Asp Ala Val Glu Ile
145                 150                 155                 160

Ser Gly Phe Asp Pro Ala Cys Leu Asp Arg Leu Ala Lys Val Met His
                165                 170                 175

Leu Pro Ser Ser Thr Ile Pro Ala Ala Leu Ala Glu Leu Ser Asp Asp
            180                 185                 190

Ser Asn Arg Pro Val Ser Pro Ala Ala Thr Thr Trp Thr Val Ser Gln
        195                 200                 205

Phe Tyr Ala Arg His Arg Gly Gly Asp His His Asp Gln Val Cys Leu
    210                 215                 220

Gly Lys Ile Ile Ser Leu Cys Gln Val Ile Glu Asp Cys Cys Cys His
```

-continued

```
225                 230                 235                 240

Gln Asn Lys Thr Asn Arg Ala Thr Pro Glu Glu Val Ala Ala Lys Ile
                245                 250                 255

Asp Gln Tyr Leu Arg Gly Ala Thr Ser Leu Glu Glu Cys Leu Ala Lys
            260                 265                 270

Leu Glu Arg Val Ser Pro Pro Ser Ala Ala Asp Thr Ser Phe Asp Trp
        275                 280                 285

Asn Val Val Leu Pro Gly Val Glu Ala Ala Asn Gln Thr Thr Glu Gln
    290                 295                 300

Pro His Val Asn Ser Cys Cys Thr Leu Val Pro Pro Val Thr Gln Glu
305                 310                 315                 320

Pro Leu Gly Lys Asp Ser Val Pro Leu Thr Ala Phe Ser Leu Ser Asn
                325                 330                 335

Cys Tyr Tyr Pro Ala Gln Gly Asp Glu Val His His Arg Glu Arg Leu
            340                 345                 350

Asn Ser Val Leu Ser Lys Leu Glu Glu Val Val Leu Glu Glu Tyr Gly
        355                 360                 365

Leu Met Ser Thr Gly Leu Gly Pro Arg Pro Val Leu Pro Ser Gly Leu
    370                 375                 380

Asp Glu Leu Lys Asp Gln Met Glu Glu Asp Leu Leu Lys Leu Ala Asn
385                 390                 395                 400

Thr Gln Ala Thr Ser Glu Met Met Ala Trp Ala Ala Glu Gln Val Asp
                405                 410                 415

Leu Lys Ala Trp Val Lys Ser Tyr Pro Arg Trp Thr Pro Pro Pro Pro
            420                 425                 430

Pro Pro Arg Val Gln Pro Arg Arg Thr Lys Ser Val Lys Ser Leu Pro
        435                 440                 445

Glu Gly Lys Pro Val Pro Ala Pro Arg Arg Lys Val Arg Ser Asp Cys
    450                 455                 460

Gly Ser Pro Val Leu Met Gly Asp Asn Val Pro Asn Gly Ser Glu Glu
465                 470                 475                 480

Thr Val Gly Gly Pro Leu Asn Leu Pro Thr Pro Ser Glu Pro Met Thr
                485                 490                 495

Pro Met Ser Glu Pro Val Leu Val Pro Ala Ser Arg Arg Val Pro Lys
            500                 505                 510

Leu Met Thr Pro Leu Ser Gly Ser Ala Pro Val Pro Ala Pro Arg Arg
        515                 520                 525

Thr Val Thr Thr Thr Leu Thr His Gln Asp Glu Pro Leu Asp Leu Ser
    530                 535                 540

Ala Ser Ser Gln Thr Glu Tyr Glu Ala Phe Pro Leu Ala Pro Ser Gln
545                 550                 555                 560

Asn Met Gly Ile Leu Glu Ala Gly Gly Gln Glu Val Glu Glu Val Leu
                565                 570                 575

Ser Glu Ile Ser Asp Ile Leu Asn Asp Thr Asn Pro Ala Pro Val Ser
            580                 585                 590

Ser Ser Ser Ser Leu Ser Ser Val Lys Ile Thr Arg Pro Lys Tyr Ser
        595                 600                 605

Ala Gln Ala Ile Ile Asp Ser Gly Gly Pro Cys Ser Gly His Leu Gln
    610                 615                 620

Lys Glu Lys Glu Ala Cys Leu Ser Ile Met Arg Glu Ala Cys Asp Ala
625                 630                 635                 640

Ser Lys Leu Gly Asp Pro Ala Thr Gln Glu Trp Leu Ser Arg Met Trp
                645                 650                 655
```

-continued

```
Asp Arg Val Asp Met Leu Thr Trp Arg Asn Thr Ser Ala Tyr Gln Ala
            660                 665                 670

Phe Arg Ile Leu Asn Gly Arg Phe Glu Phe Leu Pro Lys Met Ile Leu
        675                 680                 685

Glu Thr Pro Pro Pro His Pro Cys Gly Phe Val Met Leu Pro Arg Thr
    690                 695                 700

Pro Ala Pro Ser Val Ser Ala Glu Ser Asp Leu Thr Ile Gly Ser Val
705                 710                 715                 720

Ala Thr Glu Asp Val Pro Arg Ile Leu Gly Lys Ile Gly Asp Thr Asp
                725                 730                 735

Glu Leu Leu Asp Arg Gly Pro Ser Ala Pro Ser Lys Gly Glu Pro Val
            740                 745                 750

Cys Asp Gln Pro Ala Lys Asp Pro Arg Met Ser Pro Arg Glu Ser Asp
        755                 760                 765

Glu Ser Met Ile Ala Pro Pro Ala Asp Thr Gly Gly Val Gly Ser Phe
    770                 775                 780

Thr Asp Leu Pro Ser Ser Asp Gly Val Asp Val Asp Gly Gly Gly Pro
785                 790                 795                 800

Leu Arg Thr Val Lys Thr Lys Ala Gly Arg Leu Leu Asp Gln Leu Ser
                805                 810                 815

Cys Gln Val Phe Ser Leu Val Ser His Leu Pro Ile Phe Phe Ser His
            820                 825                 830

Leu Phe Lys Ser Asp Ser Gly Tyr Ser Pro Gly Asp Trp Gly Phe Ala
        835                 840                 845

Ala Phe Thr Leu Phe Cys Leu Phe Leu Cys Tyr Ser Tyr Pro Phe Phe
    850                 855                 860

Gly Phe Ala Pro Leu Leu Gly Val Phe Ser Gly Ser Ser Arg Arg Val
865                 870                 875                 880

Arg Met Gly Val Phe Gly Cys Trp Leu Ala Phe Ala Val Gly Leu Phe
                885                 890                 895

Lys Pro Val Ser Asp Pro Val Gly Thr Ala Cys Glu Phe Asp Ser Pro
            900                 905                 910

Glu Cys Arg Asn Val Leu His Ser Phe Glu Leu Leu Lys Pro Trp Asp
        915                 920                 925

Pro Val Arg Ser Leu Val Val Gly Pro Val Gly Leu Gly Leu Ala Ile
    930                 935                 940

Leu Gly Arg Leu Leu Gly
945                 950
```

COMBINED VACCINES FOR PREVENTION OF PORCINE VIRUS INFECTIONS

This application is a national stage application under 35 U.S.C. §371 of PCT International Application No. PCT/CN2012/076125, filed May 25, 2012, which claims the benefit of China Patent Application Nos. CN201110331159.8, filed Oct. 27, 2011, CN201110331206.9, filed Oct. 27, 2011, and CN201110140951.5, filed 27 May 2011, which are hereby incorporated by reference in its entirety.

CROSS-REFERENCE TO RELATED APPLICATIONS

The present applications claims priority to the following three Chinese patent applications: 201110140951.5, filed on May 27, 2011, entitled "Combination Vaccines for Porcine Reproductive and Respiratory Syndrome and Classical Swine Fever and Uses Thereof," 201110331206.9, filed on Oct. 27, 2011, entitled "Combination Vaccines for Porcine Reproductive and Respiratory Syndrome and Porcine Pseudorabies Virus and Uses Thereof," 201110331159.8, filed on Oct. 27, 2011, entitled "Triple Combination Vaccines for Porcine Reproductive and Respiratory Syndrome, Classical Swine Fever and Porcine Pseudorabies Virus and Preparation Methods Thereof," which are incorporated herein by reference to their entirety.

FIELD OF THE INVENTION

The present invention relates to veterinary biological products, particularly to the live combination vaccine for preventing porcine reproductive and respiratory syndrome, classical swine fever and porcine pseudorabies virus, and preparations thereof.

BACKGROUND OF THE INVENTION

Porcine reproductive and respiratory syndrome (PRRS) is one of the major infectious diseases threatening pig industry in many places around the world. Ever since the outbreak of highly-pathogenic porcine reproductive and respiratory syndrome (also called highly-pathogenic blue ear disease) in China in 2006, PRRS has caused huge economic loss to Chinese pig industry, and is listed by Chinese Ministry of Agriculture as one of the diseases for which compulsory vaccination is required.

In addition to PRRS, pigs can be further infected by other infectious diseases such as classical swine fever (CSF) and pseudorabies. However, PRRS virus (PRRSV) is known to induce immune suppression after infecting its host, and therefore usually result in reduced immune response to secondary infections or even vaccination failure. Studies have shown that PRRSV impairs host immune system by, for example, destroying alveolar macrophages that are important for generating immune response, and/or suppressing cytokine expression that confers immunological defense to secondary infections. For example, PRRSV infection has been found to significantly inhibit host immune response to Classical Swine Fever Virus (CSFV) vaccine, even resulting in CSFV vaccination failure (Suradhat, S. et al, Vaccine, 24: 2634-3642 (2006); Li, H. et al, Veterinary Microbiology, 95: 295-301 (2003)). Co-vaccination of attenuated PRRSV and attenuated CSFV is reported to have a reduced immuno-protection rate of about 60%, which fails to meet the vaccination requirement. To vaccinate against the two pathogens, individual vaccinations separated by a 14-day interval are required (see, e.g. Du, X. Z. et al, Zhejiang Journal Animal Science and Veterinary Medicine, 2: p 5-6 (2011)). For another example, PRRSV has been found to negatively affect the vaccination effects of Pseudorabies Virus (PRV), and significantly reduce or delay the host immune response against PRV (De Bruin, M. G. M. et al, Veterinary Immunology and Immunopathology, 76(1-2): p 125-135 (2000)).

The immuno-inhibition of PRRSV tends to complicate the vaccination regimen for pigs, and reduce the vaccination efficacy and efficiency. When pigs are vaccinated against PRRSV and other viruses, it is often necessary to apply repetitive injections and multiple dosages, making the vaccination process time-consuming, labor-intensive, and costly. Moreover, in a multiple vaccination regimen, a missing dose can have a direct impact on the protection efficacy of the vaccines, while frequent and repeated vaccinations can result in immuno-paralysis, and induce immunological stress.

Therefore, there exists great need for a combined vaccine composition for PRRSV and other pig infectious diseases, without substantial immuno-inhibition.

SUMMARY OF THE INVENTION

One aspect of the present disclosure relates to vaccine compositions, comprising a Porcine Reproductive and Respiratory Syndrome Virus (PRRSV) vaccine and a second porcine virus vaccine, wherein the PRRSV vaccine and the second vaccine are substantially free from immuno-inhibition against each other. In certain embodiments, the vaccine composition further comprises a third porcine virus vaccine, wherein the PRRSV vaccine, the second vaccine and the third vaccine are substantially free from immuno-inhibition against each other.

In certain embodiments, the second porcine virus vaccine is selected from Classical Swine Fever Virus (CSFV) vaccine and Pseudorabies Virus (PRV) vaccine. In certain embodiments, the third porcine virus vaccine is selected from Classical Swine Fever Virus (CSFV) vaccine and Pseudorabies Virus (PRV) vaccine. The second vaccine is different from the third vaccine.

In certain embodiments, the vaccine compositions comprise a PRRSV vaccine, a CSFV vaccine and a PRV vaccine, wherein the PRRSV vaccine, the CSFV vaccine and the PRV vaccine are substantially free from immuno-inhibition against each other.

In certain embodiments, the PRRSV vaccine comprises an attenuated PRRSV. In certain embodiments, the attenuated PRRSV comprises an Nsp2 nucleotide encoded by a DNA sequence which, when compared with SEQ ID NO: 4, lacks a nucleotide fragment comprising at least 50 contiguous nucleotides, wherein the fragment is at least about 80% homologous to an equal length portion of SEQ ID NO: 8. In certain embodiments, the DNA fragment comprises at least 100, at least 120, at least 150, at least 180, at least 200, at least 210, at least 220, at least 230, at least 240, at least 250, at least 260, at least 270, at least 280, at least 290, at least 300, at least 310, at least 320, at least 330, at least 340, at least 350, or at least 360 contiguous nucleotides. In certain embodiments, the DNA fragment is at least about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or 100% homologous to an equal length portion of SEQ ID NO: 8. In certain embodiments, the DNA fragment comprises SEQ ID NO: 8.

In certain embodiments, the attenuated PRRSV comprises an Nsp2 nucleotide encoding for a Nsp2 protein sequence which, when compared with SEQ ID NO: 11, lacks a peptide fragment comprising at least 20 contiguous amino acids, wherein the fragment is at least about 80% homologous to an equal length portion of SEQ ID NO: 9. In certain embodiments, the peptide fragment comprises at least 30, at least 40, at least 50, at least 60, at least 70, at least 75, at least 80, at least 85, at least 90, at least 95, at least 100, at least 105, at least 110, at least 115, or at least 120 contiguous amino acids. In certain embodiments, the peptide fragment is at least about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or 100% homologous to an equal length portion of SEQ ID NO: 9. In certain embodiments, the peptide fragment comprises SEQ ID NO: 9.

In certain embodiments, the attenuated PRRSV is attenuated from a highly-pathogenic PRRSV. In certain embodiments, the attenuated PRRSV comprises an Nsp2 nucleotide encoded by a DNA sequence which, when compared with SEQ ID NO: 5, lacks discontinuous 90 nucleotides within SEQ ID NO: 6. In certain embodiments, the Nsp2 nucleotide is encoded by a sequence having at least 90% homology to SEQ ID NO: 2. In certain embodiments, the Nsp2 nucleotide is encoded by a sequence comprising SEQ ID NO: 2.

In certain embodiments, the attenuated PRRSV further comprises an Nsp1 nucleotide sequence, which is encoded by a sequence having at least 90% homology to SEQ ID NO: 1. In certain embodiments, the attenuated PRRSV comprises an Nsp1 nucleotide sequence encoded by SEQ ID NO: 1, and an Nsp2 nucleotide sequence encoded by SEQ ID NO: 2.

In certain embodiments, the attenuated PRRSV comprises a PRRSV nucleotide sequence encoded by a sequence having at least 90% homology to SEQ ID NO: 3. In certain embodiments, the attenuated PRRSV comprises a PRRSV nucleotide sequence encoded by SEQ ID NO: 3. In certain embodiments, the attenuated PRRSV has a microorganism deposit number of CGMCC No.: 3121.

In certain embodiments, the CSFV vaccine comprises an attenuated CSFV. In certain embodiments, the attenuated CSFV is encoded by a sequence having at least 80% homology to SEQ ID NO: 10. In certain embodiments, the attenuated CSFV is encoded by SEQ ID NO: 10. In certain embodiments, the attenuated CSFV has a microorganism deposit number of CGMCC No.: 3891.

In certain embodiments, the PRV vaccine comprises an attenuated PRV. In certain embodiments, the attenuated PRV comprises a sequence having at least 80% homology to a sequence having an NCBI reference number of NC 006151.

In certain embodiments, the attenuated PRV has one or more inactivated genes selected from the group consisting of TK, PK, RR, dUTPase, gG, gC, gE, gD and gI. In certain embodiments, the attenuated PRV has an inactivated gE gene. In certain embodiments, the attenuated PRV has a microorganism deposit number of CGMCC No.: 5076.

In certain embodiments, the vaccine composition provided herein comprises an immunologically effective amount of the PRRSV vaccine, the CSFV vaccine and/or the PRV vaccine. In certain embodiments, the immunologically effective amount of the PRRSV vaccine is at least $10^{4.5}$ $TCID_{50}$, $10^{5.0}$ $TCID_{50}$, or $10^{5.5}$ $TCID_{50}$, the immunologically effective amount of the CSFV vaccine is at least $10^{0.5}$ FA-$TCID_{50}$ (fluorescent antibody—$TCID_{50}$), $10^{1.0}$ FA-$TCID_{50}$, $10^{1.5}$ FA-$TCID_{50}$, $10^{2.0}$ FA-$TCID_{50}$, $10^{2.5}$ FA-$TCID_{50}$, $10^{3.0}$ $TCID_{50}$, $10^{3.5}$ FA-$TCID_{50}$, $10^{4.0}$ FA-$TCID_{50}$, $10^{4.5}$ FA-$TCID_{50}$, or $10^{5.0}$ FA-$TCID_{50}$, or is at least 2.5 RID (rabbit infective dose), 3 RID, 5 RID, 10 RID, 30 RID, 100 RID, 150 RID, 300 RID, 750 RID, 1000 RID, 3000 RID, or 7500 RID, and/or the immunologically effective amount of the PRV vaccine is at least $10^{3.0}$ $TCID_{50}$, $10^{3.5}$ $TCID_{50}$, $10^{4.0}$ $TCID_{50}$, $10^{4.5}$ $TCID_{50}$, $10^{5.0}$ $TCID_{50}$, $10^{5.5}$ $TCID_{50}$ or $10^{6.0}$ $TCID_{50}$.

In certain embodiments, the $TCID_{50}$ ratio of the PRRSV vaccine to the CSFV vaccine in the combined vaccine ranges from 10000:1 to 1:1. In certain embodiments, the $TCID_{50}$ ratio of the PRRSV vaccine to the PRV vaccine in the combined vaccine ranges from 1:1 to 1:30. In certain embodiments, the $TCID_{50}$ ratio of the PRRSV vaccine:the CSFV vaccine:the PRV vaccine in the combined vaccine ranges from about $10^4$:1:$10^5$ to about 5:1:6.

In certain embodiments, the vaccine compositions further comprises an adjuvant. In certain embodiments, the vaccine compositions further comprises a cryoprotectant. In certain embodiments, the cryoprotectant comprises sucrose, L-sodium glutamate, and/or lactalbumin hydrolysate.

In another aspect, the present disclosure provides methods for preparing the vaccine compositions provided herein, comprising: (a) collecting PRRSV vaccine strain, CSFV vaccine strain and/or PRV vaccine strain, which are cultivated in their respective susceptible cells, and (b) mixing two or more of the virus strains at a suitable $TCID_{50}$ ratio.

In certain embodiments, the susceptible cells for the PRRSV vaccine strain is a cell line selected from the group consisting of Marc-145, MA-104, Vero, and CL-2621, or a primary cell which is PAM cell. In certain embodiments, the susceptible cells for the CSFV vaccine strain is a cell line selected from the group consisting of BT, Vero, MPK, SK6, PK2a, CPK, RKC, MDBK, MDCK, CRFK, ST, and PT, or a primary cell which is BT cell. In certain embodiments, the susceptible cells for the PRV vaccine strain is a cell line selected from the group consisting of ST, PK-15, Marc-145, MDBK, BT, Vero, BHK-21, porcine kidney cell line (IBRS-2), rabbit kidney cell line (RK), and chicken embryo fibroblast cell line, or a primary cell which is porcine kidney primary cell.

In certain embodiments, the cultivation comprises inoculating each vaccine strain to its susceptible cells at a cell density ranging from $1\times10^6$/ml-$5\times10^6$/ml in a roller bottle culture, or at a cell density ranging from $5\times10^6$/ml-$1\times10^7$/ml in a suspension culture with an introduced adherent carrier in a bioreactor.

In certain embodiments, the PRRSV vaccine strain is inoculated at a Multiplicity of Infection (MOI) of 0.01-0.5, the CSFV vaccine strain is inoculated at a MOI of 0.1-0.5, and/or the PRV vaccine strain is inoculated at a MOI of 0.005-0.5.

In certain embodiments, the step (b) comprises mixing the collected PRRSV vaccine virus with the CSFV vaccine virus at a $TCID_{50}$ ratio from 10000:1 to 1:1. In certain embodiments, the step (b) comprises mixing the collected PRRSV vaccine virus with the PRV vaccine virus at a $TCID_{50}$ ratio from 1:1 to 1:30. In certain embodiments, the step (b) comprises mixing the collected PRRSV vaccine virus, the CSFV vaccine virus, and the PRV vaccine virus at a $TCID_{50}$ ratio from $10^4$:1:$10^5$ to about 5:1:6.

In certain embodiments, the step (b) further comprises mixing the mixture of the collected virus solutions with a cryoprotectant. In certain embodiments, the mixture of the collected virus solutions is mixed with the cryoprotectant in a volume ratio of 75-80:25-20.

In another aspect, the present disclosure provides vaccine compositions prepared using the methods provided herein.

In another aspect, the present disclosure provides use of the vaccine compositions provided herein in the manufacture of a medicament for preventing or treating PRRS, CSF, and/or PR.

In another aspect, the present disclosure provides methods of immunizing a pig, comprising administering to the pig a vaccine composition provided herein.

In another aspect, the present disclosure provides CSFV vaccine strains, cultured in a cell line selected from the group consisting of ST, PK-15, Marc-145, MDBK, BT, Vero, BHK-21, porcine kidney cell line (IBRS-2), rabbit kidney cell line (RK), and chicken embryo fibroblast cell line, or a primary cell which is porcine kidney primary cells. In another aspect, the present disclosure provides use of these cell lines in culturing a CSFV vaccine strain.

BRIEF DESCRIPTION OF THE DRAWINGS

FIG. 1 shows 360 continuous nucleotides which are absent in the Nsp2 coding sequence of PRRSV TJM strain, but is present in the Nsp2 nucleotide sequence of PRRSV TJ strain.

FIG. 2 shows the 120 amino acid sequence which are absent in the Nsp2 protein as encoded by PRRSV TJM strain, but is present in the Nsp2 protein of PRRSV TJ strain.

FIG. 3 is a schematic drawing showing the 90-nucleotide deletion in the Nsp2 coding sequence of the highly-pathogenic PRRSV strain, and the 90-nucleotide deletion and the 360-nucleotide deletion in an attenuated PRRSV TJM strain.

FIG. 4 shows the discontinuous 90 nucleotide sequence which is absent in the highly-pathogenic PRRSV TJ strain, but is present in the PRRSV VR-2332 strain.

200904, 200905 and 200906 represent three batches of 2-combo vaccine, and 200901, 200902 and 200903 represent three batches of PRRSV TJM single vaccine.

Figure 30:
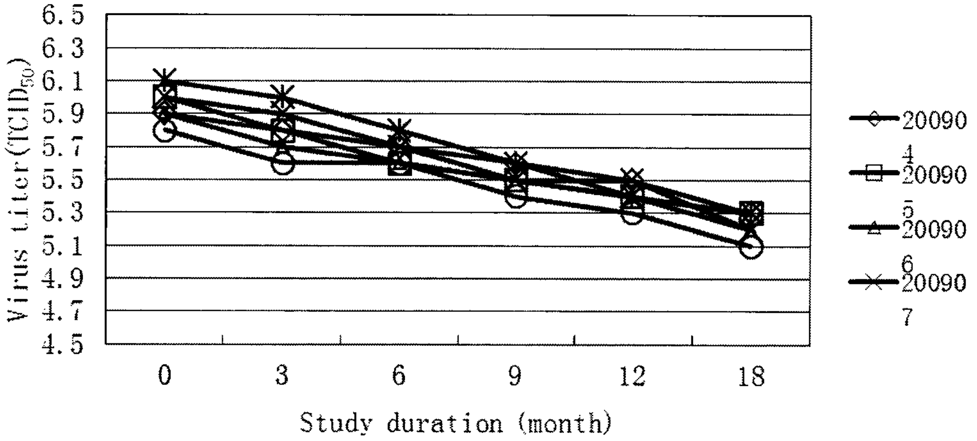

FIG. 30 shows the virus titers of PRRSV TJM strain in the PRRSV single vaccine and in the 2-combo vaccine (PRRSV and CSFV) after storage at 2-8° C. for 18 months. 200904, 200905 and 200906 represent three batches of 2-combo vaccine, and 200907, 200908 and 200909 represent three batches of CSFV C strain (F16).

Figure 31:
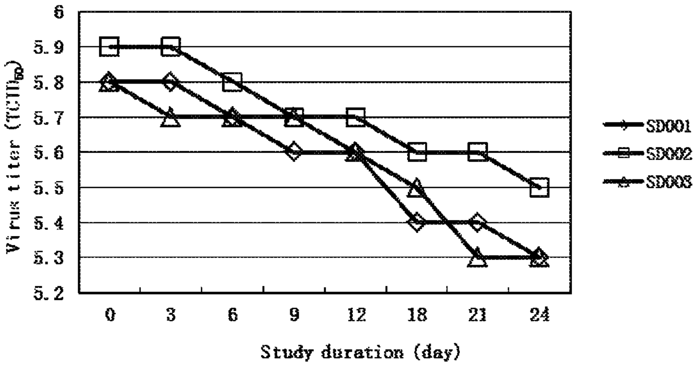

FIG. 31 shows the virus titers of PRRSV TJM strain in the 2-combo vaccine (PRRSV and PRV) after storage at 2-8° C. for 24 months. SD001, SD002 and SD003 represent three different batches of 2-combo live vaccine, respectively.

Figure 32:
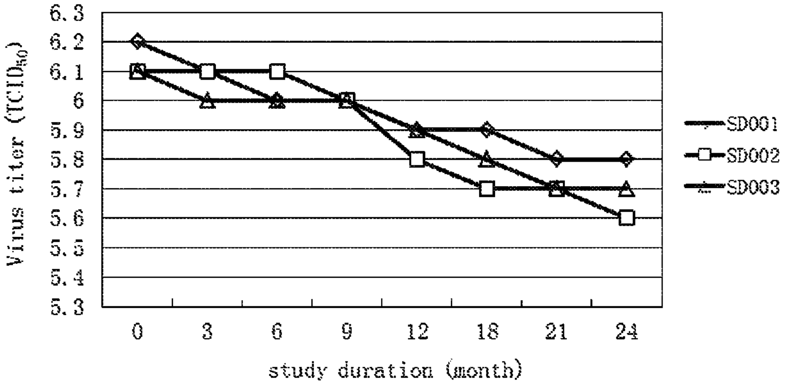

FIG. 32 shows the virus titers of PRV Bartha K61 strain in the 2-combo vaccine (PRRSV and PRV) after storage at 2-8° C. for 24 months. SD001, SD002 and SD003 represent three different batches of 2-combo live vaccine, respectively.

Figure 33:
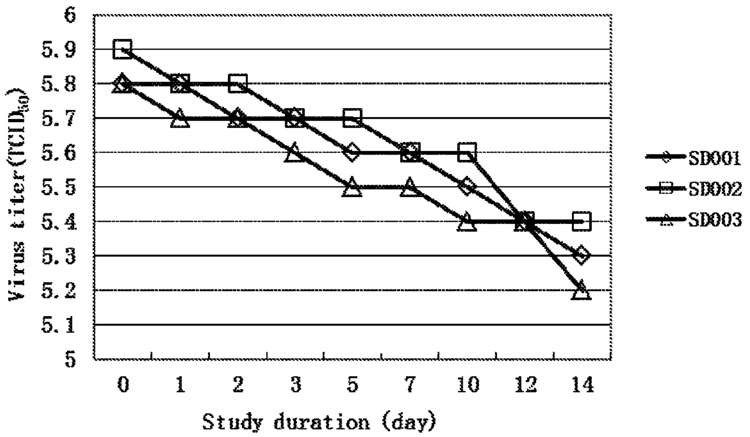

FIG. 33 shows the virus titers of PRRSV TJM strain in the 2-combo vaccine (PRRSV and PRV) after storage at 37° C. for 14 days. SD001, SD002 and SD003 represent three different batches of 2-combo live vaccine, respectively.

Figure 34:
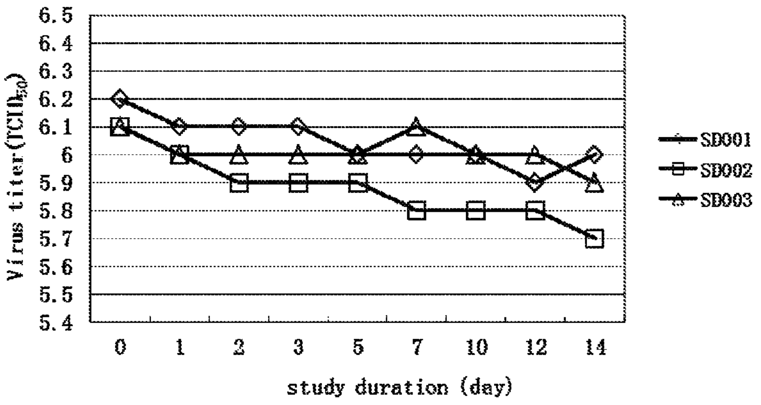

FIG. 34 shows the virus titers of PRV Bartha K61 strain in the 2-combo vaccine (PRRSV and PRV) after storage at 37° C. for 14 days. SD001, SD002 and SD003 represent three different batches of 2-combo live vaccine, respectively.

Figure 35:
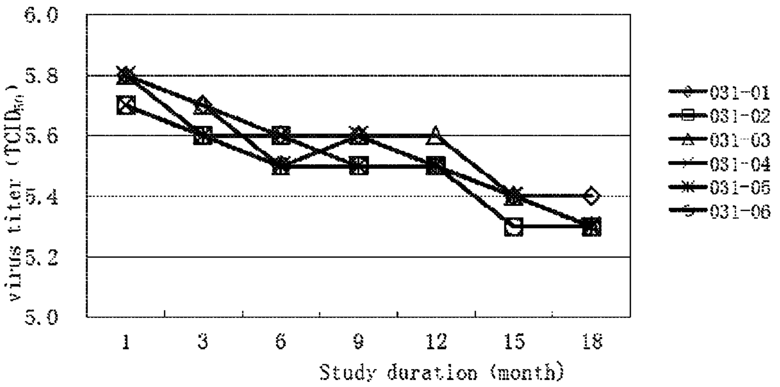

FIG. 35 shows the virus titers of PRRSV TJM strain in the 3-combo live vaccine (PRRSV TJM+CSFV C strain (F16)+PRV Bartha K61) after storage 2-8° C. for 18 months. 031-01, 031-02 and 031-03 represent three batches of 3-combo live vaccine, and 031-04, 031-05 and 031-06 represent three batches of PRRSV TJM single vaccine.

Figure 36:
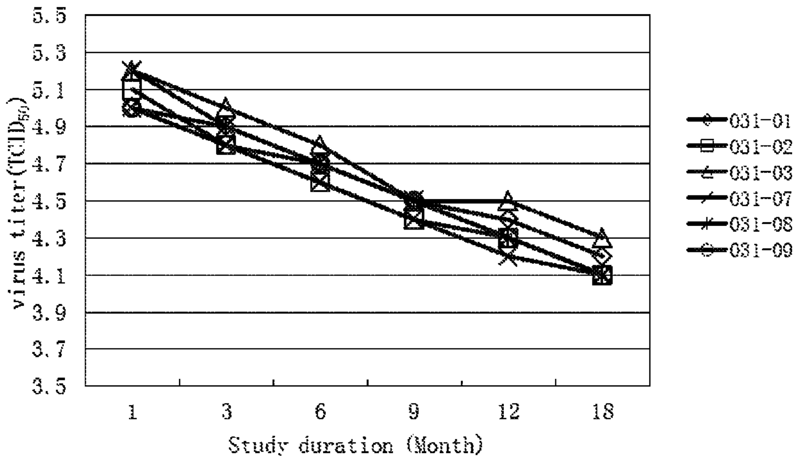

FIG. 36 shows the virus titers of CSFV C strain (F16) strain in the 3-combo live vaccine (PRRSV TJM+CSFV C strain (F16)+PRV Bartha K61) after storage 2-8° C. for 18 months. 031-01, 031-02 and 031-03 represent three batches of 3-combo live vaccine, and 031-07, 031-08 and 031-09 represent three batches of CSFV C strain (F16) single vaccine.

Figure 37:
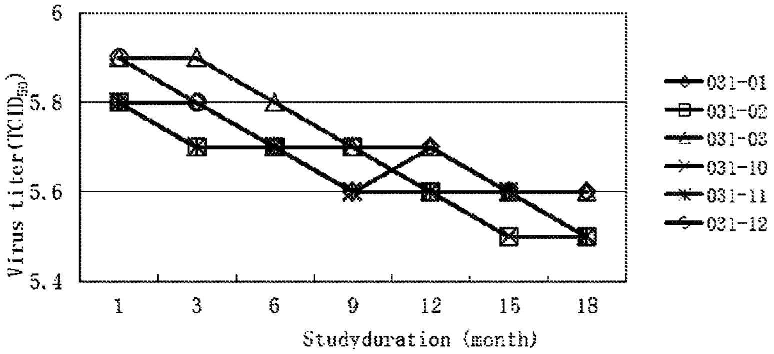

FIG. 37 shows the virus titers of PRV Bartha K61 strain in the 3-combo live vaccine (PRRSV TJM+CSFV C strain (F16)+PRV Bartha K61) after storage 2-8° C. for 18 months. 031-01, 031-02 and 031-03 represent three batches of 3-combo live vaccine, and 031-10, 031-11 and 031-12 represent three batches of PRV Bartha K61 single vaccine.

Figure 38:
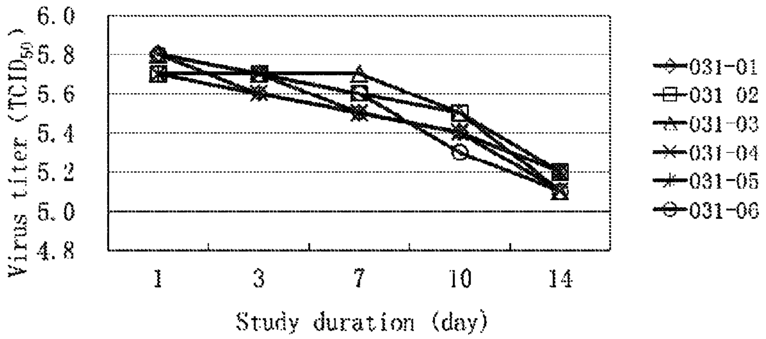

FIG. 38 shows the virus titers of PRRSV TJM strain in the 3-combo live vaccine (PRRSV TJM+CSFV C strain (F16)+PRV Bartha K61) after storage 37° C. for 14 days. 031-01, 031-02 and 031-03 represent three batches of 3-combo live vaccine, and 031-04, 031-05 and 031-06 represent three batches of PRRSV TJM single vaccine.

Figure 39:
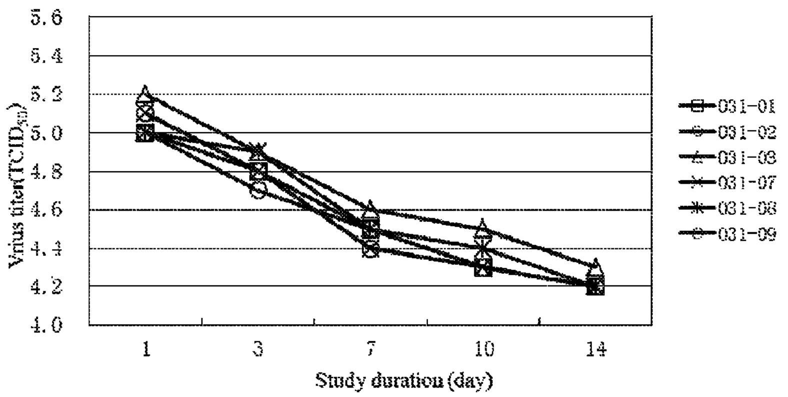

FIG. 39 shows the virus titers of CSFV C strain (F16) in the 3-combo live vaccine (PRRSV TJM+CSFV C strain (F16)+PRV Bartha K61) after storage 37° C. for 14 days. 031-01, 031-02 and 031-03 represent three batches of 3-combo live vaccine, and 031-07, 031-08 and 031-09 represent three batches of CSFV C strain (F16) single vaccine.

Figure 40:
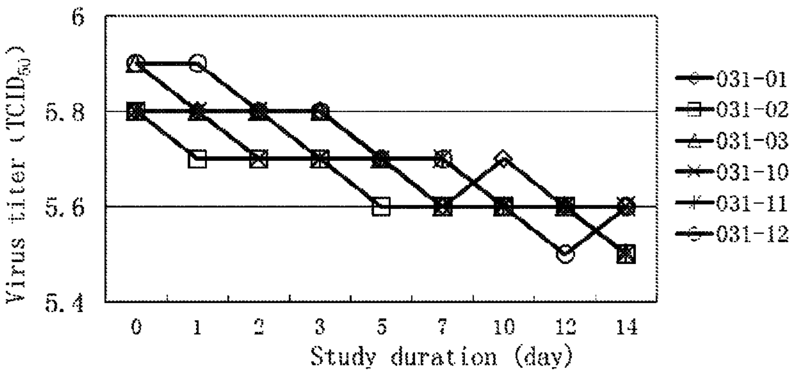

FIG. 40 shows the virus titers of PRV Bartha K61 strain in the 3-combo live vaccine (PRRSV TJM+CSFV C strain (F16)+PRV Bartha K61) after storage 37° C. for 14 days. 031-01, 031-02 and 031-03 represent three batches of 3-combo live vaccine, and 031-10, 031-11 and 031-12 represent three batches of PRV Bartha K61 single vaccine.

DETAILED DESCRIPTION OF THE INVENTION

The following description is merely intended to illustrate various embodiments of the present disclosure. As such, the specific modifications discussed are not intended to be limiting. It will be apparent to one skilled in the art that various equivalents, changes, and modifications may be made without departing from the spirit or scope of the subject matters presented herein, and it is understood that such equivalent embodiments are to be included herein. All publications, patents or patent applications cited herein are incorporated by reference to their entirety.

One aspect of the present disclosure relates to vaccine compositions, comprising a Porcine Reproductive and Respiratory Syndrome Virus (PRRSV) vaccine and a second porcine virus vaccine, wherein the PRRSV vaccine and the second vaccine are substantially free from immuno-inhibition against each other.

PRRSV is a positive-strand RNA virus, for which two genotypes are currently identified: European genotype and American genotype. The genome of PRRSV contains multiple open reading frames, in which the first open reading frame (ORF1a and ORF1b) contains 80% of the sequence in the PRRSV genome, and encodes the RNA replicase which is required for PRRSV replication (Straw et al, Diseases of Swine, 9TH edition, chapter 24 (2006)). ORF1a and ORF1b are translated into a poly-protein, which is cleaved by a protease domain contained therein into several non-structural proteins, including Nsp1-Nsp12 (see, eg, Vries et al, Seminars in Virology, 8: 33-47 (1997); Allende et al, Journal of General Virology, 80: 307-315 (1999)).

The PRRSV vaccine and the second porcine virus vaccine are substantially free from immuno-inhibition against each other.

The term "substantially free from immuno-inhibition" as used herein means that, the combination two or more single vaccines does not lead to substantial reduction in protective immune response in a host to one of the single vaccines or to all of the single vaccines. The term "substantial reduction," as used herein, refers to ≥20% reduction (e.g. ≥30%, ≥40%, ≥50%, or ≥60% reduction).

In certain embodiments, the combination of two or more single vaccines is capable of eliciting protective immune response to each of the single vaccines at a level comparable to that elicited by a single vaccine. For example, the combined PRRSV vaccine and the second porcine virus vaccine can elicit immune response to PRRSV which is at a level comparable to the immune response elicited by the PRRSV single vaccine, and/or can elicit immune response to the second porcine virus vaccine which is at a level comparable to the immune response elicited by the second porcine virus single vaccine.

The protective immune response typically includes humoral, cellular and/or mucosal immune responses, and can be characterized using methods known in the art. Humoral immune response is generated by production of antibodies (e.g. IgG) in the serum against the antigen. The antibody titers can be readily measured using assays such as ELISA (enzyme linked immunosorbent assay). For example, the virus antigen can be coated on a solid support, and then contacted with a sample suspected of containing the antibody, followed by determination of the formation of antigen-antibody complex. Cellular immune response is usually resulted from generation of cytotoxic T lymphocytes, and can be characterized through measurement of certain sub-populations of the T cells, such as CD3+ T cells, CD4+ T cells, CD8+ T cells, and CD4+CD8+ T cells, using methods such as flow cytometry. Briefly, the T cells are stained with antibodies against certain surface markers, and were sorted and quantified as different sub-populations according to the presence of the surface markers. Mucosal immune response is typically resulted from secretory IgA generated on the mucosal surfaces.

In certain embodiments, the PRRSV vaccine and the second porcine virus vaccine, when administered as a combined vaccine composition, do not substantially reduce antibody production in a host in response to the PRRSV vaccine and/or the second porcine virus vaccine.

In certain embodiments, the PRRSV vaccine and the second porcine virus vaccine, when administered as a combined vaccine composition, do not substantially reduce levels of CD3+ T cells, CD4+ T cells, CD8+ T cells, and/or CD4+CD8+ T cells in a host in response to the PRRSV vaccine and/or the second porcine virus vaccine.

In certain embodiments, the PRRSV vaccine comprises an attenuated PRRSV. In the present disclosure, "attenuated PRRSV" as used herein refers to a PRRSV that can infect a host but do not cause porcine reproductive and respiratory syndrome, or having less and/or milder symptoms. Attenuated PRRSV includes live attenuated PRRSV and its inactivated products. "Porcine reproductive and respiratory syndrome" (PRRS) as used herein refers to a series of physiological and pathological symptoms after infection of a naturally-occurring PRRSV. The symptoms include, without limitation, fever, drowsiness, anorexia, lassitude, dyspnea, cough, breeding disorder in sows, and slow growth or death in piglets, among others.

In certain embodiments, the attenuated PRRSV comprises an Nsp2 nucleotide encoded by a DNA sequence which, when compared with SEQ ID NO: 4, lacks a nucleotide fragment comprising at least 50 contiguous nucleotides, wherein the fragment is at least about 80% homologous to an equal length portion of SEQ ID NO: 8.

The term "encoded by a DNA sequence" as used herein refers to a DNA sequence that can be transcribed into a corresponding RNA sequence. A single stranded RNA virus, such as PRRSV and CSFV, has a genome which is composed of a singe strand RNA molecule that can be encoded by a DNA molecule based on Watson Crick base pairing. Such DNA molecule, when transcribed, can produce a positive-strand RNA molecule that is the identical to the RNA sequence in the virus genome.

Without being bound to theory, but it is contemplated that the absence of such nucleotide fragment in Nsp2 sequence within the portion homologous to SEQ ID NO: 8 can reduce the virulence as well as the immuno-inhibition potential of PRRSV, by, for example, producing a non-functional or less-functional Nsp2 protein, and/or negatively affecting the expression or function of other PRRSV proteins, and/or negatively affecting the life cycle of the PRRSV.

The absent fragment can be of any suitable length, as long as it can reduce the virulence as well as the immuno-inhibition of PRRSV, to the extent that is sufficient to abolish PRRSV virulence and to induce protective immunity against PRRSV without impairing immunity against other co-infected virus or vaccines. For example, the absent DNA fragment can comprise at least 100, at least 120, at least 150, at least 180, at least 200, at least 210, at least 220, at least 230, at least 240, at least 250, at least 260, at least 270, at least 280, at least 290, at least 300, at least 310, at least 320, at least 330, at least 340, at least 350, or at least 360 contiguous nucleotides. The length of the absent nucleotide fragment can also be within a range defined by any of the two values as provided above, as if these ranges have been explicitly listed herein. In certain embodiments, the absent nucleotide fragment comprises about 300 contiguous nucleotides, about 310, about 320, about 330, about 340, about 350, or about 360 contiguous nucleotides.

People of ordinary skill in the art can readily prepare recombinant viruses having various deletions in Nsp2 nucleotide sequence within the portion homologous to SEQ ID NO: 8, and test these recombinant viruses for their viability, virulence, and immuno-inhibition potential, using methods known in the art and methods provided in the present disclosure. For example, with the respect to producing and testing virulence of recombinant PRRSV containing deletions in Nsp2, methods have been described in Kim, Dal-Young et al, Virus Genes, 38: 118-128 (2009). With respect to testing immuno-inhibition of the recombinant PRRSV, methods have been described in Suradhat, S. et al, Vaccine, 24: 2634-3642 (2006), and also in Examples of the present disclosure. By deleting a fragment within the portion homologous to SEQ ID NO: 8 (e.g. deleting the $1^{st}$ nucleotide through the $50^{th}$ nucleotide in the portion, the $2^{nd}$ through the $60^{th}$ nucleotide, the $5^{th}$ through the $100^{th}$ nucleotide, etc.), one can prepare recombinant PRRSV comprising an Nsp2 nucleotide of interest, and further test the viable recombinant PRRSV strains for their abilities in forming cytopathic plaques, such that attenuated recombinant PRRSV strains can be selected and further tested in pigs for immuno-inhibition potential with respect to a second porcine virus vaccine.

In certain embodiments, the absent DNA fragment is at least about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or 100% homologous to an equal length portion of SEQ ID NO: 8. In certain embodiments, the absent DNA fragment comprises SEQ ID NO: 8. In certain embodiments, the absent DNA fragment is SEQ ID NO: 8 (see FIG. 1).

In certain embodiments, the attenuated PRRSV comprises an Nsp2 nucleotide encoding for a Nsp2 protein sequence which, when compared with SEQ ID NO: 11, lacks a peptide fragment comprising at least 20 contiguous amino acids, wherein the peptide fragment is at least about 80% homologous to an equal length portion of SEQ ID NO: 9.

The term "encoding for" as used herein means that an RNA sequence that can be translated to a corresponding amino acid sequence in accordance to the genetic codons.

Without being bound to theory, but it is contemplated that Nsp2 protein lacking such peptide fragment is less-functional or non-functional, thus impairing the virulence of the PRRSV and also reduce the immuno-inhibition on a second porcine virus vaccine.

In certain embodiments, the absent peptide fragment comprises at least 30, at least 40, at least 50, at least 60, at least 70, at least 75, at least 80, at least 85, at least 90, at least 95, at least 100, at least 105, at least 110, at least 115, or at least 120 contiguous amino acids. In certain embodiments, the absent peptide fragment is at least about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or 100% homologous to an equal length portion of SEQ ID NO: 9. In certain embodiments, the absent peptide fragment comprises SEQ ID NO: 9. In certain embodiments, the absent peptide fragment is SEQ ID NO: 9 (see FIG. 2).

The absence of the peptide fragment in Nsp2 protein can be determined through the Nsp2 nucleotide sequence. For example, the Nsp2 nucleotide can be sequenced and translated to amino acid sequence, followed by alignment with SEQ ID NO: 11 to identify the absent peptide sequence.

"Homology" or "homologous" as used herein refers to the similarity between two amino acid sequences or two nucleotide sequences. The homology between the amino acid sequences or nucleotide sequences can be calculated using any suitable methods known in the art, for example, the candidate amino acid (nucleotide) sequence can be aligned with a reference amino acid (nucleotide) sequence, introducing gaps if necessary, to achieve the maximum number of identical amino acid residues (nucleotides) between the aligned sequences, on which basis the percentage of the identical amino acid residues (nucleotides) between the two amino acid (nucleotide) sequences can be calculated. Alignment of the amino acid (or nucleotide) sequences and calculation of their homology can be achieved using the software known in the art, for example without limitation, BLAST program see, e.g., Altschul S. F. et al, J. Mol. Biol., 215:403-410 (1990); Stephen F. et al, Nucleic Acids Res., 25:3389-3402 (1997)), ClustalW2 software see, e.g., Higgins D. G. et al, Methods in Enzymology, 266:383-402 (1996); Larkin M. A. et al, Bioinformatics (Oxford, England), 23(21): 2947-8 (2007)); and TCoffee software, etc see, e.g., Poirot O. et al, Nucleic Acids Res., 31(13): 3503-6 (2003); Notredame C. et al, J. Mol. Boil., 302(1): 205-17 (2000)). When software is used to align sequences, default parameters provided by software can be used or adjusted according to the actual situation, and these are within the scope of knowledge of an ordinary artisan in the art.

In certain embodiments, the attenuated PRRSV is attenuated from a highly-pathogenic PRRSV.

The term "highly-pathogenic PRRSV" refers to a PRRSV comprising an Nsp2 nucleotide encoded by a DNA sequence which, when compared with SEQ ID NO: 5, lacks discontinuous 90 nucleotides within the portion of SEQ ID NO: 6 (i.e. the fragment from the 1440th to the 1680th nucleotide of SEQ ID NO: 5). PRRSV isolates lacking such 90 discontinuous nucleotides (see FIG. 3) are found to have higher pathogenicity than PRRSV VR-2332 strain (see, e.g. Tian et al, PLoS ONE 2(6): e526, (2007) doi:10.1371). In certain embodiments, the discontinuous 90 nucleotides include the "TTT" from the 1440 to the 1442 nucleotide of SEQ ID NO: 5 and the sequence as shown in SEQ ID NO: 7 (see, for example, FIG. 4).

In certain embodiments, the highly-pathogenic PRRSV comprise an Nsp2 nucleotide encoded by a sequence comprising a nucleotide sequence of SED ID NO: 4 (i.e., the Nsp2 nucleotide sequence of PRRSV TJ strain). In certain embodiments, the highly-pathogenic PRRSV is PRRSV TJ strain, whose genome is encoded by a sequence having a GenBank Accession number of EU860248.

In certain embodiments, the attenuated PRRSV is attenuated from the highly-pathogenic PRRSV, and comprises an Nsp2 nucleotide sequence lacking discontinuous 90 nucleotides when compared with SEQ ID NO: 5, wherein the discontinuous 90 nucleotides are within SEQ ID NO: 6.

In certain embodiments, the Nsp2 nucleotide of the attenuated PRRSV is encoded by a sequence having at least 90% homology to SEQ ID NO: 2 (i.e. the sequence encoding Nsp2 nucleotide of PRRSV TJM strain). In certain embodiments, the Nsp2 nucleotide is encoded by a sequence comprising SEQ ID NO: 2.

In certain embodiments, the attenuated PRRSV further comprises an Nsp1 nucleotide sequence, which is encoded by a sequence having at least 90% homology to SEQ ID NO: 1 (i.e. the sequence encoding Nsp1 nucleotide of PRRSV TJM strain). In certain embodiments, the attenuated PRRSV comprises an Nsp1 nucleotide sequence encoded by SEQ ID NO: 1, and an Nsp2 nucleotide sequence encoded by SEQ ID NO: 2.

In certain embodiments, the attenuated PRRSV comprises a PRRSV nucleotide sequence encoded by a sequence having at least 90% homology to SEQ ID NO: 3 (i.e. the sequence encoding genome of PRRSV TJM strain). In certain embodiments, the attenuated PRRSV comprises a PRRSV nucleotide sequence encoded by SEQ ID NO: 3. In certain embodiments, the attenuated PRRSV has a microorganism deposit number of CGMCC No.: 3121 (such attenuated PRRSV strain is also referred to herein as PRRSV TJM strain).

The PRRSV vaccine provided herein is substantially free from immuno-inhibition against a second porcine virus vaccine. In certain embodiments, the second porcine virus vaccine is selected from Classical Swine Fever Virus (CSFV) vaccine and Pseudorabies Virus (PRV) vaccine.

Classical Swine Fever (CSF) is a highly contagious and lethal swine infectious disease caused by Classical Swine Fever Virus (CSFV). World Organization for Animal Health (OIE) has included the disease in the OIE disease list as a disease required by law to be reported. In China, classical swine fever is one of the major infectious diseases, and is listed as type I animal disease in "Category of Type I, II and III Animal Diseases." The outbreak and prevalence of the CSF has led to the great economic loss in pig industry in China and worldwide.

Classical swine fever virus (CSFV) is classified as a member of the Pestivirus genus within the Flaviviridae family of viruses. CSFV is an enveloped positive-strand RNA virus. The virus has a genome of 12.5 kb in its full length, which comprises only one large open reading frame (ORF) that encodes a poly-protein containing approximately 4000 amino acids and with a molecular weight of about 438 kD. The poly-protein is further processed into 12 mature proteins by the viral and host proteases. All of the structural and non-structural proteins of CSFV are encoded by this large open reading frame.

An important tool to control the classical swine fever is vaccines, including inactivated vaccines and attenuated vaccines. Preparation of inactivated CSFV vaccines reached its peak in 1950-1960's, during which period formalin and crystal violet inactivated CSFV vaccines were widely used. However, they were gradually replaced by the attenuated CSFV vaccines due to their disadvantages in large dosage, short duration of immunity, slow generation of immune responses and high costs.

In certain embodiments, the CSFV vaccine is an attenuated CSFV vaccine. CSFV attenuated vaccine strains can be produced by attenuation of CSFV field strains. Reports in other countries showed that, different methods can be used to adapt CSF viruses in rabbits and to produce attenuated mutant strains. For example, three attenuated vaccine strains are widely accepted as safe and effective yet without residual pathogenicity: 1) Chinese lapinized vaccine strain (see, e.g. Qiu, H. J. et al, Scientia Agricultura Sinica, 38(8): 1675-1685 (2005)); 2) Japanese GPE(−) cell attenuated vaccine strain (see, e.g. Liu, C. et al, Chinese Journal of Animal Husbandry and Veterinary Medicine, Vol. 10, pp. 50-51 (2004)); and 3) French "Thiveosal" cold attenuated vaccine strain (see, e.g. Zhu, L. Q. et al, Chinese Veterinary Journal, 39 (2):

In certain embodiments, the attenuated CSFV vaccine is Chinese lapinized vaccine strain (C strain). The genome sequence of CSFV C strain is shown in SEQ ID NO: 10. The Chinese CSF lapinized vaccine (also called C strain), developed by Chinese scientists, has been widely used in China since 1957, and has been introduced to many other countries, where classical swine fever was brought under control or eliminated. This vaccine has been recognized as one of the most useful CSFV vaccine strains worldwide.

The CSF lapinized vaccine (C strain) can be classified according to the different methods of preparation. The first method involves preparing the vaccine in rabbits. A rabbit is inoculated with CSFV, and the lymph node, spleen or tissue is collected from the rabbit to prepare CSFV vaccine of spleen and lymph tissue origin, or CSFV vaccine of rabbit origin. This method can effectively prevent contamination of exogenous virus and ensure genetic stability of the virus. However, a lot of rabbits are required yet the quality is hard to control, and the manufacturing cost is relatively high. The second method involves using cattle or sheep primary cells or a swine cell line to produce the vaccine, i.e. CSFV vaccine of cell origin. For example, CSFV vaccine of cell origin can be prepared by passing the CSF lapinized virus (spleen origin) in cells, and performing two rounds of clonal purification by serial dilutions. This method does not require using a lot of animals. In certain embodiments, the CSFV C strain is CSFV C strain of spleen and lymph tissue origin. In certain embodiments, the CSFV C strain is CSFV C strain of cell origin, which can be derived from primary cells or a cell line.

In certain embodiments, the attenuated CSFV is encoded by a sequence having at least 80% homology to SEQ ID NO: 10 (i.e. a sequence encoding the genome of CSFV C strain). In certain embodiments, the attenuated CSFV is encoded by SEQ ID NO: 10.

In certain embodiments, the attenuated CSFV has a microorganism deposit number of CGMCC No.: 3891 (such attenuated CSFV strain is also referred to herein as CSFV C strain or F16 or CSFV C strain (F16)). CSFV C strain (F16) is CSFV C strain of cell origin.

In certain embodiments, the second porcine virus vaccine is Pseudorabies Virus (PRV) vaccine.

PRV belongs to the family of Herpesvirdae and subfamily of Alpherpesvirinae. At present, only one serotype of PRV has been identified. The genome of PRV is double-stranded DNA, having a length of about 150 kb. The virus genome is composed of a unique long (UL) region, a unique short (US) region, and terminal repeat sequences flanking the US region and internal repeat sequences. To date, 65 genes have been located in the PRV genome and most of them have been functional characterized. 56 genes have been located in the UL region, including glycoproteins such as gB, gC, gH, gK, gL, gM, gN, thymidine kinase (TK), alkaline nuclease (AN), ribonucleotide reductase (RR), DNA polymerase (POL), DBP gene, MCP gene, ICP18.5 gene and early protein 0 (EP0) and etc. The US region has been fully sequenced, in which 7 genes have been located, including: glycoprotein gD, gE, gG, gI, and protein kinase (PK) gene, 11 kd and 28 kd protein gene.

In certain embodiments, the PRV vaccine comprises an attenuated PRV. The term "attenuated PRV vaccine" refers to a PRV that is capable of infecting its host but does not cause Pseudorabies or with reduced or less severe symptoms. The attenuated PRV include live attenuated PRV and its inactivated product thereof "Pseudorabies" refers to a series of physiological and pathological symptoms caused by infection of wild type PRV. Such symptoms include, without limitation, miscarriage, stillbirth, weak foetus, mummified foetus, fever, low appetite, neurological symptoms, paralysis, system failure and even death.

In certain embodiments, the attenuated PRV comprises a sequence having at least 80% homology to a sequence having an NCBI reference number of NC 006151, for example, having at least 85%, 88%, 90%, 91%, 92%, 93%, 94%, 95%, 96%, 97%, 98%, or 99% homology.

In certain embodiments, the attenuated PRV has one or more inactivated genes related to pathogenicity. An "inactivated" gene refers to a gene whose function is reduced or abolished due to lack or deletion of complete or partial sequences, or due to insertions or mutations in the gene. Examples of genes related to PRV pathogenicity include, without limitation, TK (for example, NCBI Gene ID: 2952559), PK (for example, NCBI Gene ID: 2952530 or 2952561), RR (for example, NCBI Gene ID: 2952535 or 2952536), dUTPase (for example, NCBI Gene ID: 2952537), gG (for example, NCBI Gene ID: 2952520), gC (for example, NCBI Gene ID: 2952505), gE (for example, NCBI Gene ID: 2952517), gD (for example, NCBI Gene ID: 2952521) and gI (for example, NCBI Gene ID: 2952516).

In certain embodiments, the attenuated PRV has one or more inactivated genes selected from the group consisting of TK, PK, RR, dUTPase, gG, gC, gE, gD and gI. In certain embodiments, the attenuated PRV has an inactivated gE gene. In certain embodiments, only gE gene is inactivated in the attenuated PRV. In certain embodiments, the attenuated PRV has an inactivated gE gene, and further has one or more inactivated genes related to pathogenicity, for example, TK, PK, RR, dUTPase, gG, gC, gD and/or gI.

The attenuated PRV vaccine can be obtained using methods known in the art. For example, an isolate of PRV wild type strain can be attenuated by passaging the virus in non-porcine cells or in egg embryos, or by culturing under an elevated temperature and/or in the presence of a mutagen. Many attenuated PRV vaccines are known in the art, for example, Bartha K61 strain (see, for example, Bartha, A. Experiments to reduce the virulence of Aujeszky's virus. Magyar allatorvosok lapja 16, 42-45 (1961)), BUK strain, NIA4 strain, Alfort strain, and VGNKI strain etc. These attenuated PRV vaccines can be used in the present disclosure. For example, the wild type or attenuated PRV strain may further be modified, such that one or more target genes related to pathogenicity are inactived yet the virus is still capable of replication. Many attenuated PRV vaccines obtained by genetic engineering are known in the art, for example, PRV-BUK-d13 strain (see, for example, Kit S. et al, Am. J. Vet. Res., 1985, 46 (6): 1359-1367), PRV dlgC/dlTK strain (see, for example, Kit S. et al, Am. J. Vet. Res., 1987, 48 (5): 780-793), S—PRV-002 (see, for example, U.S. Pat. No. 4,514,497), PRV783 strain (see, for example, Van Oirschot J T et al, Am. J. Vet. Res., 1984, 45 (10): 2099-2103), EL-001, and PRV376 etc.

In certain embodiments, the attenuated PRV lacks gE gene. In certain embodiments, the attenuated PRV has a microorganism deposit number of CGMCC No.: 5076 (such attenuated PRV strain is also referred to as PRV Bartha K61 strain herein).

In certain embodiments, the attenuated PRV further comprises one or more inactivated genes that do not affect viral replication or host infection. In certain embodiments, the attenuated PRV further comprises one or more heterogeneous genes that are not present in PRV genome. The inserted heterogeneous genes are useful in detection and/or diagnosis of the vaccines.

In certain embodiments, the vaccine composition further comprises a third porcine vaccine, wherein the PRRSV vaccine, the second porcine virus vaccine and the third porcine virus vaccine are substantially free from immuno-inhibition against each other. In certain embodiments, the third porcine vaccine can be selected from a CSFV vaccine and a PRV vaccine, provided that the second vaccine is different from the third vaccine.

In certain embodiments, the vaccine compositions comprise a PRRSV vaccine, a CSFV vaccine and a PRV vaccine, wherein the PRRSV vaccine, the CSFV vaccine and the PRV vaccine are substantially free from immuno-inhibition against each other. The three vaccines, when combined in a vaccine composition, do not substantially reduce antibody production and/or T cell subpopulation levels in a host in response to the PRRSV vaccine, the CSFV vaccine and/or the PRV vaccine. In certain embodiments, the PRRSV vaccine comprises PRRSV TJM strain. The CSFV vaccine comprises any of the attenuated CSFV provided herein, including but not limited to, CSFV C strain. The PRV vaccine comprises any of the attenuated PRV strain provided herein, for example but not limited to, PRV Bartha K61 strain.

In certain embodiments, the present disclosure provides a vaccine composition, comprising PRRSV TJM strain having a microorganism deposit No. of CGMCC NO. 3121, and CSFV C strain. In certain embodiments, the CSFV C strain is CSFV F16 having a microorganism deposit No. of CGMCC NO. 3891. PRRSV TJM strain and CSFV C strain (F16) do not show any immuno-inhibition or immune suppression against each other. Both vaccine strains have good safety, immunogenicity and specificity, and can provide effective protection against both the highly-pathogenic porcine reproductive and respiratory syndrome and classical swine fever, which are two of the major epidemics in pig herds.

In certain embodiments, the present disclosure provides a vaccine composition, comprising PRRSV TJM strain having a microorganism deposit No. of CGMCC NO. 3121, and PRV Bartha K61 strain with microorganism deposit No. of CGMCC NO. 5076. PRRSV TJM strain and PRV Bartha K61 strain do not show any immuno-inhibition or immune suppression between each other. Both vaccine strains have good safety, immunogenicity and specificity, and can provide effective protection against both the highly-pathogenic porcine reproductive and respiratory syndrome and pseudorabies, which are two of the major epidemics in pig herds.

In certain embodiments, the present disclosure provides a vaccine composition, comprising PRRSV TJM strain, CSFV C strain (F16) and PRV Bartha K61 strain. PRRSV TJM strain, CSFV C strain (F16) and PRV Bartha K61 strain do not show any immuno-inhibition or immune suppression among each other. The three vaccine strains have good safety, immunogenicity and specificity, and can provide effective protection against the highly-pathogenic porcine reproductive and respiratory syndrome, classical swine fever and pseudorabies, which are three of the major epidemics in pig herds.

The detailed deposit information of PRRSV TJM strain is as follows: Microorganism Deposit No.: CGMCC No. 3121; Taxonomic Name: Porcine Reproductive and Respiratory Syndrome Virus; Deposit Address: Institute of Microbiology, Chinese Academy of Sciences, NO. 1 West Beichen Road, Chaoyang District, Beijing, China; Deposit Unit: China General Microbiological Culture Collection Center; and Deposit Date: Jun. 15, 2009.

The detailed deposit information of CSFV C strain (F16) is as follows: Microorganism Deposit No.: CGMCC No. 3891; Taxonomic Name; Classical Swine Fever Virus; Deposit Address: Institute of Microbiology, Chinese Academy of Sciences, NO. 1 West Beichen Road, Chaoyang District, Beijing, China; Deposit Unit: China General Microbiological Culture Collection Center; and Deposit Date: May 27, 2010.

The detailed deposit information of PRV Bartha K61 strain is as follows: Microorganism Deposit No.: CGMCC No. 5076; Taxonomic Name: Pseudorabies Virus; Deposit Address: Institute of Microbiology, Chinese Academy of Sciences, NO. 1 West Beichen Road, Chaoyang District, Beijing, China; Deposit Unit: China General Microbiological Culture Collection Center; and Deposit Date: Jul. 21, 2011.

In certain embodiments, the vaccine composition provided herein comprises an immunologically effective amount of PRRSV vaccine, CSFV vaccine and/or PRV vaccine. The term "immunologically effective amount" as used herein, refers to an amount of a vaccine that is sufficient to induce a protective immune response in the host against the intended antigen or pathogen. For example, an immunologically effective amount may be sufficient to reduce or delay the onset of one or more symptoms of the infection, reduce morbidity and/or mortality of the infected host, induce a sufficient level of antibodies against the pathogen, increase levels of T cell sub-populations, and any combinations thereof. Characterization and/or quantification of the protective immune response can be carried out using methods known in the art, for example, by measuring antibody titers against the pathogen, and/or amount of T cell sub-populations, as described above, or by observing for clinical manifestations of the vaccinated pigs after virulent virus challenge.

The immunologically effective amount of a virus vaccine can be characterized in virus titer, for example, in 50% tissue culture infective dose ($TCID_{50}$). In certain embodiments, the immunologically effective amount of the PRRSV vaccine is at least $10^{3.0}$ $TCID_{50}$, $10^{3.5}$ $TCID_{50}$, $10^{4.0}$ $TCID_{50}$, $10^{4.5}$ $TCID_{50}$, $10^{5.0}$ $TCID_{50}$, or $10^{5.5}$ $TCID_{50}$. In certain embodiments, the immunologically effective amount of the PRRSV vaccine is at least $10^{4.5}$ $TCID_{50}$, at least $10^{5.0}$ $TCID_{50}$ or at least $10^{5.5}$ $TCID_{50}$. In certain embodiments, the vaccine compositions provided herein comprises about $10^{4.5}$ $TCID_{50}$ to about $10^{6.0}$ $TCID_{50}$, or about $10^{5.0}$ $TCID_{50}$ to about $10^{6.0}$ $TCID_{50}$ of the PRRSV vaccine.

In certain embodiments, the immunologically effective amount of the CSFV vaccine is at least $10^{0.5}$ FA-$TCID_{50}$ (fluorescent antibody—$TCID_{50}$), $10^{1.0}$ FA-$TCID_{50}$, $10^{1.5}$ FA-$TCID_{50}$, $10^{2.0}$ FA-$TCID_{50}$, $10^{2.5}$ FA-$TCID_{50}$, $10^{3.0}$ FA-$TCID_{50}$, $10^{3.5}$ FA-$TCID_{50}$, $10^{4.0}$ FA-$TCID_{50}$, $10^{4.5}$ FA-$TCID_{50}$, or $10^{5.0}$ FA-$TCID_{50}$. In certain embodiments, the immunologically effective amount of the CSFV vaccine is at least $10^{4.0}$ FA-$TCID_{50}$/ml. In certain embodiments, the vaccine compositions provided herein comprises about $10^{0.5}$ FA-$TCID_{50}$ to about $10^{5.0}$ FA-$TCID_{50}$, or about $10^{4.0}$ FA-$TCID_{50}$ to about $10^{5.0}$ FA-$TCID_{50}$ of the CSFV vaccine. The term "FA-TCID50" refers to a $TCID_{50}$ value determined by a method based on fluorescent antibody.

In certain embodiments, the immunologically effective amount of the CSFV vaccine is at least 2.5 RID, 3 RID, 5 RID, 10 RID, 30 RID, 100 RID, 150 RID, 300 RID, 750 RID, 1000 RID, 3000 RID, or 7500 RID.

In certain embodiments, the immunologically effective amount of the PRV vaccine is at least $10^{3.0}$ $TCID_{50}$, $10^{3.5}$ $TCID_{50}$, $10^{4.0}$ $TCID_{50}$, $10^{4.5}$ $TCID_{50}$, $10^{5.0}$ $TCID_{50}$, $10^{5.5}$ $TCID_{50}$ or $10^{6.0}$ $TCID_{50}$. In certain embodiments, the immunologically effective amount of the PRV vaccine is at least $10^{5.5}$ $TCID_{50}$, or at least $10^{6.0}$ $TCID_{50}$. In certain embodiments, the vaccine compositions provided herein comprises about $10^{5.0}$ $TCID_{50}$ to about $10^{6.5}$ $TCID_{50}$, or about $10^{5.5}$ $TCID_{50}$ to about $10^{6.5}$ $TCID_{50}$ of the PRV vaccine.

The $TCID_{50}$ of a virus vaccine can be determined using any suitable methods known in the art. For example, the virus vaccine (PRRSV vaccine and/or PRV vaccine) can be prepared as a virus solution, and 10-fold serial dilutions of the virus solution can be prepared and inoculated to a 96-well culture plate seeded with susceptible cells. Virus solutions of each dilution can be inoculated in 8 wells at 100 ul/well. The plates can be placed in an incubator at 37° C., with 5% $CO_2$, and cultured for 4-5 days. The cells are observed for cytopathic effects, and $TCID_{50}$ is calculated as the virus concentration at which 50% of the tissue culture shows cytopathic effects. A detailed description of the method can be found at Reed L J, Muench H, A simple method of estimating fifty percent end points. Am J Hyg 1938; 27:493-97.

CSFV is a virus that does not cause obvious cytopathic effects, and the $TCID_{50}$ is therefore determined by immunofluorescent method, or with rabbit infection study. In certain embodiments, the FA-$TCID_{50}$ for the CSFV vaccine is determined by an immunofluorescent method. Briefly, the CSFV vaccine strain is prepared as a solution containing 1 dose/ml, and 10-fold serial dilutions are prepared with DMEM culture medium supplemented with 3.5% serum. Dilutions containing $10^{-1}$, $10^{-2}$, $10^{-3}$, $10^{-4}$, and $10^{-5}$ of original virus samples are inoculated respectively to single layer of BT cells at 0.1 ml/well. After 3-4 days culture, the cells are fixed and contacted with a fluorescent monoclonal antibody of CSFV (for direct immunofluoresenct method). After 45-60 minutes reaction, the cells are observed for presence of fluorescence, which indicates for presence of virus. Alternatively, the fixed cells can be contacted with an unlabelled monoclonal antibody of CSFV (for indirect immunofluoresenct method), and after 45-60 minutes reaction, the cells are reacted with fluorescence-labeled secondary antibody for another 45-60 minutes. The cells are observed for presence of fluorescence which indicates the presence of the virus. FA-TCID50 is calculated in accordance with the Reed-Muench method (see, e.g Reed L J, Muench H, A simple method of estimating fifty percent end points. Am J Hyg 1938; 27:493-97).

In certain embodiments, the amount of the CSFV vaccine is determined by rabbit infectivity dose. Briefly, the CSFV vaccine strain is prepared as a solution containing 1 dose, and is then diluted 7500-fold to prepare the testing sample. 2 rabbits of 1.5-3 kg body weight are each injected with 1 ml testing sample, and body temperature is taken twice each day for the first 48 hours, and once every 6 hours thereafter. The body temperature reactions are monitored and graded according the below criteria: 1) typical fever reaction (++): the latency period is about 48-96 hours, the body temperature significantly rises, in which at least 3 temperatures rise beyond the normal temperature by at least 1° C. and last for 18-36 hours; 2) slightly fever reaction (+): the latency period is about 48-96 hours, the body temperature significantly rises, in which at least 2 temperatures rise beyond the normal temperature by at least 0.5° C. and last for 12-36 hours; 3) suspected fever reaction (±): the latency period is about 48-96 hours, the body temperature fluctuates, the elevated temperature lasts for less than 12 hours, or the latency period is at least 24 hours, and fever reaction is demonstrated within 48 hours, or after 96 to 120 hours; and 4) no fever reaction (−): body temperature is normal. The vaccine is determined as having an amount of 7500 RID, if the two testing rabbits both showed typical fever reaction (++), or one of the rabbits showed typical fever reaction (++) while the other showed slightly fever reaction (+). In case the rabbits showed other reactions that are difficult to characterize, the test can be repeated, but should not be repeated for more than 3 times.

The single virus vaccines can be mixed at a suitable ratio to provide the vaccine compositions described herein. For example, a single virus vaccine can be prepared as a virus solution containing the vaccine strain at a certain virus titer (e.g. a certain $TCID_{50}$), and two or more single virus vaccines are mixed at a suitable ratio to give a combination vaccine containing each single vaccine at a predetermined amount (e.g. $TCID_{50}$) or ratio.

In certain embodiments, in a combined vaccine composition comprising the PRRSV vaccine and the CSFV vaccine, the $TCID_{50}$ ratio of the PRRSV vaccine to the CSFV vaccine ranges from 10000:1 to 1:1, 1000:1 to 1:1, 100:1 to 1:1, 10:1 to 1:1, or 5:1 to 1:1. For example, the vaccine composition can comprise $10^{4.5}$ TCID50 of PRRSV vaccine, and $10^{0.5}$ FA-TCID50 of CSFV vaccine, or $10^{4.5}$ TCID50 of PRRSV vaccine, and $10^{3.5}$ FA-TCID50 of CSFV vaccine, or $10^{5.0}$ TCID50 of PRRSV vaccine, and $10^{4.0}$ FA-TCID50 of CSFV vaccine.

In certain embodiments, in a combined vaccine composition comprising the PRRSV vaccine and the PRV vaccine, the $TCID_{50}$ ratio of the PRRSV vaccine to the PRV vaccine ranges from 1:1 to 1:30, 1:1 to 1:25, 1:1 to 1:20, 1:1 to 1:15, 1:1 to 1:10, 1:1 to 1:9, 1:1 to 1:8, 1:1 to 1:7, 1:1 to 1:6, 1:1 to 1:5, 1:2 to 1:10, 1:3 to 1:10, 1:4 to 1:10, or 1:5 to 1:10. For example, the vaccine composition can comprise $10^{4.5}$ TCID50 of PRRSV vaccine, and $10^{5.5}$ TCID50 of PRV vaccine, or $10^{5.0}$ TCID50 of PRRSV vaccine, and $10^{5.5}$ TCID50 of PRV vaccine, or $10^{5.0}$ TCID50 of PRRSV vaccine, and $10^{6.5}$ TCID50 of PRV vaccine.

In certain embodiments, in a combined vaccine composition comprising the PRRSV vaccine, the CSFV vaccine and the PRV vaccine, the $TCID_{50}$ ratio of the PRRSV vaccine:the CSFV vaccine:the PRV vaccine is about $10^4$:1:$10^5$ to about 5:1:6. For example, the vaccine composition can comprise $10^{4.5}$ TCID50 of PRRSV vaccine, $10^{0.5}$ FA-TCID50 of CSFV vaccine and $10^{5.5}$ TCID50 of PRV vaccine. For another example, the vaccine composition can comprise $10^{4.5}$ TCID50 of PRRSV vaccine, $10^{4.0}$ FA-TCID50 of CSFV vaccine and $10^{5.5}$ TCID50 of PRV vaccine. For another example, the vaccine composition can comprise $10^{5.7}$ TCID50 of PRRSV vaccine, $10^{5.0}$ FA-TCID50 of CSFV vaccine and $10^{5.8}$ TCID50 of PRV vaccine. For another example, the vaccine composition can comprise $10^{6.0}$ TCID50 of PRRSV vaccine, $10^{5.0}$ FA-TCID50 of CSFV vaccine and $10^{6.5}$ TCID50 of PRV vaccine.

The vaccine compositions provided herein can further comprise an adjuvant. The adjuvant can protect the vaccine from in vivo degradation, and/or can non-specifically stimulate the immune system, thereby can be helpful to enhance the immunological response to the vaccine. Examples of adjuvants include, without limitation, mineral salts (e.g., aluminum hydroxide, aluminum phosphate, calcium hydroxide), water-in-oil emulsion (e.g., complete Freund's adjuvant, incomplete Freund's adjuvant, etc.), saponin adjuvants (e.g., Stimulon™, etc), derivatives of bacteria or micro-organisms (e.g., LPS, lipid A derivatives, etc) and micro-particles (e.g., poly-α-hydroxyacid, etc).

The vaccine composition provided herein can further comprise a cryoprotectant. The cryoprotectant can keep the biological products in good stability and reduce the damage to the biological activity of the vaccine during the process of lyophilization. Examples of the cryoprotectant include sucrose, L-sodium glutamate or lactalbumin hydrolysate, etc.

Methods for Preparation

In another aspect, the present disclosure provides methods for preparing the vaccine compositions provided herein, comprising: (a) collecting PRRSV vaccine strain, CSFV vaccine strain and/or PRV vaccine strain, which are cultivated in their respective susceptible cells, and (b) mixing two or more of the virus strains at a suitable $TCID_{50}$ ratio.

In certain embodiments, the step (a) comprises: inoculating the PRRSV vaccine strain, CSFV vaccine strain and/or PRV vaccine strain to their respective susceptible cells, culturing the cells to prepare seed viruses for vaccine production, inoculating the seed viruses to their respective susceptible cells, propagating the cells to obtain antigen solutions containing the respective viruses.

In certain embodiments, the PRRSV vaccine strain is an attenuated vaccine strain of the highly-pathogenic PRRSV. In certain embodiments, the PRRSV vaccine strain is PRRSV TJM strain.

In certain embodiments, the CSFV vaccine strain is an attenuated CSFV. In certain embodiments, the CSFV vaccine strain is CSFV C strain (F16).

In certain embodiments, the PRV vaccine strain is an attenuated PRV. In certain embodiments, the PRV vaccine strain is Bartha K61 strain.

In certain embodiments, the susceptible cells for the PRRSV vaccine strain include, without limitation, cell lines such as Marc-145 cell line, MA-104 cell line, Vero cell line or CL-2621 cell line, or primary cells such as PAM cells.

In certain embodiments, the susceptible cells for the CSFV vaccine strain include, without limitation, cell lines such as BT cell line, Vero cell line, MPK cell line, SK6 cell line, PK2a cell line, CPK cell line, RKC cell line, MDBK cell line, MDCK cell line, CRFK cell line, PT cell line and ST cell line, or primary cells such as BT cells. Both PT cell line and ST cell line are pig testis cell lines.

In certain embodiments, the susceptible cells for the PRV vaccine strain include, without limitation, passaging cell lines such as ST cell line (ATCC No.: CRL-1746), PK-15 cell line (ATCC No.: CCL-33), Marc-145 cell line (ATCC No.: CRL-12219), bovine kidney MDBK cell line (ATCC No.: CCL-22), bovine turbinate BT cell line (ATCC No.: CRL-1390), Vero cell line (ATCC No.: CCL-81), BHK-21 cell line (ATCC No.: CCL-10), pig kidney cell line (see, IBRS-2, e.g., DECASTRO, M. P. 1964. Behavior of foot and mouth disease virus in cell culture: susceptibility of the IB-RS-2 swine cell line. Arquivos Instituto Biologica 31: 63-78), and rabbit kidney RK cell line (ATCC No.: CCL-106); or primary cells such as chicken embryo fibroblast cells and pig kidney cells. Primary cells can be prepared using methods known in the art, for example by isolating tissues from animal and preparing cells.

In certain embodiments, the susceptible cells were cultured preferably at 33-37° C., in the presence of 5% $CO_2$. The methods of culturing the susceptible cells can comprise: passaging the cell line after digestion with EDTA-trypsin solution, continuing to cultivate the cell line in growth medium, when cells reach 90-100% confluence, they can be further passaged or inoculated with a seed virus. The method for cultivating the cell line is preferably any of the following: cultivating the cells in a roller bottle and allowing the cell density to reach $1\times10^6$/ml-$5\times10^6$/ml; or introducing an adherent carrier to a bioreactor for suspension cultivation and allowing the cell density to reach $5\times10^6$/ml-$1\times10^7$/ml, wherein the adherent carrier is preferably a microcarrier or paper.

In certain embodiments, the PRRSV vaccine strain is inoculated to its susceptible cells at a Multiplicity of Infection (MOI) of 0.01-0.5, the CSFV vaccine strain is inoculated to its susceptible cells at a MOI of 0.1-0.5, or the inoculation amount is 3%-5% virus of cell origin, and/or the PRV vaccine strain is inoculated to its susceptible cells at a MOI of 0.005-0.5.

In certain embodiments, the cells inoculated with the respective virus vaccine strain are cultivated for 3-5 days after the inoculation, and seed viruses for vaccine production can be harvested. For PRRSV strain, the seed virus is harvested when the cytopathic effect reaches 70%. For CSFV strain, the first harvest is performed by medium change at the $5^{th}$ day after the inoculation, and subsequent harvests are performed by medium change at 4-day intervals, provided that no more than five harvests are performed. For PRV strain, the cell culture medium containing the virus is harvested 2-3 days after the inoculation.

In certain embodiments, the seed virus for vaccine production has a suitable virus titer. For example, the seed virus for PRRSV TJM strain can be no less than $10^{7.0}$ $TCID_{50}$ virus per ml, the seed virus for CSFV C strain (F16) can be >100,000 rabbit infective dose per ml or no less than $10^{6.0}$ FA-$TCID_{50}$ virus per ml as measured by an immunofluorescence based assay, and/or the seed virus for PRV Bartha K61 strain can be no less than $10^{8.0}$ $TCID_{50}$ virus per ml.

In certain embodiments, the seed viruses are inoculated to their respective susceptible cells, and are propagated to obtain antigen solutions containing the respective viruses. In certain embodiments, the antigen solutions as obtained has a suitable virus content, for example, no less than $10^{7.0}$ $TCID_{50}$ virus per ml for the PRRSV TJM strain, >100,000 RID per ml or no less than $10^{6.0}$ FA-$TCID_{50}$ virus per ml as measured by an immunofluorescence-based assay for the CSFV C strain (F16), and/or no less than $10^{8.0}$ $TCID_{50}$ virus per ml for PRV Bartha K61 strain.

In certain embodiments, the step (b) comprises mixing the collected the PRRSV vaccine strain and the CSFV vaccine strain at a $TCID_{50}$ ratio from 10000:1 to 1:1. In certain embodiments, the step (b) comprises mixing the collected PRRSV vaccine virus with the PRV vaccine virus at a $TCID_{50}$ ratio from 1:1 to 1:30. In certain embodiments, the step (b) comprises mixing the collected PRRSV vaccine virus, the CSFV vaccine virus, and the PRV vaccine virus at a $TCID_{50}$ ratio of about $10^4$:1:$10^5$ to about 5:1:6.

In certain embodiments, the step (b) further comprises mixing the mixture of the collected virus solutions with a cryoprotectant. In certain embodiments, the mixture of the collected virus solutions is mixed with the cryoprotectant in a volume ratio of 75-80:25-20.

In another aspect, the present disclosure provides vaccine compositions prepared using the methods provided herein.

In another aspect, the present disclosure provides use of the vaccine compositions provided herein in the manufacture of a medicament for preventing or treating PRRS, CSF, and/or PR.

In another aspect, the present disclosure provides methods of immunizing a pig, comprising administering to the pig a vaccine composition provided herein.

In another aspect, the present disclosure provides CSFV vaccine strains, cultured in a cell line selected from the group consisting of ST, PK-15, Marc-145, MDBK, BT, Vero, BHK-21, porcine kidney cell line (IBRS-2), rabbit kidney cell line (RK), and chicken embryo fibroblast cell line, or a primary cell which is porcine kidney primary cells.

In another aspect, the present disclosure provides use of these cell lines in culturing a CSFV vaccine strain.

The present disclosure also provides a vaccine composition prepared using the preparation method described above, comprising a PRRSV vaccine and a CSFV vaccine.

The present disclosure also provides uses of the vaccine composition in manufacturing a biological product for preventing or treating porcine reproductive and respiratory syndrome and classical swine fever.

The combination vaccine provided herein shows significant efficacy in preventing highly-pathogenic porcine reproductive and respiratory syndrome and classical swine fever. The highly-pathogenic PRRSV strains and CSFV vaccine strains provided herein do not show any immunological suppression, and the combination vaccines prepared therefrom show no difference from each of their monovalent vaccines in terms of safety, immunogenicity, duration of immunity, immunological protection, and stability. The results of safety study show that, animals which received single dose, repetitive doses, over-dose inoculation of the vaccine show normal body temperature and spirit without any clinical symptoms. The results of efficacy study show that, the vaccine provided herein can provide significant protection to animals against the challenge of virulent strains of high pathogenic PRRSV and CSFV, and can effectively prevent infection of high pathogenic PRRSV and CSFV. The results of immunity duration study show that, the duration of immunity lasts for 6 months, which can ensure effective protection to pigs during the immunity period. The results of stability study show that, the vaccine can be stored at 2-8° C. for 18 months, which indicates its advantage in long shelf life and stable storage. The vaccines provided herein can be used to inoculate animals and prevent two diseases with one injection, thereby reduce the work load of vaccination and the immunization frequency, minimize the stress to the pig herds, and prevent immune tolerant and failure caused by frequent vaccination.

The present disclosure also provides a method for immunizing a pig, comprising administering the vaccine composition provided herein to the pig. The pigs can be immunized by, for example, injection. The immunization can be one single administration or repetitive administration of multiple doses. The methods for immunization or dosages can be adjusted by an experienced veterinary professional according to the actual conditions.

EXAMPLES

The following examples are intended to further illustrate the present inventions. The advantages and features of the present invention will become clear with the descriptions. However, these illustrations are merely exemplary, and should not be construed as limitations to the scope of the present disclosure.

General

Inoculation of vaccines was performed by injection into the neck muscle of the pigs. Virus challenge was performed by dripping the virus to the nose of the test pigs, and/or injecting the virus to the muscle of the test pigs. The FA-$TCID_{50}$ of CSFV virus amount was measured by immunofluorescence-based method.

FACS assay for T cells. The T cells were measured by flowcytometry method. Briefly, the blood samples were treated with anti-coagulant, followed by lysis of red blood cells. The treated samples were stained with FITC-CD8 monoclonal antibody (mAb), PE-CD4 mAb, PECy5-CD3 mAb, respectively (all antibodies were purchased from 51AB Biotech, Beijing). After 45-min incubation, the unreacted antibodies were removed, and the cells were suspended with PBS and analyzed on flow cytometer (BD FACSAria).

ELISA assay. The antibodies against PRRSV antigens, antibodies against CSFV antigens were measured by ELISA, using the respective detection kits purchased from Beijing IDEXX Yuanheng Laboratories Co., Ltd.

Part I

Preparation of the Vaccines

Example 1

Preparation of PRRSV Vaccines

Cell Passage and Culture

Marc-145 cells, which were used to culture the PRRSV vaccine strain TJM, were trypsinized and divided in 1:3. The cells were cultured at 37° C. in culture medium. After the cells formed a single layer, they were passaged or inoculated with a virus strain.

Propagation of the Seed Viruses in Cells

The vaccine strain TJM for highly virulent PRRSV was inoculated to Marc-145 cells in a MOI of 0.01-0.5. The inoculated cells were cultured for 3-5 days, and the virus solution was collected when the cytopathic effects (CPE) reached 70%. The collected virus solution was used as the seed virus of PRRSV TJM strain.

The seed virus was characterized according to Veterinary Pharmacopoeia of People's Republic of China. The seed virus was absent for bacteria, mold, or mycoplasma. The PRRSV seed virus solutions did not show adverse effects to pigs. The seed virus solution of PRRSV TJM strain contained no less than $10^{7.0}$ $TCID_{50}$ virus per 1 ml.

Propagation of the Virus Solution for Vaccine Production

Marc-145 cells were cultured to 90-100% confluent single layer. Cell culture medium was discarded, and cells were washed twice with PBS. The seed virus solution of PRRSV TJM strain was inoculated at MOI of 0.01-0.5. The inoculated cells were cultured for 3-5 days, and the virus solution was collected when the CPE reached 70%. The collected virus solution was used as the virus solution for vaccine production. Such virus solution was characterized, and was absent for bacteria, mold, or mycoplasma, and the virus solution of PRRSV TJM strain contained no less than $10^{7.0}$ $TCID_{50}$ virus per 1 ml. The virus solution was diluted appropriately to prepare PRRSV single vaccine, or mixed with other vaccines to prepare combined vaccines.

Example 2

Preparation of CSFV Vaccines

Cell Passage and Culture

The BT cells, which were used to culture the CSFV vaccine strain, were trypsinized and divided in 1:5. The cells were cultured at 37° C. in culture medium. After the cells formed a single layer, they were passaged or inoculated with a virus strain.

The CSFV C strain (F16) was prepared into a 0.3% virus solution, and was inoculated to a single layer of BT cells. The inoculated cells were cultured for 5 days, and the virus solution is collected as the seed virus of CSFV vaccine strain.

Characterization of the Seed Viruses

The seed viruses were characterized according to Veterinary Pharmacopoeia of People's Republic of China. The seed viruses were absent for bacteria, mold, or mycoplasma. The CSFV C strain (F16) were tested as a qualified seed virus solution, and showed no adverse effects to pigs. The seed virus solution of CSFV C strain (F16) contained >100,000 rabbit infective dose (RID), or no less than $10^{6.0}$ FA-$TCID_{50}$ virus per 1 ml virus solution as measured by an immunofluorescence-based method.

Propagation of the Virus Solution for Vaccine Production

BT cells were cultured to 90-100% confluent single layer. Cell culture medium was discarded, and cells were washed twice with PBS. The seed virus solution of CSFV C strain (F16) was inoculated at MOI of 0.1-0.5 or at an amount of 3%-5%. At the $5^{th}$ day after the inoculation, the first harvest is performed by medium change, and the subsequent harvests are performed at 4-day intervals, provided that no more than 5 harvests are performed. The virus solutions as collected were stored under −20° C. and used as the virus solution for vaccine production. Such virus solution was characterized, and the seed virus solution of CSFV C strain (F16) contained >100,000 RID, or no less than $10^{6.0}$ FA-$TCID_{50}$ virus per 1 ml virus solution as measured by an immunofluorescence-based method. The virus solution was diluted appropriately to prepare CSFV single vaccine, or mixed with other vaccines to prepare combined vaccines.

Example 3

Preparation of PRV Vaccines

Cell Passage and Culture

Marc-145 cells, MDBK cells and BT cells which were used to culture the PRV vaccine strain Bartha K61, were trypsinized and passaged respectively in cell growth medium. The cells were cultured at 37° C. in culture medium. After the cells formed a single layer, they were passaged or inoculated respectively with a virus strain.

Propagation of the Seed Virus in Cells

The PRV vaccine strain Bartha K61 was inoculated to a single layer of Marc-145 cells, MDBK cells or BT cells in MEM medium containing 2-4% bovine serum. The inoculated cells were cultured respectively for 2-3 days, and the virus solutions were collected as the seed virus of PRV vaccine strain.

Characterization of the Seed Viruses

The seed viruses were characterized. The PRV seed viruses were tested as a qualified seed solution, and did not show adverse effects to pigs. The seed virus solution of PRV strain contained no less than $10^{8.0}$ $TCID_{50}$ virus per 1 ml.

Propagation of the Virus Solution of the PRV Vaccine Strain

The PRV stain was inoculated to a confluent single layer of Marc-145 cells, MDBK cells or BT cells at MOI of 0.005-0.5 with maintenance medium added. The inoculated cells were cultured at 36-37° C. and the virus solution was collected when CPE reached 70%.

The amount of the virus solution was measured after freeze-thaw for 2 cycles. The seed virus solution contained no less than $10^{8.0}$ $TCID_{50}$ virus per 1 ml. The virus solution was characterized in accordance with the Veterinary Pharmacopoeia of People's Republic of China, and was absent for bacteria, mold, or mycoplasma. The qualified virus solutions were stored under −15° C. and used as the virus solution for vaccine production. The virus solution was diluted appropriately to prepare PRV single vaccine, or mixed with other vaccines to prepare combined vaccines.

Example 4

Preparation of a Combined Vaccine Composition for PRRSV and CSFV

Antigen solution was prepared by combining the virus solution of PRRSV TJM strain (prepared according to Example 1) and the virus solution of CSFV C strain (F16) (prepared according to Example 2).

Heat-resistant cryoprotectant was prepared by mixing sucrose, L-sodium glutamate, and lactalbumin hydrolysate in a suitable ratio, followed by autoclave.

75-80 of volume fraction of the antigen solution was mixed with 25-20 of volume fraction of the cryoprotectant, and the mixture was filed into ampoules in a predetermined amount. The ampoules were capped and were subject to low temperature and drying process to get freeze-dried vaccine composition. The vaccine composition was tested for sterility, safety, and efficacy.

In each dose of the combined PRRSV and CSFV vaccine as prepared, the amount of PRRSV TJM strain was $\geq 10^{5.0}$ $TCID_{50}$, and the amount of CSFV C strain (F16) was ≥7500 RID (or ≥750 RID, or ≥150 RID), or no less than $10^{4.0}$ FA-$TCID_{50}$ virus as measured by an immunofluorescence-based method.

The combined vaccine was characterized according to page 15, 19 and 20 of the appendix of Veterinary Pharmacopoeia of People's Republic of China. The combined vaccine was absent for bacteria, mold, mycoplasma and exogenous virus.

Example 5

Preparation of a Combined Vaccine Composition for PRRSV and PRV

Antigen solution was prepared by combining the virus solution of PRRSV TJM strain (prepared according to Example 1) and the virus solution of PRV Bartha K61 strain (prepared according to Example 3).

Heat-resistant cryoprotectant was prepared by mixing sucrose, L-sodium glutamate, and lactalbumin hydrolysate in a suitable ratio, followed by autoclave.

6-8 of volume fraction of the antigen solution was mixed with 2-4 of volume fraction of the cryoprotectant, and the mixture was filed into ampoules in a predetermined amount. The ampoules were capped and were subject to low temperature and drying process to get freeze-dried vaccine composition.

In each dose of the combined PRRSV and PRV vaccine as prepared, the amount of PRRSV TJM strain was $\geq 10^{5.0}$ $TCID_{50}$, and the amount of PRV Bartha K61 strain was $\geq 10^{5.5}$ $TCID_{50}$.

The combined vaccine was characterized according to page 15, 19 and 20 of the appendix of Veterinary Pharmacopoeia of People's Republic of China. The combined vaccine was absent for bacteria, mold, mycoplasma and exogenous virus.

Example 6

Preparation of a Combined Vaccine Composition for PRRSV, CSFV and PRV

Antigen solution was prepared by combining the virus solution of PRRSV TJM strain (prepared according to Example 1), the virus solution of CSFV C strain (F16) (prepared according to Example 2), and the virus solution of PRV Bartha K61 strain (prepared according to Example 3).

Heat-resistant cryoprotectant was prepared by mixing sucrose, L-sodium glutamate, and lactalbumin hydrolysate in a suitable ratio, followed by autoclave.

75-80 of volume fraction of the antigen solution was mixed with 25-20 of volume fraction of the cryoprotectant, and the mixture was filed into ampoules in a predetermined amount. The ampoules were freeze-dried to provide the vaccine composition. The vaccine composition was tested for sterility, safety, and efficacy.

In each dose of the combined PRRSV, CSFV and PRV vaccine as prepared, the amount of PRRSV TJM strain virus was $\geq 10^{5.0}$ $TCID_{50}$, the amount of CSFV C strain virus was ≥7500 RID (or ≥750 RID, ≥150 RID), or no less than $10^{4.0}$ FA-$TCID_{50}$ virus as measured by an immunofluorescence-based method and the amount of PRV Bartha K61 strain virus was $\geq 10^{5.5}$ $TCID_{50}$.

The combined vaccine was characterized according to page 15, 19 and 20 of the appendix of Veterinary Pharmacopoeia of People's Republic of China. The combined vaccine was absent for bacteria, mold, mycoplasma and exogenous virus.

Example 7

Gene Characterization of PRRSV TJM Strain

The PRRSV TJM strain contained in the virus solution as prepared according to Example 1, and in the combination vaccines as prepared according to Examples 4-6 was characterized by PCR, using primers specific to nsp2 of PRRSV (forward primer: 5'-GGCAAGAAGTTGAGGAAGT-3'; reverse primer: 5'-TGGCAGGTTGGTCACAGA-3'). PRRSV TJ strain was a positive control and water was a negative control.

Figure 5:
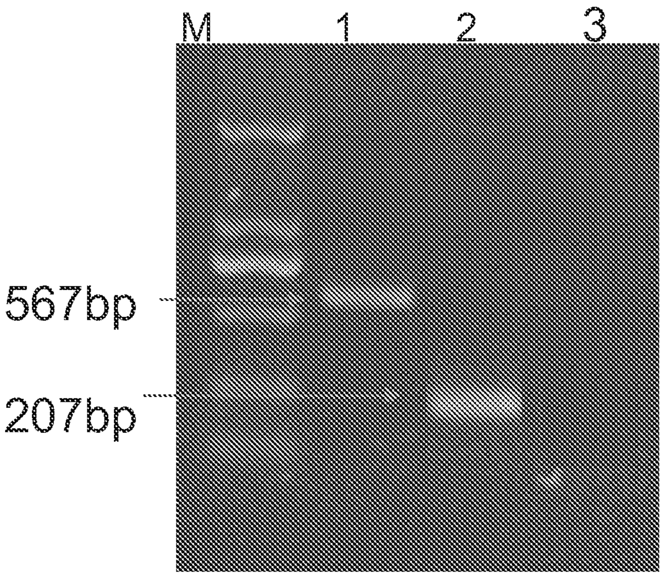
FIG. 5 shows the electrophoresis image of PRRSV TJM vaccine strain (lane 2), the highly-pathogenic PRRSV TJ virulent strain (lane 1), and water (lane 3, as negative control), respectively. M refers to the molecular weight marker.

The results showed a specific 207 bp band in the samples containing PRRSV TJM strain, as compared to a 567 bp band in the positive control containing PRRSV TJ strain (FIG. 5). The results confirmed that PRRSV TJM strain lacks 360 nucleotides in nsp2 gene, and further confirmed that the vaccines as prepared is not contaminated with PRRSV TJ strain.

Example 8

Gene Characterization of PRV Bartha K61 Strain

The PRV Bartha K61 strain contained in the virus solution as prepared according to Example 3, and in combination vaccine compositions as prepared according to Examples 5-6 was characterized by PCR, using primers specific to gE of PRV (forward primer: 5'-CGTCACGGTCACCAAGGAGC-3'; reverse primer: 5'-GCACAGCACGCAGAGCCAG-3'). PRV virulent strain (JL1 strain) was a positive control and water was a negative control.

Figure 6:
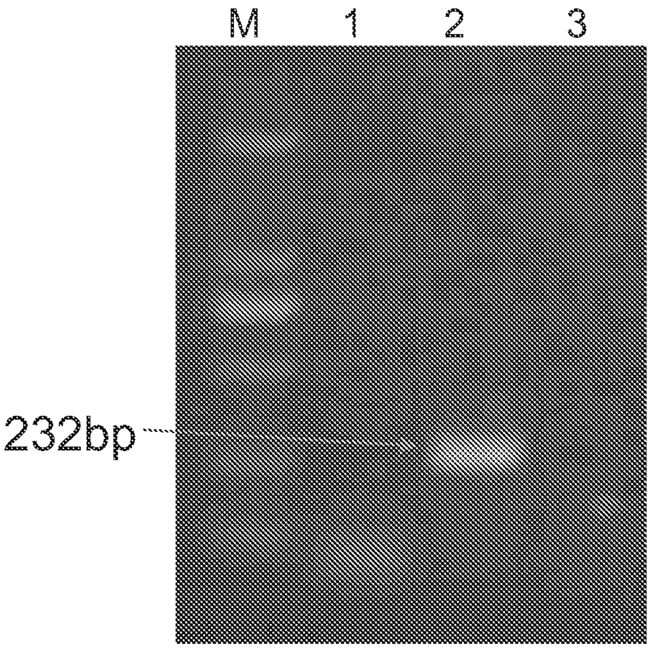
FIG. 6 shows the electrophoresis image of PRV vaccine strain (lane 1), virulent strain (lane 2), and water (lane 3, as negative control), respectively. M refers to the molecular weight marker.
Figure 7:
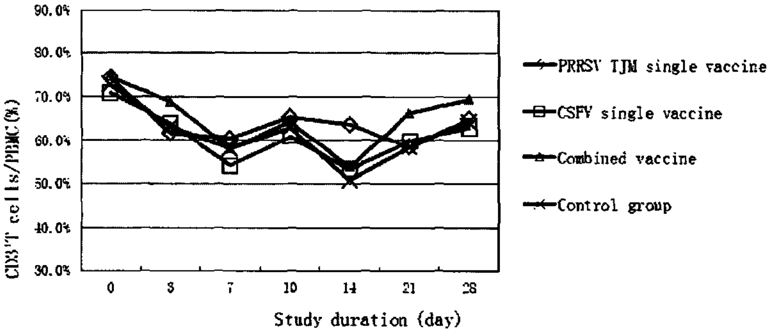
FIG. 7 shows the changes (%) in CD3+ T cells in test pigs vaccinated with PRRSV TJM single vaccine, CSFV C strain (F16) single vaccine, and combined vaccine, or negative control.
Figure 8:
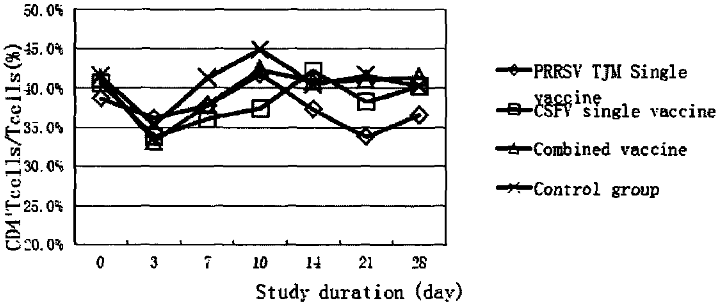
FIG. 8 shows the changes (%) in CD4+ T cells in test pigs vaccinated with PRRSV TJM single vaccine, CSFV C strain (F16) single vaccine, and combined vaccine, or negative control.
Figure 9:
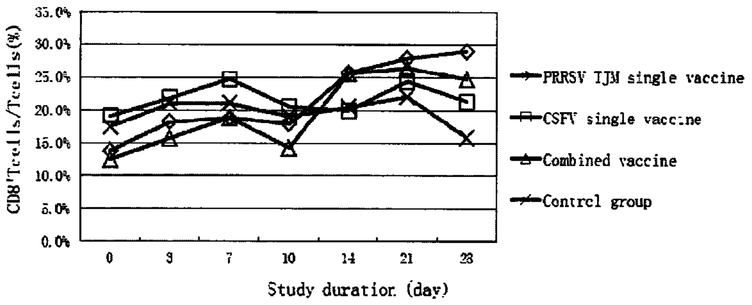
FIG. 9 shows the changes (%) in CD8+ T cells in test pigs vaccinated with PRRSV TJM single vaccine, CSFV C strain (F16) single vaccine, and combined vaccine, or negative control.
Figure 10:
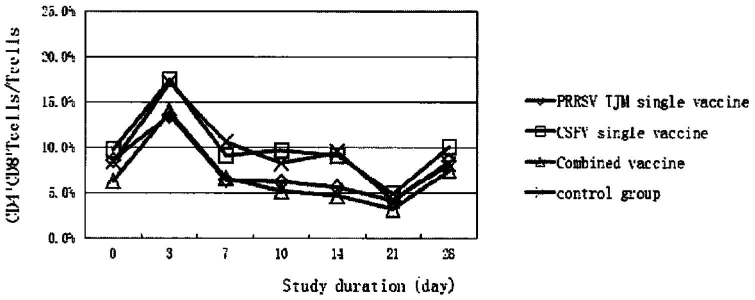
FIG. 10 shows the changes (%) in CD4+ CD8+ T cells in test pigs vaccinated with PRRSV TJM single vaccine, CSFV C strain (F16) single vaccine, combined vaccine for PRRSV and CSFV, or negative control.

According to the results, no band was found in the samples containing PRV Bartha K61 strain, as compared to a 232 bp band in PRV virulent strain (FIG. 6).

The results confirmed that PRV Bartha K61 strain contains deletion in gE gene, and further confirmed that the vaccines as prepared is not contaminated with PRV virulent strain.

Part II

Efficacy Studies

Example 9

Determination of Minimum Immunologically Effective Dose for PRRSV TJM Strain 25 healthy weaning pigs were used in the study. The pigs were negative for highly-pathogenic PRRSV, in terms of both antigen and antibody. The pigs were randomized in 5 groups. Group I to VI were inoculated with different doses of PRRSV TJM strain, while Group V was kept as negative control (Table 1). Pigs were challenged with virulent PRRSV TJ strain, and protection rates were calculated after the study. According to Table 1, PRRSV TJM strain at $10^{4.5}$ TCID50 or higher amount was sufficient to induce protective immunity in pigs, with a protection rate of 4/5.

TABLE 1

| Group | No. of pigs | Vaccination dosage/pig | Virus challenge dosage/pig | No. of sick/No. of tested | No. of dead/No. of tested | Protection rates |
|---|---|---|---|---|---|---|
| I | 5 | $10^{5.5}$ $TCID_{50}$ | $2 \times 10^{4.0}$-$2 \times 10^{4.5}$ $TCID_{50}$ | 1/5 | 0/5 | 4/5 |
| II | 5 | $10^{4.5}$ $TCID_{50}$ | $2 \times 10^{4.0}$-$2 \times 10^{4.5}$ $TCID_{50}$ | 1/5 | 0/5 | 4/5 |
| III | 5 | $10^{3.5}$ $TCID_{50}$ | $2 \times 10^{4.0}$-$2 \times 10^{4.5}$ $TCID_{50}$ | 3/5 | 0/5 | 2/5 |
| IV | 5 | $10^{2.5}$ $TCID_{50}$ | $2 \times 10^{4.0}$-$2 \times 10^{4.5}$ $TCID_{50}$ | 5/5 | 1/5 | 0/5 |
| V | 5 | PBS | $2 \times 10^{4.0}$-$2 \times 10^{4.5}$ $TCID_{50}$ | 5/5 | 2/5 | 0/5 |

Example 10

Determination of Minimum Immunologically Effective Dose for CSFV C Strain (F16)

28 healthy weaning pigs were used in the study. The pigs were negative for CSFV, in terms of both antigen and antibody. The pigs were randomized in 6 groups. Group I to V were inoculated with different doses of CSFV C strain (F16), while Group VI was kept as negative control (Table 2). Pigs were challenged with virulent CSFV Shimen strain, and protection rates were calculated after the study. According to Table 2, CSFV C strain (F16) at $10^{0.5}$ TCID50 or higher amount was sufficient to induce protective immunity in pigs, with a protection rate of 5/5.

TABLE 2

| Group | No. of pigs | Vaccination dosage/pig | Virus challenge dosage/pig | No. of sick/No. of tested | No. of dead/No. of tested | Protection rates |
|---|---|---|---|---|---|---|
| I | 5 | $10^{4.5}$ FA $TCID_{50}$ | $10^{6.0}$ MLD | 0/5 | 0/5 | 5/5 |
| II | 5 | $10^{3.5}$ FA $TCID_{50}$ | $10^{6.0}$ MLD | 0/5 | 0/5 | 5/5 |
| III | 5 | $10^{2.5}$ FA $TCID_{50}$ | $10^{6.0}$ MLD | 0/5 | 0/5 | 5/5 |
| IV | 5 | $10^{1.5}$ FA $TCID_{50}$ | $10^{6.0}$ MLD | 0/5 | 0/5 | 5/5 |
| V | 5 | $10^{0.5}$ FA $TCID_{50}$ | $10^{6.0}$ MLD | 0/5 | 0/5 | 5/5 |
| VI | 3 | PBS | $10^{6.0}$ MLD | 3/3 | 3/3 | 0/3 |

MLD: Minimum lethal dose.

Example 11

Determination of Minimum Immunologically Effective Dose for Combined Vaccine of PRRSV TJM Strain and CSFV C Strain (F16)

40 healthy piglets were used in the study. The pigs were negative for both highly-pathogenic PRRSV and CSFV, in terms of both antigen and antibody. The pigs were randomized in 4 groups. Groups I to III groups were inoculated with different doses of the combined vaccines of PRRSV TJM strain and CSFV C strain (F16), while Group IV was kept as a negative control. Half of the pigs in each group were challenged with PRRSV TJ strain, and the other half were challenged with CSFV Shimen strain. Protection rates were calculated after the study.

According to Table 3, combined vaccine containing $10^{4.5}$ TCID50 of PRRSV TJM and $10^{3.5}$ FA-TCID50 of CSFV C strain (F16) was sufficient to induce protective immunity in pigs (Tables 3 and 4). In particular, CSFV C strain (F16) demonstrated 100% protection in all dosages as tested in the combined vaccine, indicating that the immune response to CSFV C strain (F16) was not suppressed by PRRSV TJM strain. Moreover, in view of the extremely low immunologically effective dosage of CSFV C strain (F16) as demonstrated in Example 10, lower dosages of CSFV C strain (F16) can be used in the combined vaccine without reducing the protection rate.

TABLE 3

| Group | No. of pigs | Vaccination dosage/pig | PRRSV TJ challenge dosage/pig | No. of sick/ No. of tested | No. of dead/ No. of tested | Protection rates |
|---|---|---|---|---|---|---|
| I | 5 | PRRSV TJM: $10^{5.5}$ $TCID_{50}$; CSFV C strain (F16): $10^{4.5}$ FA-$TCID_{50}$ | $2 \times 10^{4.0}$-$2 \times 10^{4.5}$ $TCID_{50}$ | 0/5 | 0/5 | 5/5 |
| II | 5 | PRRSV TJM: $10^{4.5}$ $TCID_{50}$; CSFV C strain (F16): $10^{3.5}$ FA-$TCID_{50}$ | $2 \times 10^{4.0}$-$2 \times 10^{4.5}$ $TCID_{50}$ | 0/5 | 0/5 | 5/5 |
| III | 5 | PRRSV TJM: $10^{3.5}$ $TCID_{50}$; CSFV C strain (F16): $10^{2.5}$ FA-$TCID_{50}$ | $2 \times 10^{4.0}$-$2 \times 10^{4.5}$ $TCID_{50}$ | 2/5 | 0/5 | 3/5 |
| IV | 5 | PBS | $2 \times 10^{4.0}$-$2 \times 10^{4.5}$ $TCID_{50}$ | 5/5 | 4/5 | 0/5 |

TABLE 4

| Group | No. of pigs | Vaccination dosage/pig | CSFV Shimen challenge dosage/pig | No. of sick/ No. of tested | No. of dead/ No. of tested | Protection rates |
|---|---|---|---|---|---|---|
| I | 5 | PRRSV TJM: $10^{5.5}$ $TCID_{50}$; CSFV C strain (F16): $10^{4.5}$ FA-$TCID_{50}$ | $10^{6.0}$ MLD | 0/5 | 0/5 | 5/5 |
| II | 5 | PRRSV TJM: $10^{4.5}$ $TCID_{50}$; CSFV C strain (F16): $10^{3.5}$ FA-$TCID_{50}$ | $10^{6.0}$ MLD | 0/5 | 0/5 | 5/5 |
| III | 5 | PRRSV TJM: $10^{3.5}$ $TCID_{50}$; CSFV C strain (F16): $10^{2.5}$ FA-$TCID_{50}$ | $10^{6.0}$ MLD | 0/5 | 0/5 | 5/5 |
| IV | 5 | PBS | $10^{6.0}$ MLD | 5/5 | 5/5 | 0/5 |

Example 12

Combined PRRSV TJM Strain and CSFV C Strain (F16) does not have Immuno-Inhibition 30 healthy pigs aged 21-28 days were used in the study. The pigs were negative for both highly-pathogenic PRRSV and CSFV, in terms of both antigen and antibody. The pigs were randomized in 7 groups, with 5 pigs in each of Groups I to V, 3 pigs in Group VI and 2 pigs in Group VII (Table 5). Each pig was inoculated with 1 ml of the testing sample, or not inoculated at all (i.e. Group VII), according to the study design shown in Table 5.

TABLE 5

| Group | No. of pigs | Testing sample | Amount | Vaccine dose |
|---|---|---|---|---|
| I | 5 | PRRSV TJM | 1 ml | $10^{5.0}$ TCID$_{50}$/ml |
| II | 5 | CSFV C strain (F16) | 1 ml | 7500 RID/ml (or $10^{4.0}$ FA-TCID$_{50}$/ml) |
| III | 5 | PRRSV TJM + CSFV C strain (F16) | 1 ml | PRRSV: $10^{5.0}$ TCID$_{50}$/ml CSFV: 7500RID (or $10^{4.0}$ FA-TCID$_{50}$/ml) |
| IV | 5 | PRRSV TJM + CSFV C strain (F16) | 1 ml | PRRSV: $10^{5.0}$ TCID$_{50}$/ml CSFV: 7500RID (or $10^{4.0}$ FA-TCID$_{50}$/ml) |
| V | 5 | PBS | 1 ml | N/A |
| VI | 3 | PBS | 1 ml | N/A |
| VII | 2 | N/A | N/A | N/A |

"RID": rabbit infective dose;
"N/A": No inoculation or vaccination was performed.

Rectal temperatures of the pigs were taken each day from the $3^{rd}$ day before the vaccination until the $14^{th}$ day after the vaccination. Body weights were measured every 7 days. The pigs were also under close clinical observation. Blood samples were taken from each of the pigs in the study at the $3^{rd}$ day before the vaccination, the 0 day, $3^{rd}$ day, $7^{th}$ day, $10^{th}$ day, $14^{th}$ day, $21^{st}$ day, and $28^{th}$ day after the vaccination, respectively. Each blood sample was divided into two portions. One was treated with an anticoagulant, and was used for detection of CD3$^+$, CD4$^+$, CD8$^+$ and CD4$^+$ CD8$^+$ T cells. The other portion was treated with a coagulant, and was used for antibody titer assay.

Figure 11:
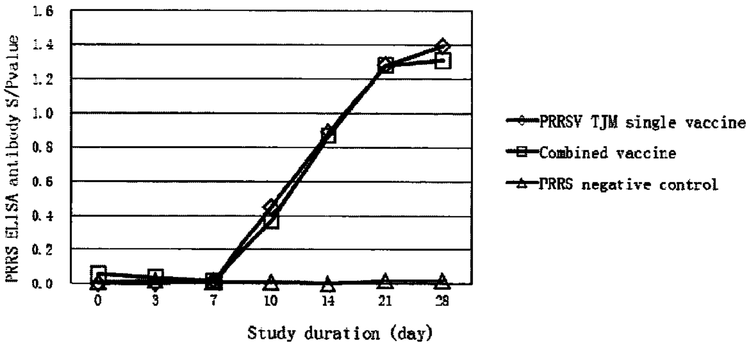
FIG. 11 shows the PRRSV antibody titers (determined by ELISA) in pigs vaccinated with PRRSV TJM single vaccine, combined vaccine for PRRSV TJM and CSFV C strain (F16), or negative control.
Figure 12:
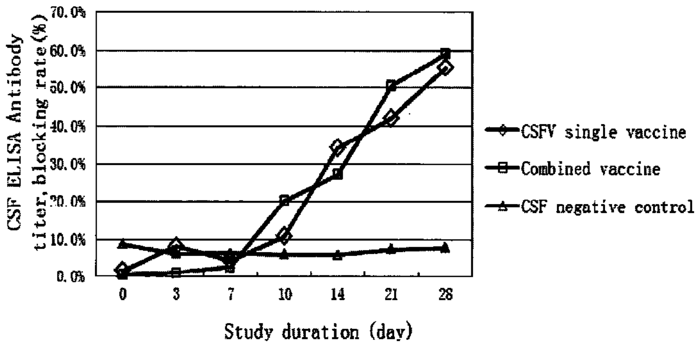
FIG. 12 shows the CSFV antibody titers (determined by ELISA) in pigs vaccinated with CSFV C strain (F16) single vaccine, combined vaccine for PRRSV TJM and CSFV C strain (F16), or negative control.

Results showed that the changes in CD3$^+$, CD4$^+$, CD8$^+$ and CD4$^+$CD8$^+$ T cells in the vaccinated pigs were similar to those observed in the pigs of the control groups (FIGS. 7-10). After vaccination with the combined vaccines, pigs in Groups III and IV produced antibodies against both viruses, and such antibody productions did not interfere with each other (FIGS. 11-12). The kinetics of PRRSV antibody production for pigs in Groups III and IV was similar to those for pigs in Group I, and the kinetics for CSFV antibody production for pigs in Groups III and IV was similar to those for pigs in Group II. The results showed that, vaccination of PRRSV TJM strain does not inhibit the immunological response against CSFV C strain (F16), and vice versa.

Figure 13:
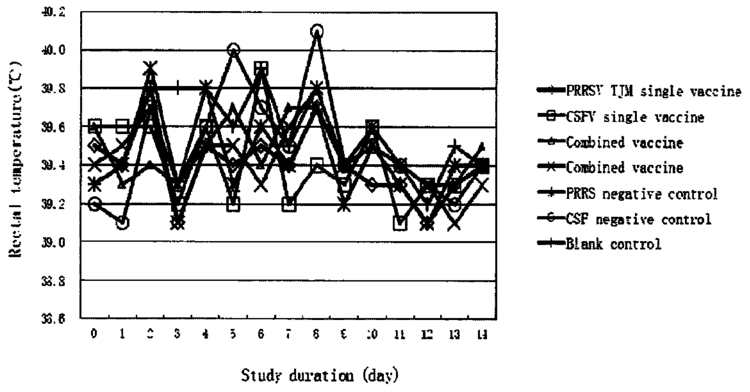
FIG. 13 shows the rectal temperatures of pigs after vaccination with PRRSV TJM single vaccine, CSFV C strain (F16) single vaccine, combined vaccine for PRRSV TJM and CSFV C strain (F16), or negative controls.

The rectal temperatures and the body weights of the pigs in each group do not show significant difference (FIG. 13).

At the $28^{th}$ day after the vaccination, the pigs were challenged with virulent viruses, according to the study design shown in Table 6. After the virus challenge, rectal temperatures of the pigs were taken each day, and the pigs were observed for clinical manifestations including appetite, breathing, and spirits. Blood samples were taken from each of the pigs at the 0 day, $3^{rd}$ day, $7^{th}$ day, $10^{th}$ day, and $14^{th}$ day respectively, after the virus challenge, and were treated with an anticoagulant for detection of CD3$^+$, CD4$^+$, CD8$^+$ and CD4$^+$CD8$^+$ T cells. Blood samples were also taken on the day of virus challenge and each other day after the challenge, for isolation of PRRSV virus and CSFV virus, and determination of presence of viremia. Clinical protection rates, morbidity (i.e. number of sick pigs/number of tested pigs), and mortality (i.e. number of dead pigs/number of tested pigs) were calculated for each group of animals 14 days after the virus challenge study, and the results are shown in Table 6.

TABLE 6

| Group | Pig No. | Challenge sample | Challenge dose/pig | No. of sick/ No. of tested | No. of dead/ No. of tested | Protection Rate |
|---|---|---|---|---|---|---|
| I | 5 | PRRSV TJ | $2 \times 10^{4.0}$-$2 \times 10^{4.5}$ TCID$_{50}$ | 0/5 | 0/5 | 5/5 |
| II | 5 | CSFV Shimen | $10^{6.0}$ MLD | 0/5 | 0/5 | 5/5 |
| III | 5 | PRRSV TJ | $2 \times 10^{4.0}$-$2 \times 10^{4.5}$ TCID$_{50}$ | 0/5 | 0/5 | 5/5 |
| IV | 5 | CSFV Shimen | $10^{6.0}$ MLD | 0/5 | 0/5 | 5/5 |
| V | 5 | PRRSV TJ | $2 \times 10^{4.0}$-$2 \times 10^{4.5}$ TCID$_{50}$ | 5/5 | 3/5 | 0/5 |
| VI | 3 | CSFV Shimen | $10^{6.0}$ MLD | 3/3 | 3/3 | 0/3 |
| VII | 2 | N/A | N/A | N/A | N/A | N/A |

"MLD": minimum lethal dose;
"N/A": No inoculation or vaccination was performed.

Figure 14:
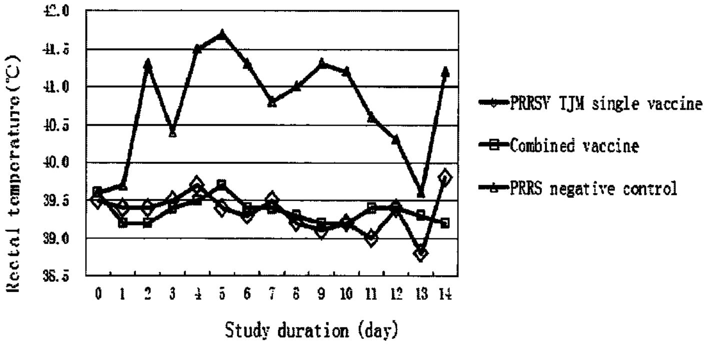
FIG. 14 shows the rectal temperatures of pigs after challenge with PRRSV virulent viruses, the pigs were vaccinated with PRRSV TJM single vaccine, combined vaccine for PRRSV TJM and CSFV C strain (F16), or negative control.
Figure 15:
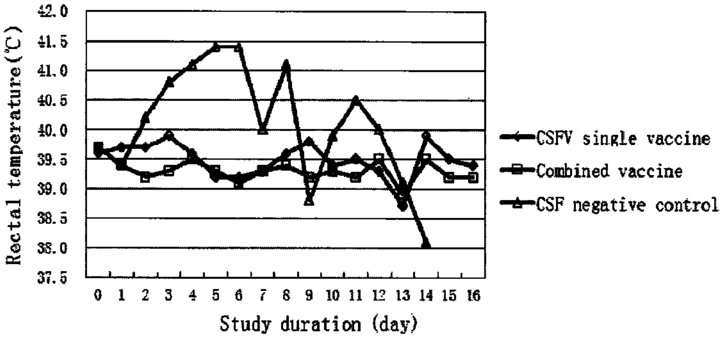
FIG. 15 shows the rectal temperatures of pigs after challenge with CSFV virulent viruses, the pigs were vaccinated with CSFV C strain (F16) single vaccine, combined vaccine for PRRSV TJM and CSFV C strain (F16), or negative control.
Figure 16:
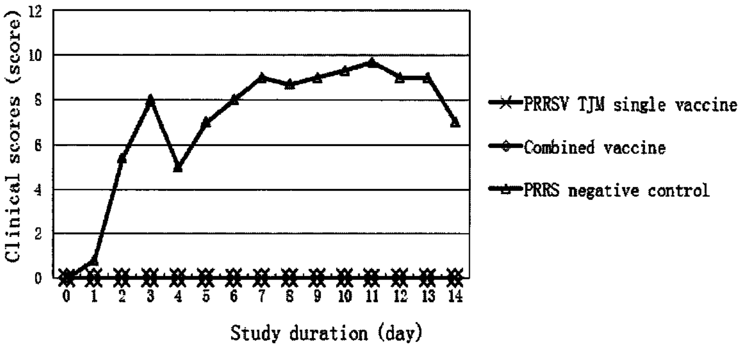
FIG. 16 shows the clinical symptom scores of pigs after challenge with PRRSV virulent viruses, the pigs were vaccinated with PRRSV TJM single vaccine, combined vaccine for PRRSV TJM and CSFV C strain (F16), or negative control.
Figure 17:
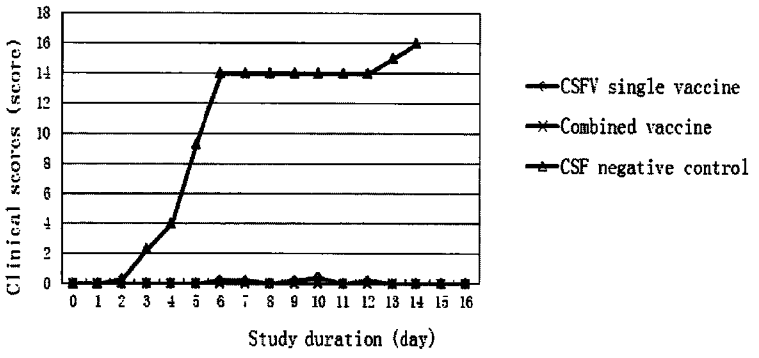
FIG. 17 shows the clinical symptom scores of pigs after challenge with CSFV virulent viruses, the pigs were vaccinated with CSFV C strain (F16) single vaccine, combined vaccine for PRRSV TJM and CSFV C strain (F16), or negative control.
Figure 18:
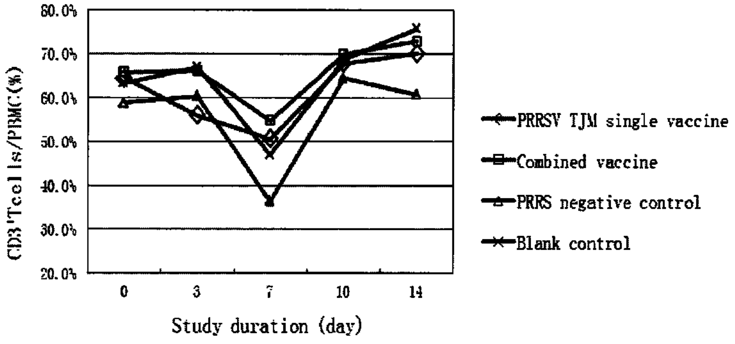
FIG. 18 shows the changes (%) in CD3+ T cells in pigs after challenge with PRRSV virulent viruses, the pigs were vaccinated with PRRSV TJM single vaccine, combined vaccine for PRRSV TJM and CSFV C strain (F16), or negative control.
Figure 19:
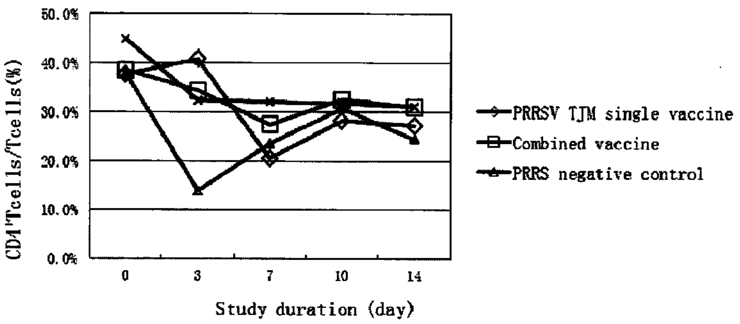
FIG. 19 shows the changes (%) in CD4+ T cells after challenge with PRRSV virulent viruses.
Figure 20:
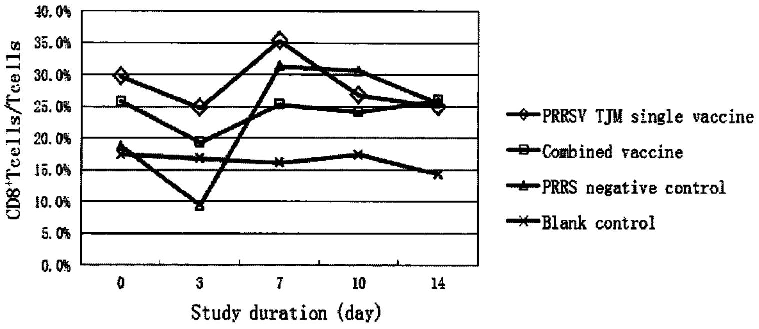
FIG. 20 shows the changes (%) in CD8+ T cells after challenge with PRRSV virulent viruses.
Figure 21:
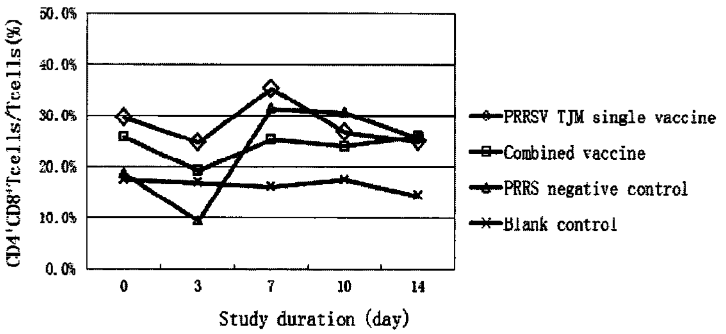
FIG. 21 shows the changes (%) in CD4+ CD8+ T cells after challenge with PRRSV virulent viruses.
Figure 22:
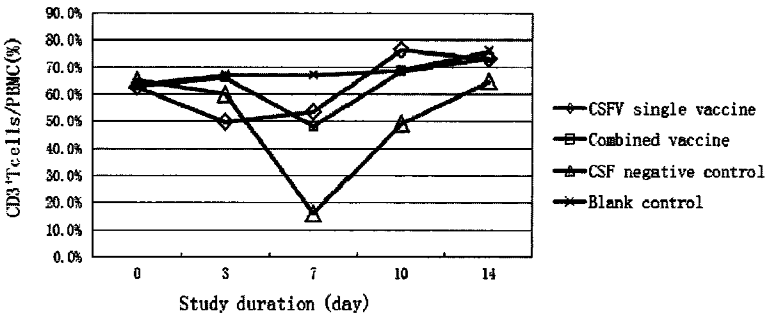
FIG. 22 shows the changes (%) in CD3+ T cells after challenge with CSFV virulent viruses, the pigs were vaccinated with CSFV C strain (F16) single vaccine, combined vaccine for PRRSV and CSFV, or negative control.
Figure 23:
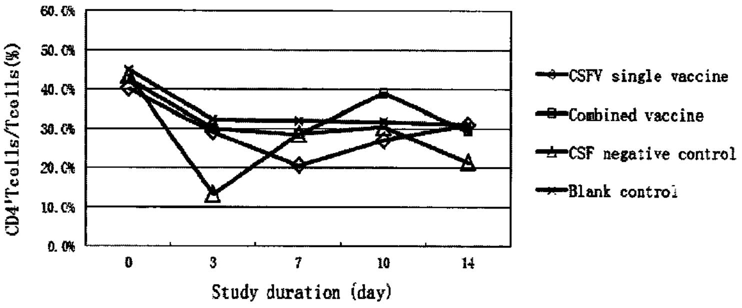
FIG. 23 shows the changes (%) in CD4+ T cells after challenge with CSFV virulent viruses.
Figure 24:
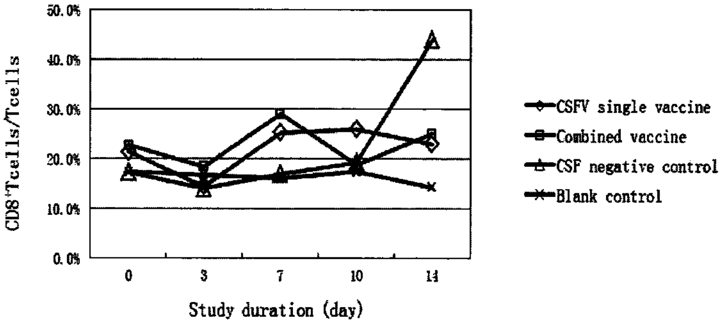
FIG. 24 shows the changes (%) in CD8+ T cells after challenge with CSFV virulent viruses.
Figure 25:
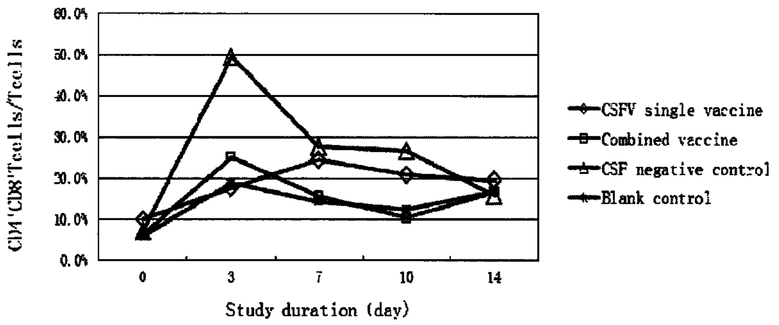
FIG. 25 shows the changes (%) in CD4+ CD8+ T cells after challenge with CSFV virulent viruses.

Results showed that, after the virus challenge, body temperatures were elevated in non-vaccinated pigs of Groups V and VI, but not in vaccinated pigs of Groups I-IV (FIGS. 14-15). Pigs in Group V demonstrated clinical symptoms for highly-pathogenic PRRS such as low spirit, stress in breath, red skin, etc. Pigs in Group VI demonstrated significant symptoms for classical swine fever, including low spirit, constipation followed by diarrhea, red skin, etc. No pigs in the vaccinated groups demonstrated such clinical symptoms (FIGS. 16-17).

After the virus challenge, non-vaccinated pigs of Groups V and VI showed a significant drop in CD3$^+$, CD4$^+$, CD8$^+$ and CD4$^+$CD8$^+$ T cells, and started to die from $7^{th}$ day after the virus challenge. On the other hand, pigs vaccinated with the combined vaccines or the single vaccines did not show such significant drop in T cells, and the T cell profiles were comparable to the healthy pigs in the blank control group.

This indicated that the vaccines were effective in eliciting cellular immune responses. In addition, the pigs vaccinated with the combined vaccines and the pig with the single vaccines showed similar changes in $CD3^+$, $CD4^+$, $CD8^+$ and $CD4^+CD8^+$ T cells, which indicated that the combined vaccines were free from immuno-inhibition against each other (FIGS. 18-25).

After challenge with highly virulent PRRSV, non-vaccinated pigs of Group V started to develop viremia from day 2, which lasted up to 11 days. However, pigs vaccinated with the combined vaccines or the PRRSV single vaccine did not develop viremia until day 4, which lasted up to 5 days. This indicated that the combined vaccines and the single vaccine both provided effective protection against infection of highly-pathogenic PRRSV, and the combined vaccines were free from immuno-inhibition against each other.

After challenge with virulent CSFV, all pigs in Group VI developed viremia, but none of the vaccinated pigs developed viremia. This indicated that the combined vaccines and the single vaccine both provided effective protection against infection of virulent CSFV, and the combined vaccines were free from immuno-inhibition against each other.

Example 13

Efficacy Study of the 2-Combo Vaccine for PRRSV and CSFV

Efficacy study was carried out using three batches of the lab-made 2-combo vaccine for PRRSV and CSFV (Batch No.: 200904, 200905, and 200906), prepared according to Example 4.

28 healthy pigs, negative for both highly virulent PRRSV and CSFV, in terms of both antigen and antibody, were used in the study for each batch of the 2-combo vaccine sample. The pigs were randomized in 6 groups, with 5 pigs in each of Groups I to IV and Group VI, and 3 pigs in Group V. Each group of pigs was inoculated with its respective testing sample, and at the $28^{th}$ day after the vaccination, the pigs were challenged with a virulent virus, in accordance with the study design shown in Table 7.

The CSFV virus challenge study ended at the $16^{th}$ day after the challenge, and the PRRSV virus challenge study ended at the $21^{st}$ day after the challenge. The protection rates were calculated and the results are shown in Table 7. All of the three batches of the 2-combo vaccines of PRRSV and CSFV demonstrated good protection against the challenge from highly virulent PRRSV or CSFV. The protection from the 2-combo vaccine showed no significant difference from the single vaccine controls. The un-vaccinated pigs all showed evident clinical symptoms of infection.

Example 14

Immuno-Duration Study of the 2-Combo Vaccine for PRRSV and CSFV

Immuno-duration study was carried out using the 2-combo vaccine for PRRSV and CSFV (as prepared according to Example 4). PRRSV single vaccine (as prepared according to Example 1) and CSFV single vaccine (as prepared according to Example 2) were used as controls.

56 healthy pigs were used in the immuno-duration study. All pigs were negative for PRRSV and CSFV, in terms of both antigen and antibody. The pigs were randomized into 6 groups, and were inoculated with the respective testing samples as shown in Table 8. Blood samples were collected for determination of antibody titers at 1st, 2nd, 3rd, 4th, 5th, or 6th months post vaccination.

At the 3rd and the 6th month post vaccination, respectively, half of the animals were taken from each study group. These animals were challenged with the respective virulent virus, as shown in Table 8.

Results showed that (see Table 8), the 2-combo vaccines provided effective protection to pigs against virus challenge 6 months after the vaccination, and therefore supported a 6-month immuno-duration period. The immuno-duration of the 2-combo vaccine was found comparable to that of the single vaccines.

TABLE 7

| Group | Testing sample and dosage | Virus challenge and dosage/pig | Protective rates 200904 | 200905 | 200906 |
|---|---|---|---|---|---|
| I | 2-combo vaccine, 1 ml/pig: PRRSV TJM ($10^{5.0}$ $TCID_{50}$/ml) + CSFV C strain (F16) (7500 RID/ml, or $10^{4.0}$ FA-$TCID_{50}$/ml) | CSFV Shimen: $10^{6.0}$ MLD | 5/5 | 5/5 | 5/5 |
| II | 2-combo vaccine, 1 ml/pig: PRRSV TJM ($10^{5.0}$ $TCID_{50}$/ml) + CSFV C strain (F16) (7500RID/ml, or $10^{4.0}$ FA-$TCID_{50}$/ml) | PRRSV TJ, $2 \times 10^{4.0}$-$2 \times 10^{4.5}$ $TCID_{50}$ | 4/5 | 4/5 | 5/5 |
| III | CSFV C strain (F16), 1 ml/pig: 7500 RID/ml, or $10^{4.0}$ FA-$TCID_{50}$/ml | CSFV Shimen: $10^{6.0}$ MLD | 5/5 | 5/5 | 5/5 |
| IV | PRRSV TJM, 1 ml/pig: $10^{5.0}$ $TCID_{50}$/ml | PRRSV TJ, $2 \times 10^{4.0}$-$2 \times 10^{4.5}$ $TCID_{50}$ | 5/5 | 4/5 | 4/5 |
| V | PBS, 1 ml/pig | CSFV Shimen: $10^{6.0}$ MLD | 0/3 | 0/3 | 0/3 |
| VI | PBS, 1 ml/pig | PRRSV TJ, $2 \times 10^{4.0}$-$2 \times 10^{4.5}$ $TCID_{5.0}$ | 0/5 | 0/5 | 0/5 |

"RID": rabbit infective dose;

"MLD": minimum lethal dose;

TABLE 8

| Group | Vaccine inoculation and dosage | Virus challenge and dosage/ pig | Protective rates 3-mon | Protective rates 6-mon |
|---|---|---|---|---|
| I | 2-combo vaccine, 1 ml/pig: PRRSV TJM ($10^{5.0}$ $TCID_{50}$/ml) + CSFV C strain (F16) (7500 RID, or $10^{4.0}$ FA-$TCID_{50}$/ml) | CSFV Shimen strain $10^{6.0}$ MLD | 5/5 | 5/5 |
| II | 2-combo vaccine, 1 ml/pig: PRRSV TJM ($10^{5.0}$ $TCID_{50}$/ml) + CSFV C strain (F16) (7500 RID, or $10^{4.0}$ FA-$TCID_{50}$/ml) | PRRSV TJ strain, $2 \times 10^{4.0}$-$2 \times 10^{4.5}$ $TCID_{50}$ | 5/5 | 5/5 |
| III | CSFV C strain (F16), 1 ml/pig: 7500 RID, or $10^{4.0}$ FA-$TCID_{50}$/ml | CSFV Shimen strain $10^{6.0}$ MLD | 5/5 | 5/5 |
| IV | PRRSV TJM, 1 ml/pig: $10^{5.0}$ $TCID_{50}$/ml | PRRSV TJ strain, $2 \times 10^{4.0}$-$2 \times 10^{4.5}$ $TCID_{50}$ | 4/5 | 4/5 |
| V | PBS, 1 ml/pig: | CSFV Shimen strain $10^{6.0}$ MLD | 0/3 | 0/3 |
| VI | PBS, 1 ml/pig: | PRRSV TJ strain, $2 \times 10^{4.0}$-$2 \times 10^{4.5}$ $TCID_{50}$ | 0/5 | 0/5 |

"RID": rabbit infective dose;
"MLD": minimum lethal dose;

Example 15

Combined PRRSV TJM Strain and PRV Bartha K61 Strain does not have Immuno-Inhibition 2-combo vaccine for PRRSV TJM and PRV Bartha K61 (prepared according to Example 5) was used in the study. Pigs aged 4-5 weeks were randomized in 4 groups, with 4 pigs in each group. All pigs were negative for PRRSV and PRV, in terms of both antigen and antibody.

Pigs were inoculated with the respective testing sample, according to the study design shown in Table 9. The second vaccination was performed one week after the first vaccination.

TABLE 9

| Group | First vaccination | Second vaccination |
|---|---|---|
| I | PRRSV TJM, 1 ml/pig: $10^{5.0}$ $TCID_{50}$/ml | PRV Bartha K61, 1 ml: $10^{5.5}$ $TCID_{50}$/ml |
| II | N/A | 2-combo vaccine, 1 ml: PRRSV TJM ($10^{5.0}$ $TCID_{50}$/ml) + PRV Bartha K61($10^{5.5}$ $TCID_{50}$/ml) |
| III | N/A | PRV Bartha K61, 1 ml ($10^{5.5}$ $TCID_{50}$/ml) |
| IV | N/A | PBS |

"N/A": No inoculation or vaccination was performed.

After the vaccination, blood samples of the pigs were collected each week, until the $28^{th}$ day after the vaccination. The blood samples were treated and detected for antibody titers against PRV.

Figure 26:
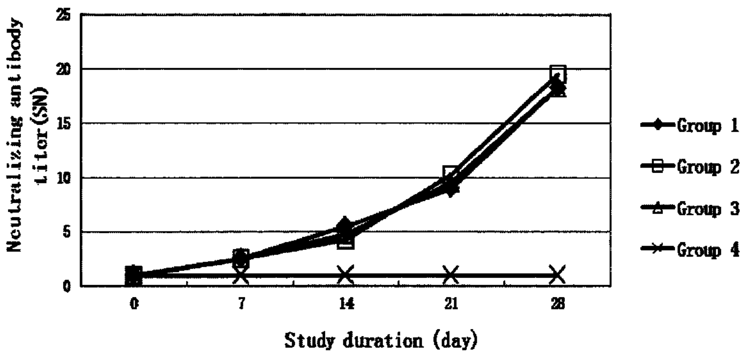
FIG. 26 shows the titer of anti-PRV neutralizing antibody after the vaccination with PRRSV and PRV. Group I was inoculated with PRRSV TJM single vaccine and PRV Bartha K61 single vaccine sequentially, group II was inoculated with 2-combo live vaccine, group III was inoculated with PRV Bartha K61 single vaccine, group IV was only inoculated with sterile PBS.
Figure 27:
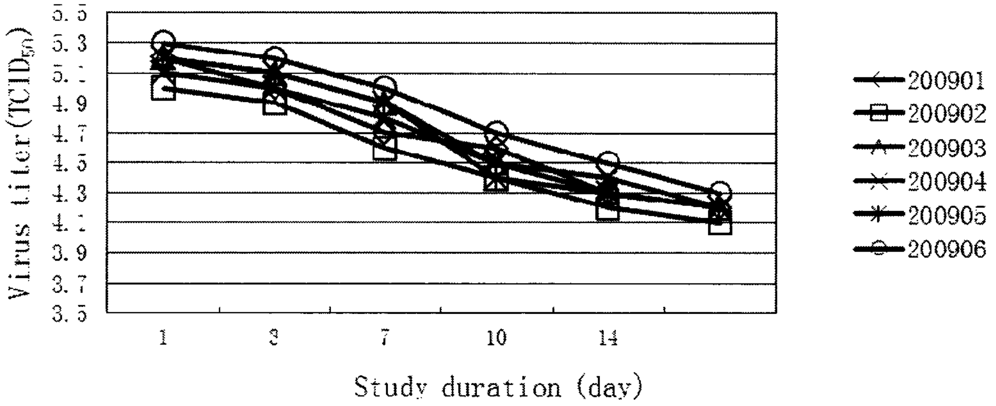
FIG. 27 shows the virus titers of CSFV C strain (F16) in the CSFV single vaccine and in the 2-combo vaccine (PRRSV and CSFV) after storage at 37° C. for 14 days. 200904, 200905 and 200906 represent three batches of 2-combo vaccine, and 200901, 200902 and 200903 represent three batches of PRRSV TJM single vaccine.
Figure 28:
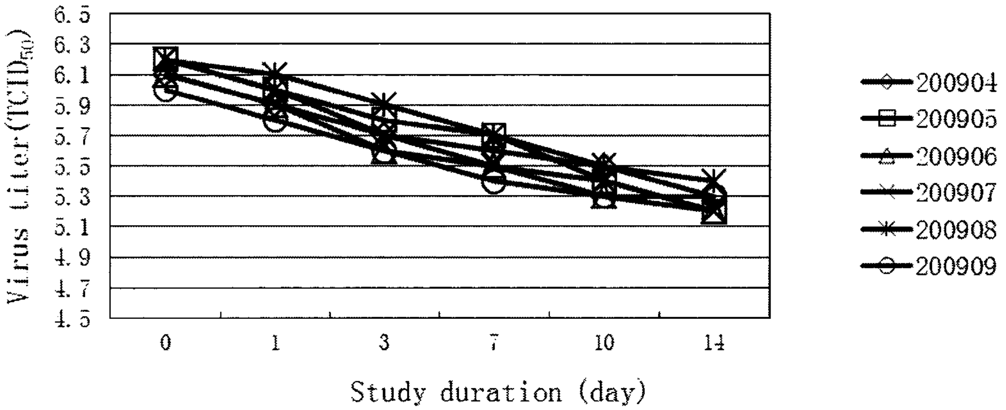
FIG. 28 shows the virus titers of PRRSV TJM strain in the PRRSV single vaccine and in the 2-combo vaccine (PRRSV and CSFV) after storage at 37° C. for 14 days. 200904, 200905 and 200906 represent three batches of 2-combo vaccine, and 200907, 200908 and 200909 represent three batches of CSFV C strain (F16).
Figure 29:
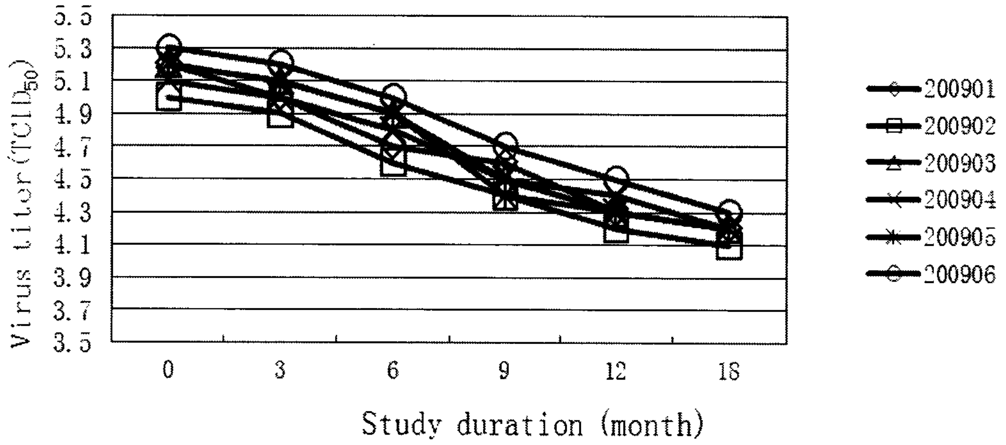
FIG. 29 shows the virus titers of CSFV C strain (F16) in the CSFV single vaccine and in the 2-combo vaccine (PRRSV and CSFV) after storage at 2-8° C. for 18 months.

Results showed that (FIG. 26), the PRV antibody titer was not significantly different among Groups I to III. This suggested that PRRSV TJM strain did not have immuno-inhibition against the PRV vaccine. PRRSV TJM strain did not affect the PRV antibody titer when administered separately or as a combined vaccine with PRV. The 2-combo vaccine for PRRSV and PRV had an efficacy comparable to that of a PRV single vaccine.

Example 16

Efficacy Study of the Combined PRRSV and PRV Vaccine

Efficacy study was carried out using three batches of the 2-combo vaccines for PRRSV and PRV, prepared according to Example 5.

Pigs aged 4-5 weeks were randomized into 4 groups, with 10 pigs in each group. Groups I to III were injected with one dose of a respective batch of 2-combo vaccine. Each dose of the vaccine contained $10^{50}$ $TCID_{50}$/ml PRRSV TJM strain and $10^{5.5}$ $TCID_{50}$/ml PRV Bartha K61 strain. Group IV was a control group and was injected with 1 ml MEM medium.

After the vaccination, the pigs were observed for clinical manifestations and adverse effects. The blood of the pigs was collected each week, and serum was separated for characterization of the antibody titers. The body weight of the pigs was measured every week.

4 weeks after the vaccination, 5 pigs in each group were challenged with PRRSV TJ strain at a dose of $2\times10^{4.0}$-$2\times10^{4.5}$ $TCID_{50}$, and the other 5 pigs were challenged with PRV virulent strain (JL1 strain) at a dose of $10^{3.0}$-$10^{3.5}$ $TCID_{50}$. After the virus challenge, the pigs were observed for clinical manifestations including appetite and spirit. Rectal temperatures of the pigs were taken each day. Blood samples and nasal swabs were collected for virus characterization.

Results showed that, vaccinated pigs in Groups I to III showed normal temperature and were in good spirits and good appetites after vaccination. After the virus challenge, the vaccinated pigs were protected with a protective rate of above 4/5, while all of the non-vaccinated pigs in the control group developed infection, and had a mortality rate of 2/5 from virulent PRRSV challenge and 3/5 from virulent PRV challenge. The results suggested that the 2-combo vaccine for PRRSV and PRV had good efficacy against the challenge of both viruses, and were effective in preventing infection of PRRSV and PRV.

Example 17

Combined PRRSV TJM Strain, CSFV C Strain and PRV Bartha K61 Strain does not have Immuno-Inhibition 46 healthy pigs aged 21-28 days were used in the study. The pigs were negative for highly virulent PRRSV, CSFV and PRV, in terms of both antigen and antibody. The pigs were randomized into 10 groups, with 5 pigs in each of Groups I to VII and Group IX, and 3 pigs in each of Groups VIII and X. The pigs were inoculated with 1 ml of the testing sample as assigned, or not inoculated at all (i.e. Group X), according to the study design shown in Table 10.

TABLE 10

| Group | No. of pigs | Testing sample | Vaccine dose |
|---|---|---|---|
| I | 5 | PRRSV TJM, 1 ml/pig | $10^{5.0}$ $TCID_{50}$/ml |
| II | 5 | CSFV C strain (F16), 1 ml/pig | 7500 RID/ml (or $10^{4.0}$ FA-$TCID_{50}$/ml) |
| III | 5 | PRV Bartha K61, 1 ml/pig | $10^{5.5}$ $TCID_{50}$/ml |
| IV | 5 | 3-combo vaccine, 1 ml/pig: PRRSV TJM + CSFV C strain (F16) + PRV Bartha K61 | PRRSV: $10^{5.0}$ $TCID_{50}$/ml CSFV: 7500 RID/ml (or $10^{4.0}$ FA-$TCID_{50}$/ml) PRV: $10^{5.5}$ $TCID_{50}$/ml |
| V | 5 | 3-combo vaccine, 1 ml/pig: PRRSV TJM + CSFV C strain (F16) + PRV Bartha K61 | PRRSV: $10^{5.0}$ $TCID_{50}$/ml CSFV: 7500 RID/ml (or $10^{4.0}$ FA-$TCID_{50}$/ml) PRV: $10^{5.5}$ $TCID_{50}$/ml |
| VI | 5 | 3-combo vaccine, 1 ml/pig: PRRSV TJM + CSFV C strain (F16) + PRV Bartha K61 | PRRSV: $10^{5.0}$ $TCID_{50}$/ml CSFV: 7500 RID/ml (or $10^{4.0}$ FA-$TCID_{50}$/ml) PRV: $10^{5.5}$ $TCID_{50}$/ml |
| VII | 5 | PBS, 1 ml/pig | N/A |
| VIII | 3 | PBS, 1 ml/pig | N/A |
| IX | 5 | PBS, 1 ml/pig | N/A |
| X | 3 | N/A | N/A |

"RID": rabbit infective dose.

"N/A": No inoculation or vaccination was performed.

Rectal temperatures of the pigs were taken each day from the 3rd day before the vaccination until the 7th day after the vaccination. The pigs were also under close clinical observation. Blood samples were taken from each of the pigs in the study at the 3rd day before the vaccination, the 0 day, 3rd day, 7th day, 10th day, 14th day, 21st day, 28th day, 31st day, 35th day, 38th day, and 42nd day after the vaccination, respectively. Each blood sample was divided into two portions. One was treated with an anticoagulant, and was used for detection of $CD3^+$, $CD4^+$, and $CD8^+$ T cell detection. The other portion was treated with a coagulant, and was used for antibody titer assay.

At the 28th day after the vaccination, the pigs were challenged with virulent viruses, according to the study design shown in Table 11. After the virus challenge, rectal temperatures of the pigs were taken each day, and the pigs were observed for clinical manifestations including appetite, breathing, and spirits. The PRRSV challenge study ended at 21st day after the virus challenge, and the CSFV challenge study ended at the 16th day after the virus challenge. Clinical protection rates, morbidity (i.e. number of sick pigs/number of tested pigs), and mortality (i.e. number of dead pigs/number of tested pigs) were calculated for each group after the virus challenge study, and the results are shown in Table 11.

TABLE 11

| Group | Pig No. | Challenge sample | Challenge dose/pig | No. of sick/No. of tested | No. of dead/ No. of tested | Protection Rate |
|---|---|---|---|---|---|---|
| I | 5 | PRRSV TJ | $2 \times 10^{4.0}$-$2 \times 10^{4.5}$ $TCID_{50}$ | 0/5 | 0/5 | 5/5 |
| II | 5 | CSFV Shimen | $10^{6.0}$ MLD | 0/5 | 0/5 | 5/5 |
| III | 5 | PRV JL1 | $10^{3.0}$-$10^{3.5}$ $TCID_{50}$ | 0/5 | 0/5 | 5/5 |
| IV | 5 | PRRSV TJ | $2 \times 10^{4.0}$-$2 \times 10^{4.5}$ $TCID_{50}$ | 0/5 | 0/5 | 5/5 |
| V | 5 | CSFV Shimen | $10^{6.0}$ MLD | 0/5 | 0/5 | 5/5 |
| VI | 5 | PRV JL1 | $10^{3.0}$-$10^{3.5}$ $TCID_{50}$ | 0/5 | 0/5 | 5/5 |
| VII | 5 | PRRSV TJ | $2 \times 10^{4.0}$-$2 \times 10^{4.5}$ $TCID_{50}$ | 5/5 | 3/5 | 0/5 |
| VIII | 3 | CSFV Shimen | $10^{6.0}$ MLD | 3/3 | 3/3 | 0/3 |
| IX | 5 | PRV JL1 | $10^{3.0}$-$10^{3.5}$ $TCID_{50}$ | 5/5 | 5/5 | 0/5 |
| X | 3 | N/A | N/A | N/A | N/A | N/A |

"MLD": minimum lethal dose;

"N/A": No inoculation or vaccination was performed.

Results showed that PRRSV TJM strain, when combined with the CSFV C strain and the PRV Bartha K61 strain, provided effective protection against challenge of all three virulent viruses. The combined vaccines showed comparable efficacy to that of each single vaccines, suggesting that the combined vaccines were free from immuno-inhibition against each other.

Example 18

Efficacy Study for Combined PRRSV TJM Strain, CSFV C Strain and PRV Bartha K61 Strain Efficacy study was carried out using three batches of the lab-made 3-combo vaccine (batch No.: 031-01, 031-02, and 031-03), prepared according to Example 6.

43 healthy pigs, negative for highly virulent PRRSV, CSFV and PRV, in terms of both antigen and antibody, were used in the study. The pigs were randomized in 9 groups, with 5 pigs in each of Groups I to VI, Group VIII and Group IX, and 3 pigs in Group VII. Each group of pigs was inoculated with its respective testing sample, and at the $28^{th}$ day after the vaccination, the pigs were challenged with a respective virulent virus, in accordance with the study design shown in Table 12. The PRRSV challenge study ended at $21^{st}$ day after the virus challenge, the CSFV challenge study ended at the $16^{th}$ day after the virus challenge, and the PRV challenge study ended at the $14^{th}$ day after the virus challenge. Clinical protective rates, morbidity, and mortality were calculated for each group of animals after the virus challenge study, and the results were shown in Table 12.

TABLE 12

| Group | Vaccine inoculation and dosage | Virus challenge and dosage/pig | Protective rates Batch No. 1 | Batch No. 2 | Batch No. 3 |
|---|---|---|---|---|---|
| I | 3-combo vaccine, 1 ml/pig: PRRSV TJM ($10^{5.0}$ $TCID_{50}$/ml) + CSFV C strain (F16) (7500 RID, or $10^{4.0}$ FA-$TCID_{50}$/ml) + PRV Bartha K61 ($10^{5.5}$ $TCID_{50}$/ml) | CSFV Shimen: $10^{6.0}$ MLD | 5/5 | 5/5 | 5/5 |
| II | 3-combo vaccine, 1 ml/pig: PRRSV TJM ($10^{5.0}$ $TCID_{50}$/ml) + CSFV C strain (F16) (7500 RID, or $10^{4.0}$ FA-$TCID_{50}$/ml) + PRV Bartha K61 ($10^{5.5}$ $TCID_{50}$/ml) | PRRSV TJ, $2 \times 10^{4.0}$-$2 \times 10^{4.5}$ $TCID_{50}$ | 4/5 | 4/5 | 5/5 |
| III | 3-combo vaccine, 1 ml/pig: PRRSV TJM ($10^{5.0}$ $TCID_{50}$/ml) + CSFV C strain (F16) (7500 RID, or $10^{4.0}$ FA-$TCID_{50}$/ml) + PRV Bartha K61 ($10^{5.5}$ $TCID_{50}$/ml) | PRV JL1: $10^{3.0}$-$10^{3.5}$ $TCID_{50}$ | 5/5 | 4/5 | 5/5 |
| IV | CSFV C strain (F16), 1 ml/pig: 7500 RID, or $10^{4.0}$ FA-$TCID_{50}$/ml | CSFV Shimen: $10^{6.0}$ MLD | 5/5 | 5/5 | 5/5 |
| V | PRRSV TJM, 1 ml/pig: $10^{5.0}$ $TCID_{50}$/ml | PRRSV TJ, $2 \times 10^{4.0}$-$2 \times 10^{4.5}$ $TCID_{50}$ | 5/5 | 4/5 | 4/5 |
| VI | PRV Bartha K61, 1 ml/pig: $10^{5.5}$ $TCID_{50}$/ml | PRV JL1: $10^{3.0}$-$10^{3.5}$ $TCID_{50}$ | 4/5 | 4/5 | 5/5 |
| VII | PBS, 1 ml/pig | CSFV Shimen: $10^{6.0}$ MLD | 0/3 | 0/3 | 0/3 |
| VIII | PBS, 1 ml/pig | PRRSV TJ, $2 \times 10^{4.0}$-$2 \times 10^{4.5}$ $TCID_{50}$ | 0/5 | 0/5 | 0/5 |
| IX | PBS, 1 ml/pig | PRV JL1: $10^{3.0}$-$10^{3.5}$ $TCID_{50}$ | 0/5 | 0/5 | 0/5 |

"RID": rabbit infective dose;

"MLD": minimum lethal dose;

The three batches of the 3-combo vaccines of PRRSV, CSFV and PRV all demonstrated good protection against challenge from highly virulent PRRSV, CSFV or PRV, while the negative controls all showed evident clinical symptoms of infection. The protection from the 3-combo vaccine showed no significant difference from the single vaccine controls.

Example 19

Immuno-Duration Study for Combined PRRSV TJM Strain, CSFV C Strain and PRV Bartha K61 Strain Immuno-duration study was carried out using three batches of the lab-made 3-combo vaccine (batch No.: 031-01, 031-02, and 031-03), prepared according to Example 6.

86 healthy pigs were used in the immuno-duration study. The pigs were negative for highly virulent PRRSV, CSFV and PRV, in terms of both antigen and antibody. The pigs were randomized into 9 groups, with 6 pigs in Group VII, and 10 pigs in each of the remaining groups. The pigs received vaccination or nothing according to the study design shown in Table 13. Blood samples were collected for determination of antibody titers at $1^{st}$, $2^{nd}$, $3^{rd}$, $4^{th}$, $5^{th}$, or $6^{th}$ month post vaccination.

At 3 months and 6 months post vaccination, respectively, half of the animals were taken from each study group and were challenged with the respective virulent virus, as shown in Table 13.

Results showed that (see Table 13), the 3-combo vaccines provided effective protection to pigs against virus challenge 6 months after the vaccination, and therefore supported a 6-month immuno-duration period. The immuno-duration of the 3-combo vaccines was found comparable to each of the single vaccines.

Part III

Safety Studies

Example 20

Safety Study of the Combined PRRSV and CSFV Vaccine

Safety study was carried out using three batches of the lab-made 2-combo vaccine for PRRSV and CSFV (batch No.: 200904, 200905, and 200906), as prepared according to Example 4.

The study included a single dose safety study, repetitive dose safety study, over-dose safety study on target age pigs, over-dose safety study on under-age pigs, and over-dose safety study on pigs of different breeds.

The results showed, after vaccination, pigs in each study group showed normal temperature, were in good spirits and good appetites. No systemic or local adverse effects were observed. Over-dose administration of the combination vaccines was shown to be safe to under-age pigs, and also to pigs of different breeds.

TABLE 13

| Group | Vaccine inoculation and dosage | Virus challenge and dosage/pig | Protective rates 3-mon | Protective rates 6-mon |
|---|---|---|---|---|
| I | 3-combo vaccine, 1 ml/pig: PRRSV TJM ($10^{5.0}$ $TCID_{50}$/ml) + CSFV C strain (F16) (7500 RID, or $10^{4.0}$ FA-$TCID_{50}$/ml) + PRV Bartha K61 ($10^{5.5}$ $TCID_{50}$/ml) | CSFV Shimen: $10^{6.0}$ MLD | 5/5 | 5/5 |
| II | 3-combo vaccine, 1 ml/pig: PRRSV TJM ($10^{5.0}$ $TCID_{50}$/ml) + CSFV C strain (F16) (7500 RID, or $10^{4.0}$ FA-$TCID_{50}$/ml) + PRV Bartha K61 ($10^{5.5}$ $TCID_{50}$/ml) | PRRSV TJ, $2 \times 10^{4.0}$-$2 \times 10^{4.5}$ $TCID_{50}$ | 5/5 | 5/5 |
| III | 3-combo vaccine, 1 ml/pig: PRRSV TJM ($10^{5.0}$ $TCID_{50}$/ml) + CSFV C strain (F16) (7500 RID, or $10^{4.0}$ FA-$TCID_{50}$/ml) + PRV Bartha K61 ($10^{5.5}$ $TCID_{50}$/ml) | PRV JL1: $10^{3.0}$-$10^{3.5}$ $TCID_{50}$ | 5/5 | 5/5 |
| IV | CSFV C strain (F16), 1 ml/pig: 7500 RID, or $10^{4.0}$ FA-$TCID_{50}$/ml | CSFV Shimen: $10^{6.0}$ MLD | 5/5 | 5/5 |
| V | PRRSV TJM, 1 ml/pig: $10^{5.0}$ $TCID_{50}$/ml | PRRSV TJ, $2 \times 10^{4.0}$-$2 \times 10^{4.5}$ $TCID_{50}$ | 4/5 | 4/5 |
| VI | PRV Bartha K61, 1 ml/pig: $10^{5.5}$ $TCID_{50}$/ml | PRV JL1: $10^{3.0}$-$10^{3.5}$ $TCID_{50}$ | 4/5 | 4/5 |
| VII | PBS, 1 ml/pig | CSFV Shimen: $10^{6.0}$ MLD | 0/3 | 0/3 |
| VIII | PBS, 1 ml/pig | PRRSV TJ, $2 \times 10^{4.0}$-$2 \times 10^{4.5}$ $TCID_{50}$ | 0/5 | 0/5 |
| IX | PBS, 1 ml/pig | PRV JL1: $10^{3.0}$-$10^{3.5}$ $TCID_{50}$ | 0/5 | 0/5 |

"RID": rabbit infective dose;

"MLD": minimum lethal dose;

Example 21

Safety Study of the Combined PRRSV and PRV Vaccine

Safety study was carried out using three batches of the 2-combo vaccine of PRRSV and PRV, as prepared according to Example 5.

Pigs aged 4-5 weeks, negative for both PRRS and PR, in terms of both antigen and antibody, were randomized in 3 groups, with 15 pigs in each group. Each group was inoculated with the 2-combo vaccine in a single dose ($10^{5.0}$-$10^{5.5}$ $TCID_{50}$ virus/ml), repetitive doses or a 10-fold over-dose. 5 pigs were used as a control group and were not inoculated at all.

Rectal temperatures of the pigs were taken each day, until the $21^{st}$ day after the vaccination. The pigs were also under close clinical observation.

The results showed that pigs in each group showed normal temperature and no pathological changes after vaccination. The 2-combo vaccine was safe to pigs.

Example 22

Safety Study of the Combined PRRSV, CSFV and PRV Vaccine

Safety study was carried out using three batches of the lab-made 3-combo vaccine for PRRSV, CSFV and PRV (batch No.: 031-01, 031-02, and 031-03), as prepared according to Example 6. The study included a single dose safety study, repetitive dose safety study, over-dose safety study on target age pigs, over-dose safety study on under-age pigs, and over-dose safety study on pigs of different breeds.

The results showed, after vaccination, pigs in each study group showed normal temperature, were in good spirits and good appetites. No systemic or local adverse effects were observed. Over-dose administration of the combination vaccine was shown to be safe to under-age pigs, and also to pigs of different breeds.

Part IV

Stability Studies

Example 23

Stability Study of the 2-Combo Vaccine for PRRSV and CSFV

The lab-made combined PRRSV and CSFV vaccines (batch Nos.: 200904, 200905, and 200906) were tested for stability, and compared in parallel with three batches of PRRSV single vaccine and CSFV single vaccine (batch Nos.: 200901, 200902, 200903, 200907, 200908, and 200909).

The three batches of each of the vaccine composition were kept at 2-8° C. Samples were collected at 3, 6, 9, 12, and 18 months of the study, respectively. The samples were tested for physiochemical properties, vacuum degree, residual water content, potency, and aging at 37° C.

After 18-month storage at 2-8° C., the three batches of the 2-combo vaccine compositions were in white loosen clumps, which were rapidly dissolved upon addition of a diluting buffer. In the test of degree of vacuum, the vaccines showed white or purple glow. The average residual water content of the tested vaccines met the requirements set by Chinese Veterinary Pharmacopoeia.

The virus titers of the vaccine compositions were determined, and the results were shown in FIGS. 27-30. After storage at 2-8° C. for 18 months, the virus titers of the 2-combo vaccine were not significantly different from that of each single vaccine. After being kept at 37° C. for 14 days, the 2-combo vaccines still contained high level of virus titers, which were not significantly different from each of the single vaccine in the parallel studies. The virus titers of the vaccine compositions met the requirement for a qualified vaccine. This showed that the heat-resistant cryoprotectant provided good protection to the PRRSV vaccine strain and the CSFV vaccine strain during the freeze-drying procedures.

As is known in the art, conventional vaccines are usually kept under 0° C. (−20° C.), which complicates the storage of the vaccines. The results of this Example showed that, with the new cryoprotectant, the vaccine compositions can be shipped and stored at a higher temperature, thereby providing a higher stability of the vaccines.

Example 24

Stability Study of the 2-Combo Vaccine for PRRSV and PRV

The three batches of lab-made 2-combo vaccines for PRRSV and PRV were kept at 2-8° C. Samples were collected at 3rd, 6th, 9th, 12th, 18th, 21st and 24th months of the study, respectively. The samples were tested for physiochemical properties, vacuum degree, residual water content, potency, and aging at 37° C.

After 24-month storage at 2-8° C., the three batches of the vaccine compositions were in white loosen clumps, which were rapidly dissolved upon addition of a diluting buffer. In the test of degree of vacuum, the vaccines showed white or purple glow. The virus titers of the vaccine compositions were determined, and the results were shown in FIGS. 31-34. The combined vaccines were stable after storage at 2-8° C. for 24 months, and the virus titers were not significantly different from those before the storage.

Example 25

Stability Study of the 3-Combo Vaccine for PRRSV, CSFV and PRV

The lab-made 3-combo vaccines for PRRSV, CSFV and PRV (batch Nos.: 031-01, 031-02, and 031-03) were tested for stability, and compared in parallel with three batches of PRRSV single vaccine (batch Nos.: 031-04, 031-05, 031-06), CSFV single vaccine (batch Nos.: 031-07, 031-08, 031-09) and PRV single vaccine (batch Nos.: 031-10, 031-11 and 031-12).

The vaccine compositions were kept at 2-8° C. Samples were collected at the 3rd, 6th, 9th, 12th, and 18th month of the study, respectively. The samples were tested for physiochemical properties, vacuum degree, residual water content, potency, and aging at 37° C.

After 18-month storage at 2-8° C., the three batches of the vaccine compositions were in white loosen clumps, which were rapidly dissolved upon addition of a diluting buffer. In the test of degree of vacuum, the vaccines showed white or purple glow. The average residual water content of the tested vaccines met the requirements set by Chinese Veterinary Pharmacopoeia.

The virus titers of the vaccine compositions were determined, and the results were shown in FIGS. 35-40. After storage at 2-8° C. for 18 months, the virus titers of the combined vaccines were not significantly different from that of the single vaccines. After being kept at 37° C. for 14 days, the combined vaccines still showed high level of virus titer, which was not significantly different from that of the single vaccines under the parallel studies. This demonstrated that, the heat-resistant cryoprotectant provided good protection to the PRRSV vaccine strain, the CSFV vaccine strain and the PRV vaccine strain during the freeze-drying procedures.

The invention claimed is:

1. A vaccine composition, comprising a Porcine Reproductive and Respiratory Syndrome Virus (PRRSV) vaccine and a second porcine virus vaccine, wherein the second porcine virus vaccine is selected from the group consisting of Classical Swine Fever Virus (CSFV) vaccine and Pseudorabies Virus (PRV) vaccine, and wherein the PRRSV vaccine comprises an attenuated PRRSV comprising an NSp2 nucleotide sequence encoded by a DNA sequence, wherein the DNA sequence, when compared with SEQ ID NO: 4, lacks a DNA fragment which comprises at least 50 contiguous nucleotides within SEQ. ID NO: 8, wherein the PRRSV vaccine and the second vaccine are substantially free from immuno-inhibition against each other.

2. The vaccine composition of claim 1, further comprising a third porcine virus vaccine, wherein the third porcine virus vaccine is selected from the group consisting of CSFV vaccine and PRV vaccine, and wherein the third vaccine is different from the second vaccine, wherein the PRRSV vaccine, the second vaccine and the third vaccine are substantially free from immuno-inhibition against each other.

3. The vaccine composition of claim 1, wherein the attenuated PRRSV is attenuated from a highly-pathogenic PRRSV.

4. The vaccine composition of claim 1, wherein the attenuated PRRSV comprises a PRRSV nucleotide sequence encoded by a sequence having at least 90% homology to SEQ ID NO: 3.

5. The vaccine composition of claim 4, wherein the attenuated PRRSV comprises a PRRSV nucleotide sequence encoded by SEQ ID NO: 3.

6. The vaccine composition of claim 4, wherein the attenuated PRRSV has a microorganism deposit number of CGMCC No.: 3121.

7. The vaccine composition of claim 1, wherein the CSFV vaccine comprises an attenuated CSFV.

8. The vaccine composition of claim 7, wherein the attenuated CSFV is encoded by a sequence having at least 80% homology to SEQ ID NO: 10.

9. The vaccine composition of claim 8, wherein the attenuated CSFV is encoded by SEQ ID NO: 10.

10. The vaccine composition of claim 8, wherein the attenuated CSFV has a microorganism deposit number of CGMCC No.: 3891.

11. The vaccine composition of claim 1, wherein the PRV vaccine comprises an attenuated PRV.

12. The vaccine composition of claim 11, wherein the attenuated PRV has one or more inactivated genes selected from the group consisting of TK, PK, RR, dUTPase, gG, gC, gE, gD and gI.

13. The vaccine composition of claim 12, wherein the attenuated PRV has an inactivated gE gene.

14. The vaccine composition of claim 11, wherein the attenuated PRV has a microorganism deposit number of CGMCC No.: 5076.

15. The vaccine composition of claim 1, wherein the vaccine composition provided herein comprises an immunologically effective amount of the PRRSV vaccine, the CSFV vaccine and/or the PRV vaccine.

16. The vaccine composition of claim 15, wherein the immunologically effective amount of the PRRSV vaccine is at least $10^{4.5}$ $TCID_{50}$, $10^{5.0}$ $TCID_{50}$, or $10^{5.5}$ $TCID_{50}$, the immunologically effective amount of the CSFV vaccine is at least $10^{0.5}$ FA-$TCID_{50}$ (fluorescent antibody—$TCID_{50}$), $10^{1.0}$ FA-$TCID_{50}$, $10^{1.5}$ FA-$TCID_{50}$, $10^{2.0}$ FA-$TCID_{50}$, $10^{2.5}$ FA-$TCID_{50}$, $10^{3.0}$ $TCID_{50}$, $10^{3.5}$ FA-$TCID_{50}$, $10^{4.0}$ FA-$TCID_{50}$, $10^{4.5}$ FA-$TCID_{50}$, or $10^{5.0}$ FA-$TCID_{50}$, or is at least 2.5 RID, 3 RID, 5 RID, 10 RID, 30 RID, 100 RID, 150 RID, 300 RID, 750 RID, 1000 RID, 3000 RID, or 7500 RID, and/or the immunologically effective amount of the PRV vaccine is at least $10^{3.0}$ $TCID_{50}$, $10^{3.5}$ $TCID_{50}$, $10^{4.0}$ $TCID_{50}$, $10^{4.5}$ $TCID_{50}$, $10^{5.0}$ $TCID_{50}$, $10^{5.5}$ $TCID_{50}$ or $10^{6.0}$ $TCID_{50}$.

17. The vaccine composition of claim 15, wherein the $TCID_{50}$ ratio of the PRRSV vaccine to the CSFV vaccine ranges from 10000:1 to 1:1.

18. The vaccine composition of claim 15, wherein the $TCID_{50}$ ratio of the PRRSV vaccine to the PRV vaccine ranges from 1:1 to 1:30.

19. The vaccine composition of claim 15, wherein the $TCID_{50}$ ratio of the PRRSV vaccine:the CSFV vaccine:the PRV vaccine ranges from about $10^4$:1:$10^5$ to about 5:1:6.

20. A method for preventing or treating Porcine Reproductive and Respiratory Syndrome, Classical Swine Fever, and/or Pseudorabies comprising:

administering the vaccine composition of claim 15 to a subject.

21. A method of immunizing a pig, comprising administering to the pig the vaccine composition of claim 15.

22. The vaccine composition of claim 1, wherein the CSFV is cultured in a cell line selected from the group consisting of ST, PK-15, Marc-145, MDBK, BT, PT, Vero, BHK-21, porcine kidney cell line (IBRS-2), rabbit kidney cell line (RK), and chicken embryo fibroblast cell line, or a primary cell which is porcine kidney primary cells.

23. The vaccine composition of claim 1, wherein the DNA fragment comprises at least 100, at least 120, at least 150, at least 180, at least 200, at least 210, at least 220, at least 230, at least 240, at least 250, at least 260, at least 270, at least 280, at least 290, at least 300, at least 310, at least 320, at least 330, at least 340, at least 350, or at least 360 contiguous nucleotides.

24. The vaccine composition of claim 1, wherein the DNA fragment comprises SEQ ID NO: 8.

25. The vaccine composition of claim 1, wherein the attenuated PRRSV further comprises an Nsp1 nucleotide sequence, which is encoded by a sequence having at least 90% homology to SEQ ID NO: 1.

26. The vaccine composition of claim 25, wherein the attenuated PRRSV comprises an Nsp1 nucleotide sequence encoded by SEQ ID NO: 1, and an Nsp2 nucleotide sequence encoded by SEQ ID NO: 2.

27. The vaccine composition of claim 1, further comprising an adjuvant.

28. The vaccine composition of claim 1, further comprising a cryoprotectant.

29. The vaccine composition of claim 28, wherein the cryoprotectant comprises sucrose, L-sodium glutamate, and/or lactalbumin hydrolysate.

30. A method for preparing the vaccine composition of claim 1, comprising:

(a) collecting PRRSV vaccine strain, CSFV vaccine strain and/or PRV vaccine strain, which are cultivated in their respective susceptible cells, and (b) mixing two or more of the virus strains at a suitable $TCID_{50}$ ratio.

31. The method of claim 30, wherein the susceptible cells for the PRRSV vaccine strain is a cell line selected from the group consisting of Marc-145, MA-104, Vero, and CL-2621, or a primary cell which is PAM cell.

32. The method of claim 30, wherein the susceptible cells for the CSFV vaccine strain is a cell line selected from the group consisting of BT, Vero, MPK, SK6, PK2*a*, CPK, RKC, MDBK, MDCK, CRFK, ST, and PT, or a primary cell which is BT cell.

33. The method of claim 30, wherein the susceptible cells for the PRV vaccine strain is a cell line selected from the group consisting of ST, PK-15, Marc-145, MDBK, BT, Vero, BHK-21, porcine kidney cell line (IBRS-2), rabbit kidney cell line (RK), and chicken embryo fibroblast cell line, or a primary cell which is porcine kidney primary cell.

34. The method of claim 30, wherein the cultivation comprises inoculating each vaccine strain to its susceptible cells at a cell density ranging from $1\times10^6$/ml-$5\times10^6$/ml in a roller bottle culture, or at a cell density ranging from $5\times10^6$/ml-$1\times10^7$/ml in a suspension culture with an introduced adherent carrier in a bioreactor.

35. The method of claim 34, wherein the PRRSV vaccine strain is inoculated at a Multiplicity of Infection (MOI) of 0.01-0.5, the CSFV vaccine strain is inoculated at a MOI of 0.1-0.5, and/or the PRV vaccine strain is inoculated at a MOI of 0.005-0.5.

36. The method of claim 30, wherein the step (b) comprises mixing the collected PRRSV vaccine virus with the CSFV vaccine virus at a $TCID_{50}$ ratio from 10000:1 to 1:1.

37. The method of claim 30, wherein the step (b) comprises mixing the collected PRRSV vaccine virus with the PRV vaccine virus at a $TCID_{50}$ ratio from 1:1 to 1:30.

38. The method of claim 30, wherein the step (b) comprises mixing the collected PRRSV vaccine virus, the CSFV vaccine virus, and the PRV vaccine virus at a $TCID_{50}$ ratio from $10^4$:1:$10^5$ to about 5:1:6.

39. The method of claim 30, wherein the step (b) further comprising mixing the mixture of the collected virus solutions with a cryoprotectant.

40. The method of claim 39, wherein the mixture of the collected virus solutions is mixed with the cryoprotectant in a volume ratio of 75-80:25-20.

41. A vaccine composition prepared using the method of claim 30.

42. A vaccine composition, comprising a Porcine Reproductive and Respiratory Syndrome Virus (PRRSV) vaccine and a second porcine virus vaccine, wherein the second porcine virus vaccine is selected from the group consisting of Classical Swine Fever Virus (CSFV) vaccine and Pseudorabies Virus (PRV) vaccine, and wherein the PRRSV vaccine comprises an attenuated PRRSV comprising an Nsp2 nucleotide sequence encoding for a Nsp2 protein sequence, wherein the Nsp2 protein sequence, when compared with SEQ ID NO: 11, lacks a peptide fragment which comprises at least 20 contiguous amino acids within SEQ ID NO: 9, wherein the PRRSV vaccine and the second vaccine are substantially free from immuno-inhibition against each other.

43. The vaccine composition of claim 42, wherein the peptide fragment comprises at least 30, at least 40, at least 50, at least 60, at least 70, at least 75, at least 80, at least 85, at least 90, at least 95, at least 100, at least 105, at least 110, at least 115, or at least 120 contiguous amino acids.

44. The vaccine composition of claim 42, wherein the peptide fragment comprises SEQ ID NO: 9.

45. A vaccine composition, comprising a Porcine Reproductive and Respiratory Syndrome Virus (PRRSV) vaccine and a second porcine virus vaccine, wherein the second porcine virus vaccine is selected from the group consisting of Classical Swine Fever Virus (CSFV) vaccine and Pseudorabies Virus (PRV) vaccine, wherein the PRRSV vaccine comprises an attenuated PRRSV attenuated from a highly-pathogenic PRRSV, and wherein the attenuated PRRSV comprises an Nsp2 nucleotide encoded by a DNA sequence which, when compared with SEQ ID NO: 5, lacks discontinuous 90 nucleotides within SEQ ID NO: 6, wherein the PRRSV vaccine and the second vaccine are substantially free from immuno-inhibition against each other.

46. The vaccine composition of claim 45, wherein the Nsp2 nucleotide is encoded by a sequence having at least 90% homology to SEQ ID NO: 2.

47. The vaccine composition of claim 46, wherein the Nsp2nucleotide is encoded by a sequence comprising SEQ ID NO: 2.

48. A vaccine composition, comprising a Porcine Reproductive and Respiratory Syndrome Virus (PRRSV) vaccine and a second porcine virus vaccine, wherein the second porcine virus vaccine is selected from the group consisting of Classical Swine Fever Virus (CSFV) vaccine and Pseudorabies Virus (PRV) vaccine, and wherein the PRRSV vaccine comprises an attenuated PRRSV comprising an NSp2 nucleotide sequence encoded by a DNA sequence having at least 90% homology to SEQ ID NO: 2, wherein the PRRSV vaccine and the second vaccine are substantially free from immuno-inhibition against each other.

49. A vaccine composition, comprising a Porcine Reproductive and Respiratory Syndrome Virus (PRRSV) vaccine and a second porcine virus vaccine, wherein the second porcine virus vaccine is selected from the group consisting of Classical Swine Fever Virus (CSFV) vaccine and Pseudorabies Virus (PRV) vaccine, and wherein the PRRSV vaccine comprises an attenuated PRRSV comprising an NSp2 nucleotide sequence encoding for a Nsp2 protein sequence having at least 90% homology to the Nsp2 protein sequence encoded by SEQ ID NO: 2, wherein the PRRSV vaccine and the second vaccine are substantially free from immuno-inhibition against each other.

* * * * *